United States Patent
Chou

(10) Patent No.: US 11,607,523 B2
(45) Date of Patent: Mar. 21, 2023

(54) ASPIRATION CATHETER SYSTEMS AND METHODS OF USE

(71) Applicant: Route 92 Medical, Inc., San Mateo, CA (US)

(72) Inventor: Tony M. Chou, San Mateo, CA (US)

(73) Assignee: Route 92 Medical, Inc., San Mateo, CA (US)

( * ) Notice: Subject to any disclaimer, the term of this patent is extended or adjusted under 35 U.S.C. 154(b) by 707 days.

(21) Appl. No.: 16/414,532

(22) Filed: May 16, 2019

(65) Prior Publication Data

US 2019/0351182 A1 Nov. 21, 2019

Related U.S. Application Data

(60) Provisional application No. 62/673,009, filed on May 17, 2018.

(51) Int. Cl.
*A61M 25/00* (2006.01)
*A61M 25/01* (2006.01)
(Continued)

(52) U.S. Cl.
CPC ......... *A61M 25/0026* (2013.01); *A61B 17/22* (2013.01); *A61M 25/005* (2013.01);
(Continued)

(58) Field of Classification Search
CPC .......... A61M 25/0026; A61M 25/0054; A61M 2025/0004; A61M 2025/0175;
(Continued)

(56) References Cited

U.S. PATENT DOCUMENTS

| 2,623,520 A | 12/1952 | Bamford, Jr. et al. |
| 2,730,101 A | 1/1956 | Hoffman |

(Continued)

FOREIGN PATENT DOCUMENTS

| CN | 101121055 A | 2/2008 |
| CN | 101588835 A | 11/2009 |

(Continued)

OTHER PUBLICATIONS

"2007 International Stroke Conference: Abstracts." Stroke, vol. 38, No. 2, 2007, pp. 454-607. Web. Downloaded Jun. 13, 2017.

(Continued)

*Primary Examiner* — Kevin C Sirmons
*Assistant Examiner* — Leah J Swanson
(74) *Attorney, Agent, or Firm* — Mintz Levin Cohn Ferris Glovsky and Popeo, P.C.

(57) ABSTRACT

A method of performing a medical procedure in a cerebral vessel of a patient including advancing a first catheter system towards an embolus within a cerebral blood vessel and a second catheter system towards the embolus through the first catheter, applying aspiration pressure through the lumen of the second catheter; anchoring a distal end of the second catheter onto the embolus via the aspiration pressure; applying a proximally-directed force on the second catheter; and advancing the first catheter over the second catheter towards the embolus while the distal end of the second catheter remains anchored onto the embolus; and automatically applying aspiration pressure within the first catheter upon the second catheter portion entering into the first catheter.

19 Claims, 31 Drawing Sheets

(51) Int. Cl.
*A61M 39/06* (2006.01)
*A61B 17/22* (2006.01)
*A61M 25/06* (2006.01)

(52) U.S. Cl.
CPC .... *A61M 25/0045* (2013.01); *A61M 25/0068* (2013.01); *A61M 25/0108* (2013.01); *A61M 25/0662* (2013.01); *A61M 39/06* (2013.01); *A61B 2017/22079* (2013.01); *A61M 2025/0039* (2013.01); *A61M 2025/0046* (2013.01); *A61M 2025/0183* (2013.01); *A61M 2039/062* (2013.01); *A61M 2210/12* (2013.01); *A61M 2210/127* (2013.01)

(58) Field of Classification Search
CPC .. A61M 2025/0039; A61M 2025/0006; A61M 2025/0681
See application file for complete search history.

(56) References Cited

U.S. PATENT DOCUMENTS

| | | |
|---|---|---|
| 3,612,050 A | 10/1971 | Sheridan |
| 3,631,848 A | 1/1972 | Muller |
| 3,949,757 A | 4/1976 | Sabel |
| 3,996,938 A | 12/1976 | Clark, III |
| 4,013,080 A | 3/1977 | Froning |
| 4,020,829 A | 5/1977 | Willson et al. |
| 4,033,331 A | 7/1977 | Guss et al. |
| 4,174,715 A | 11/1979 | Hasson |
| 4,319,580 A | 3/1982 | Colley et al. |
| 4,323,071 A | 4/1982 | Simpson et al. |
| 4,406,656 A | 9/1983 | Hattier et al. |
| 4,610,662 A | 9/1986 | Weikl et al. |
| 4,619,263 A | 10/1986 | Frisbie et al. |
| 4,676,249 A | 6/1987 | Arenas et al. |
| 4,723,549 A | 2/1988 | Wholey et al. |
| 4,728,319 A | 3/1988 | Masch |
| 4,739,768 A | 4/1988 | Engelson |
| 4,762,128 A | 8/1988 | Rosenbluth |
| 4,771,777 A | 9/1988 | Horzewski et al. |
| 4,784,636 A | 11/1988 | Rydell |
| 4,790,812 A | 12/1988 | Hawkins, Jr. et al. |
| 4,794,928 A | 1/1989 | Kletschka |
| 4,795,434 A | 1/1989 | Kujawski |
| 4,799,496 A | 1/1989 | Hargreaves et al. |
| 4,834,709 A | 5/1989 | Banning et al. |
| 4,840,690 A | 6/1989 | Melinyshyn et al. |
| 4,863,431 A | 9/1989 | Vaillancourt |
| 4,865,581 A | 9/1989 | Lundquist et al. |
| 4,873,978 A | 10/1989 | Ginsburg |
| 4,873,979 A | 10/1989 | Hanna |
| 4,883,460 A | 11/1989 | Zanetti |
| 4,887,613 A | 12/1989 | Farr et al. |
| 4,898,575 A | 2/1990 | Fischell et al. |
| 4,900,303 A | 2/1990 | Lemelson |
| 4,921,478 A | 5/1990 | Solano et al. |
| 4,921,479 A | 5/1990 | Grayzel |
| 4,921,484 A | 5/1990 | Hillstead |
| 4,923,462 A | 5/1990 | Stevens |
| 4,946,440 A | 8/1990 | Hall |
| 4,946,443 A | 8/1990 | Hauser et al. |
| 4,994,067 A | 2/1991 | Summers |
| 4,998,919 A | 3/1991 | Schnepp-Pesch et al. |
| 5,011,488 A | 4/1991 | Ginsburg |
| 5,011,490 A | 4/1991 | Fischell et al. |
| 5,053,008 A | 10/1991 | Bajaj |
| 5,059,178 A | 10/1991 | Ya |
| 5,102,415 A | 4/1992 | Guenther et al. |
| 5,103,827 A | 4/1992 | Smith |
| 5,108,419 A | 4/1992 | Reger et al. |
| 5,135,484 A | 8/1992 | Wright |
| 5,152,277 A | 10/1992 | Honda et al. |
| 5,161,534 A | 11/1992 | Berthiaume |
| 5,163,906 A | 11/1992 | Ahmadi |
| 5,185,004 A | 2/1993 | Lashinski |
| 5,188,621 A | 2/1993 | Samson |
| 5,200,248 A | 4/1993 | Thompson et al. |
| 5,207,648 A | 5/1993 | Gross |
| 5,211,651 A | 5/1993 | Reger et al. |
| 5,217,705 A | 6/1993 | Reno et al. |
| 5,219,332 A | 6/1993 | Nelson et al. |
| 5,243,997 A | 9/1993 | Uflacker et al. |
| 5,250,060 A | 10/1993 | Carbo et al. |
| 5,267,960 A | 12/1993 | Hayman et al. |
| 5,269,297 A | 12/1993 | Weng et al. |
| 5,308,318 A | 5/1994 | Plassche, Jr. |
| 5,312,338 A | 5/1994 | Nelson et al. |
| 5,312,356 A | 5/1994 | Engelson et al. |
| RE34,633 E | 6/1994 | Sos et al. |
| 5,324,262 A | 6/1994 | Fischell et al. |
| 5,325,868 A | 7/1994 | Kimmelstiel |
| 5,328,471 A | 7/1994 | Slepian |
| 5,338,300 A | 8/1994 | Cox |
| 5,352,197 A | 10/1994 | Hammersmark et al. |
| 5,364,358 A | 11/1994 | Hewitt et al. |
| 5,370,623 A | 12/1994 | Kreamer |
| 5,380,284 A | 1/1995 | Don Michael |
| 5,385,562 A | 1/1995 | Adams et al. |
| 5,392,778 A | 2/1995 | Horzewski |
| 5,395,383 A | 3/1995 | Adams et al. |
| 5,413,575 A | 5/1995 | Haenggi |
| 5,423,331 A | 6/1995 | Wysham |
| 5,429,605 A | 7/1995 | Richling: Bernd et al. |
| 5,437,632 A | 8/1995 | Engelson |
| 5,438,993 A | 8/1995 | Lynch et al. |
| 5,441,051 A | 8/1995 | Hileman et al. |
| 5,443,454 A | 8/1995 | Tanabe et al. |
| 5,454,795 A | 10/1995 | Samson |
| 5,465,716 A | 11/1995 | Avitall |
| 5,466,222 A | 11/1995 | Ressemann et al. |
| 5,476,450 A | 12/1995 | Ruggio |
| 5,484,407 A | 1/1996 | Osypka |
| 5,484,412 A | 1/1996 | Pierpont |
| 5,484,418 A | 1/1996 | Quiachon et al. |
| 5,485,667 A | 1/1996 | Kleshinski |
| 5,490,859 A | 2/1996 | Mische et al. |
| 5,492,530 A | 2/1996 | Fischell et al. |
| 5,496,294 A | 3/1996 | Hergenrother et al. |
| 5,501,694 A | 3/1996 | Ressemann et al. |
| 5,522,836 A | 6/1996 | Palermo |
| 5,527,292 A | 6/1996 | Adams et al. |
| 5,533,967 A | 7/1996 | Imran |
| 5,538,512 A | 7/1996 | Zenzon et al. |
| 5,542,936 A | 8/1996 | Razi |
| 5,542,937 A | 8/1996 | Chee et al. |
| 5,546,958 A | 8/1996 | Thorud et al. |
| 5,549,119 A | 8/1996 | Solar |
| 5,549,626 A | 8/1996 | Miller et al. |
| 5,558,635 A | 9/1996 | Cannon |
| 5,571,122 A | 11/1996 | Kelly et al. |
| 5,573,520 A | 11/1996 | Schwartz et al. |
| 5,578,009 A | 11/1996 | Kraus et al. |
| 5,591,194 A | 1/1997 | Berthiaume |
| 5,599,307 A | 2/1997 | Bacher et al. |
| 5,599,326 A | 2/1997 | Carter |
| 5,628,754 A | 5/1997 | Shevlin et al. |
| 5,643,254 A | 7/1997 | Scheldrup et al. |
| 5,658,263 A | 8/1997 | Dang et al. |
| 5,658,264 A | 8/1997 | Samson |
| 5,658,309 A | 8/1997 | Berthiaume et al. |
| 5,662,622 A | 9/1997 | Gore et al. |
| 5,667,499 A | 9/1997 | Welch et al. |
| 5,695,483 A | 12/1997 | Samson |
| 5,702,373 A | 12/1997 | Samson |
| 5,707,376 A | 1/1998 | Kavteladze et al. |
| 5,720,764 A | 2/1998 | Naderlinger |
| 5,730,734 A | 3/1998 | Adams et al. |
| 5,749,849 A | 5/1998 | Engelson |
| 5,749,858 A | 5/1998 | Cramer |
| 5,766,191 A | 6/1998 | Trerotola |
| 5,776,141 A | 7/1998 | Klein et al. |
| 5,776,142 A | 7/1998 | Gunderson |
| 5,794,629 A | 8/1998 | Frazee |

(56) References Cited

U.S. PATENT DOCUMENTS

| | | |
|---|---|---|
| 5,795,341 A | 8/1998 | Samson |
| 5,810,869 A | 9/1998 | Kaplan et al. |
| 5,810,874 A | 9/1998 | Lefebvre |
| 5,814,064 A | 9/1998 | Daniel et al. |
| 5,817,101 A | 10/1998 | Fiedler |
| 5,827,229 A | 10/1998 | Auth et al. |
| 5,827,242 A | 10/1998 | Follmer et al. |
| 5,833,650 A | 11/1998 | Imran |
| 5,836,868 A | 11/1998 | Ressemann et al. |
| 5,836,926 A | 11/1998 | Peterson et al. |
| 5,843,002 A | 12/1998 | Pecor et al. |
| 5,843,051 A | 12/1998 | Adams et al. |
| 5,843,103 A | 12/1998 | Wulfman |
| 5,846,251 A | 12/1998 | Hart |
| 5,851,189 A | 12/1998 | Forber |
| 5,851,210 A | 12/1998 | Torossian |
| 5,853,400 A | 12/1998 | Samson |
| 5,876,367 A | 3/1999 | Kaganov et al. |
| 5,876,386 A | 3/1999 | Samson |
| 5,882,329 A | 3/1999 | Patterson et al. |
| 5,882,334 A | 3/1999 | Sepetka et al. |
| 5,885,209 A | 3/1999 | Green |
| 5,891,114 A | 4/1999 | Chien et al. |
| 5,895,399 A | 4/1999 | Barbut et al. |
| 5,897,567 A | 4/1999 | Ressemann et al. |
| 5,899,890 A | 5/1999 | Chiang et al. |
| 5,899,892 A | 5/1999 | Mortier et al. |
| 5,908,407 A | 6/1999 | Frazee et al. |
| 5,910,154 A | 6/1999 | Tsugita et al. |
| 5,911,725 A | 6/1999 | Boury |
| 5,911,734 A | 6/1999 | Tsugita et al. |
| 5,913,848 A | 6/1999 | Luther et al. |
| 5,916,192 A | 6/1999 | Nita et al. |
| 5,916,208 A | 6/1999 | Luther et al. |
| 5,921,952 A | 7/1999 | Desmond, III et al. |
| 5,928,192 A | 7/1999 | Maahs |
| 5,928,260 A | 7/1999 | Chin et al. |
| 5,935,122 A | 8/1999 | Fourkas et al. |
| 5,935,139 A | 8/1999 | Bates |
| 5,938,645 A | 8/1999 | Gordon |
| 5,941,869 A | 8/1999 | Patterson et al. |
| 5,957,882 A | 9/1999 | Nita et al. |
| 5,972,019 A | 10/1999 | Engelson et al. |
| 5,976,093 A | 11/1999 | Jang |
| 5,976,178 A | 11/1999 | Goldsteen et al. |
| 5,997,508 A | 12/1999 | Lunn et al. |
| 5,997,523 A | 12/1999 | Jang |
| 5,997,557 A | 12/1999 | Barbut et al. |
| 6,004,310 A | 12/1999 | Bardsley et al. |
| 6,007,530 A | 12/1999 | Dornhofer et al. |
| 6,010,522 A | 1/2000 | Barbut et al. |
| 6,013,085 A | 1/2000 | Howard |
| 6,022,336 A | 2/2000 | Zadno-Azizi et al. |
| 6,022,340 A | 2/2000 | Sepetka et al. |
| 6,030,349 A | 2/2000 | Wilson et al. |
| 6,030,369 A | 2/2000 | Engelson et al. |
| 6,033,388 A | 3/2000 | Nordstrom et al. |
| 6,044,845 A | 4/2000 | Lewis |
| 6,053,903 A | 4/2000 | Samson |
| 6,053,904 A | 4/2000 | Scribner et al. |
| 6,066,149 A | 5/2000 | Samson et al. |
| 6,071,263 A | 6/2000 | Kirkman |
| 6,074,357 A | 6/2000 | Kaganov et al. |
| 6,074,398 A | 6/2000 | Leschinsky |
| 6,090,072 A | 7/2000 | Kratoska et al. |
| 6,090,118 A | 7/2000 | McGuckin, Jr. |
| 6,106,530 A | 8/2000 | Harada |
| 6,110,139 A | 8/2000 | Loubser |
| 6,117,141 A | 9/2000 | Ouchi |
| 6,120,480 A | 9/2000 | Zhang et al. |
| 6,135,991 A | 10/2000 | Muni et al. |
| 6,139,524 A | 10/2000 | Killion |
| 6,142,987 A | 11/2000 | Tsugita |
| 6,146,370 A | 11/2000 | Barbut |
| 6,146,373 A | 11/2000 | Cragg et al. |
| 6,146,396 A | 11/2000 | Konya et al. |
| 6,146,415 A | 11/2000 | Fitz |
| 6,152,909 A | 11/2000 | Bagaoisan et al. |
| 6,152,912 A | 11/2000 | Jansen et al. |
| 6,156,005 A | 12/2000 | Theron |
| 6,159,195 A | 12/2000 | Ha et al. |
| 6,159,230 A | 12/2000 | Samuels |
| 6,161,547 A | 12/2000 | Barbut |
| 6,165,163 A | 12/2000 | Chien et al. |
| 6,165,199 A | 12/2000 | Barbut |
| 6,168,579 B1 | 1/2001 | Tsugita |
| 6,171,295 B1 | 1/2001 | Garabedian et al. |
| 6,176,844 B1 | 1/2001 | Lee |
| 6,197,016 B1 | 3/2001 | Fourkas et al. |
| 6,203,561 B1 | 3/2001 | Ramee et al. |
| 6,206,868 B1 | 3/2001 | Parodi |
| 6,210,370 B1 | 4/2001 | Chi-Sing et al. |
| 6,221,038 B1 | 4/2001 | Brisken |
| 6,221,049 B1 | 4/2001 | Selmon et al. |
| 6,228,046 B1 | 5/2001 | Brisken |
| 6,234,971 B1 | 5/2001 | Jang |
| 6,238,402 B1 | 5/2001 | Sullivan, III et al. |
| 6,238,412 B1 | 5/2001 | Dubrul et al. |
| 6,238,430 B1 | 5/2001 | Klumb et al. |
| 6,240,231 B1 | 5/2001 | Ferrera et al. |
| 6,254,628 B1 | 7/2001 | Wallace et al. |
| 6,258,052 B1 | 7/2001 | Milo |
| 6,258,080 B1 | 7/2001 | Samson |
| 6,258,115 B1 | 7/2001 | Dubrul |
| 6,270,477 B1 | 8/2001 | Bagaoisan et al. |
| 6,277,115 B1 | 8/2001 | Saadat |
| 6,277,139 B1 | 8/2001 | Levinson et al. |
| 6,287,319 B1 | 9/2001 | Aboul-Hosn et al. |
| 6,295,989 B1 | 10/2001 | Connors, III |
| 6,295,990 B1 | 10/2001 | Lewis et al. |
| 6,306,106 B1 | 10/2001 | Boyle |
| 6,306,163 B1 | 10/2001 | Fitz |
| 6,346,116 B1 | 2/2002 | Brooks et al. |
| 6,355,027 B1 | 3/2002 | Le et al. |
| 6,361,545 B1 | 3/2002 | Macoviak et al. |
| 6,364,894 B1 | 4/2002 | Healy et al. |
| 6,364,900 B1 | 4/2002 | Heuser |
| 6,368,316 B1 | 4/2002 | Jansen et al. |
| 6,368,338 B1 | 4/2002 | Konya et al. |
| 6,368,344 B1 | 4/2002 | Fitz |
| 6,379,325 B1 | 4/2002 | Benett et al. |
| 6,383,172 B1 | 5/2002 | Barbut |
| 6,391,044 B1 | 5/2002 | Yadav et al. |
| 6,394,976 B1 | 5/2002 | Winston et al. |
| 6,413,235 B1 | 7/2002 | Parodi |
| 6,423,032 B2 | 7/2002 | Parodi |
| 6,423,086 B1 | 7/2002 | Barbut et al. |
| 6,428,531 B1 | 8/2002 | Visuri et al. |
| 6,435,189 B1 | 8/2002 | Lewis et al. |
| 6,436,087 B1 | 8/2002 | Lewis et al. |
| 6,451,005 B1 | 9/2002 | Saitou et al. |
| 6,454,741 B1 | 9/2002 | Muni et al. |
| 6,454,775 B1 | 9/2002 | Demarais et al. |
| 6,458,151 B1 | 10/2002 | Saltiel |
| 6,464,664 B1 | 10/2002 | Jonkman et al. |
| 6,468,219 B1 | 10/2002 | Njemanze |
| 6,475,195 B1 | 11/2002 | Voda |
| 6,481,439 B1 | 11/2002 | Lewis et al. |
| 6,482,172 B1 | 11/2002 | Thramann |
| 6,482,217 B1 | 11/2002 | Pintor et al. |
| 6,485,466 B2 | 11/2002 | Hamilton |
| 6,485,500 B1 | 11/2002 | Kokish et al. |
| 6,485,501 B1 | 11/2002 | Green |
| 6,508,824 B1 | 1/2003 | Flaherty et al. |
| 6,511,470 B1 | 1/2003 | Hamilton |
| 6,511,471 B2 | 1/2003 | Rosenman et al. |
| 6,514,261 B1 | 2/2003 | Randall et al. |
| 6,514,273 B1 | 2/2003 | Voss et al. |
| 6,517,520 B2 | 2/2003 | Chang et al. |
| 6,524,303 B1 | 2/2003 | Garibaldi |
| 6,527,746 B1 | 3/2003 | Oslund et al. |
| 6,533,800 B1 | 3/2003 | Barbut |
| 6,537,295 B2 | 3/2003 | Petersen |
| 6,540,712 B1 | 4/2003 | Parodi et al. |

(56) References Cited

U.S. PATENT DOCUMENTS

| | | |
|---|---|---|
| 6,540,768 B1 | 4/2003 | Diaz et al. |
| 6,544,276 B1 | 4/2003 | Azizi |
| 6,549,800 B1 | 4/2003 | Atalar et al. |
| 6,551,268 B1 | 4/2003 | Kaganov et al. |
| 6,551,273 B1 | 4/2003 | Olson et al. |
| 6,551,302 B1 | 4/2003 | Rosinko et al. |
| 6,554,820 B1 | 4/2003 | Wendlandt et al. |
| 6,554,827 B2 | 4/2003 | Chandrasekaran et al. |
| 6,555,057 B1 | 4/2003 | Barbut et al. |
| 6,558,377 B2 | 5/2003 | Lee et al. |
| 6,558,405 B1 | 5/2003 | McInnes |
| 6,562,049 B1 | 5/2003 | Norlander et al. |
| 6,562,052 B2 | 5/2003 | Nobles et al. |
| 6,569,148 B2 | 5/2003 | Bagaoisan et al. |
| 6,579,246 B2 | 6/2003 | Jacobsen et al. |
| 6,579,264 B1 | 6/2003 | Rossi |
| 6,579,484 B1 | 6/2003 | Tiernan et al. |
| 6,582,390 B1 | 6/2003 | Sanderson |
| 6,582,396 B1 | 6/2003 | Parodi |
| 6,582,440 B1 | 6/2003 | Brumbach |
| 6,582,448 B1 | 6/2003 | Boyle et al. |
| 6,589,262 B1 | 7/2003 | Honebrink et al. |
| 6,595,953 B1 | 7/2003 | Coppi et al. |
| 6,595,980 B1 | 7/2003 | Barbut |
| 6,596,011 B2 | 7/2003 | Johnson et al. |
| 6,605,074 B2 | 8/2003 | Zadno-Azizi et al. |
| 6,610,077 B1 | 8/2003 | Hancock et al. |
| 6,612,999 B2 | 9/2003 | Brennan et al. |
| 6,616,681 B2 | 9/2003 | Hanson et al. |
| 6,620,148 B1 | 9/2003 | Tsugita |
| 6,623,471 B1 | 9/2003 | Barbut |
| 6,623,491 B2 | 9/2003 | Thompson |
| 6,623,518 B2 | 9/2003 | Thompson et al. |
| 6,626,886 B1 | 9/2003 | Barbut |
| 6,632,236 B2 | 10/2003 | Hogendijk |
| 6,635,070 B2 | 10/2003 | Leeflang et al. |
| 6,638,243 B2 | 10/2003 | Kupiecki |
| 6,638,245 B2 | 10/2003 | Miller et al. |
| 6,641,573 B1 | 11/2003 | Parodi |
| 6,645,160 B1 | 11/2003 | Heesch |
| 6,645,222 B1 | 11/2003 | Parodi et al. |
| 6,652,480 B1 | 11/2003 | Imran et al. |
| 6,656,152 B2 | 12/2003 | Putz |
| 6,663,650 B2 | 12/2003 | Sepetka et al. |
| 6,663,652 B2 | 12/2003 | Daniel et al. |
| 6,676,637 B1 | 1/2004 | Bonnette et al. |
| 6,679,893 B1 | 1/2004 | Tran |
| 6,682,505 B2 | 1/2004 | Bates et al. |
| 6,685,722 B1 | 2/2004 | Rosenbluth et al. |
| 6,692,473 B2 | 2/2004 | St. Cyr et al. |
| 6,695,858 B1 | 2/2004 | Dubrul et al. |
| 6,695,865 B2 | 2/2004 | Boyle et al. |
| 6,702,782 B2 | 3/2004 | Miller et al. |
| 6,702,834 B2 | 3/2004 | Boylan et al. |
| 6,711,436 B1 | 3/2004 | Duhaylongsod |
| 6,719,717 B1 | 4/2004 | Johnson et al. |
| 6,726,675 B1 | 4/2004 | Eeyar |
| 6,730,104 B1 | 5/2004 | Sepetka et al. |
| 6,733,517 B1 | 5/2004 | Collins |
| 6,740,104 B1 | 5/2004 | Solar et al. |
| 6,749,627 B2 | 6/2004 | Thompson et al. |
| 6,755,803 B1 | 6/2004 | Le et al. |
| 6,755,812 B2 | 6/2004 | Peterson et al. |
| 6,755,847 B2 | 6/2004 | Eskuri |
| 6,758,854 B1 | 7/2004 | Butler et al. |
| 6,764,464 B2 | 7/2004 | McGuckin, Jr. et al. |
| 6,773,448 B2 | 8/2004 | Kusleika et al. |
| 6,790,204 B2 | 9/2004 | Zadno-Azizi et al. |
| 6,805,684 B2 | 10/2004 | Bonnette et al. |
| 6,805,692 B2 | 10/2004 | Muni et al. |
| 6,824,545 B2 | 11/2004 | Sepetka et al. |
| 6,824,550 B1 | 11/2004 | Noriega et al. |
| 6,824,553 B1 | 11/2004 | Samson et al. |
| 6,827,730 B1 | 12/2004 | Leschinsky |
| 6,837,881 B1 | 1/2005 | Barbut |
| 6,840,949 B2 | 1/2005 | Barbut |
| 6,849,068 B1 | 2/2005 | Bagaoisan et al. |
| 6,855,136 B2 | 2/2005 | Dorros et al. |
| 6,866,669 B2 | 3/2005 | Buzzard et al. |
| 6,878,151 B2 | 4/2005 | Carrison et al. |
| 6,879,854 B2 | 4/2005 | Windheuser et al. |
| 6,884,235 B2 | 4/2005 | McGuckin, Jr. et al. |
| 6,902,540 B2 | 6/2005 | Dorros et al. |
| 6,905,490 B2 | 6/2005 | Parodi |
| 6,905,505 B2 | 6/2005 | Nash et al. |
| 6,908,474 B2 | 6/2005 | Hogendijk et al. |
| 6,911,036 B2 | 6/2005 | Douk et al. |
| 6,929,632 B2 | 8/2005 | Nita et al. |
| 6,929,634 B2 | 8/2005 | Dorros et al. |
| 6,936,060 B2 | 8/2005 | Hogendijk et al. |
| 6,945,956 B2 | 9/2005 | Waldhauser et al. |
| 6,949,104 B2 | 9/2005 | Griffis et al. |
| 6,951,570 B2 | 10/2005 | Linder et al. |
| 6,958,059 B2 | 10/2005 | Zadno-Azizi |
| 6,960,189 B2 | 11/2005 | Bates et al. |
| 6,969,395 B2 | 11/2005 | Eskuri |
| 6,972,030 B2 | 12/2005 | Lee et al. |
| 6,977,068 B1 | 12/2005 | Nair et al. |
| 6,991,642 B2 | 1/2006 | Petersen |
| 7,001,400 B1 | 2/2006 | Modesitt et al. |
| 7,004,924 B1 | 2/2006 | Brugger et al. |
| 7,004,931 B2 | 2/2006 | Hogendijk |
| 7,004,952 B2 | 2/2006 | Nobles et al. |
| 7,022,100 B1 | 4/2006 | Aboul-Hosn et al. |
| 7,029,488 B2 | 4/2006 | Schonholz et al. |
| 7,033,325 B1 | 4/2006 | Sullivan |
| 7,033,336 B2 | 4/2006 | Hogendijk |
| 7,033,344 B2 | 4/2006 | Imran |
| 7,037,267 B1 | 5/2006 | Lipson et al. |
| 7,048,758 B2 | 5/2006 | Boyle et al. |
| 7,052,500 B2 | 5/2006 | Bashiri et al. |
| 7,056,328 B2 | 6/2006 | Arnott |
| 7,063,714 B2 | 6/2006 | Dorros et al. |
| 7,083,594 B2 | 8/2006 | Coppi |
| 7,104,979 B2 | 9/2006 | Jansen et al. |
| 7,108,677 B2 | 9/2006 | Courtney et al. |
| 7,115,134 B2 | 10/2006 | Chambers |
| 7,115,138 B2 | 10/2006 | Renati et al. |
| 7,144,386 B2 | 12/2006 | Korkor et al. |
| 7,150,712 B2 | 12/2006 | Buehlmann et al. |
| 7,152,605 B2 | 12/2006 | Khairkhahan et al. |
| 7,166,088 B2 | 1/2007 | Heuser |
| 7,166,120 B2 | 1/2007 | Kusleika |
| 7,169,165 B2 | 1/2007 | Belef et al. |
| 7,172,621 B2 | 2/2007 | Theron |
| 7,220,271 B2 | 5/2007 | Clubb et al. |
| 7,223,253 B2 | 5/2007 | Hogendijk |
| 7,229,431 B2 | 6/2007 | Houser et al. |
| 7,229,463 B2 | 6/2007 | Sutton et al. |
| 7,229,464 B2 | 6/2007 | Hanson et al. |
| 7,232,452 B2 | 6/2007 | Adams et al. |
| 7,250,042 B2 | 7/2007 | Kataishi et al. |
| 7,285,126 B2 | 10/2007 | Sepetka et al. |
| 7,306,585 B2 | 12/2007 | Ross |
| 7,309,334 B2 | 12/2007 | von Hoffmann |
| 7,316,678 B2 | 1/2008 | Nash et al. |
| 7,329,278 B2 | 2/2008 | Seguin et al. |
| 7,367,982 B2 | 5/2008 | Nash et al. |
| 7,374,560 B2 | 5/2008 | Ressemann et al. |
| 7,374,561 B2 | 5/2008 | Barbut |
| 7,374,564 B2 | 5/2008 | Brown |
| 7,384,412 B2 | 6/2008 | Coppi |
| 7,402,151 B2 | 7/2008 | Rosenman et al. |
| 7,422,579 B2 | 9/2008 | Wahr et al. |
| 7,449,010 B1 | 11/2008 | Hayase et al. |
| 7,458,980 B2 | 12/2008 | Barbut |
| 7,476,232 B2 | 1/2009 | Deal |
| 7,497,844 B2 | 3/2009 | Spear et al. |
| 7,507,229 B2 | 3/2009 | Hewitt et al. |
| 7,524,303 B1 | 4/2009 | Don Michael et al. |
| 7,534,250 B2 | 5/2009 | Schaeffer et al. |
| 7,537,568 B2 | 5/2009 | Moehring |
| 7,549,974 B2 | 6/2009 | Nayak |
| 7,558,622 B2 | 7/2009 | Tran |

(56) References Cited

U.S. PATENT DOCUMENTS

| | | |
|---|---|---|
| 7,604,612 B2 | 10/2009 | Ressemann et al. |
| 7,625,207 B2 | 12/2009 | Hershey et al. |
| 7,691,121 B2 | 4/2010 | Rosenbluth et al. |
| 7,731,683 B2 | 6/2010 | Jang et al. |
| 7,736,355 B2 | 6/2010 | Itou et al. |
| 7,766,049 B2 | 8/2010 | Miller et al. |
| 7,766,820 B2 | 8/2010 | Core |
| 7,771,358 B2 | 8/2010 | Moehring et al. |
| 7,803,136 B2 | 9/2010 | Schatz |
| 7,806,906 B2 | 10/2010 | Don Michael |
| 7,815,626 B1 | 10/2010 | McFadden et al. |
| 7,837,692 B2 | 11/2010 | Mulholland et al. |
| 7,842,055 B2 | 11/2010 | Pintor et al. |
| 7,842,065 B2 | 11/2010 | Belef et al. |
| 7,850,642 B2 | 12/2010 | Moll et al. |
| 7,850,654 B2 | 12/2010 | Belhe et al. |
| 7,854,746 B2 | 12/2010 | Dorn et al. |
| 7,867,216 B2 | 1/2011 | Wahr et al. |
| 7,879,062 B2 | 2/2011 | Galdonik et al. |
| 7,905,856 B2 | 3/2011 | McGuckin, Jr. et al. |
| 7,905,877 B1 | 3/2011 | Jimenez et al. |
| 7,905,891 B2 | 3/2011 | Self |
| 7,909,812 B2 | 3/2011 | Jansen et al. |
| 7,927,309 B2 | 4/2011 | Palm |
| 7,927,347 B2 | 4/2011 | Hogendijk et al. |
| 7,931,659 B2 | 4/2011 | Bose et al. |
| 7,938,820 B2 | 5/2011 | Webster et al. |
| 7,967,789 B2 | 6/2011 | Solar et al. |
| 7,972,294 B2 | 7/2011 | Nash et al. |
| 7,972,298 B2 | 7/2011 | Wallace et al. |
| 7,972,308 B2 | 7/2011 | Putz |
| 7,988,646 B2 | 8/2011 | Taber |
| 7,998,104 B2 | 8/2011 | Chang |
| 8,021,351 B2 | 9/2011 | Boldenow et al. |
| 8,029,533 B2 | 10/2011 | Bagaoisan et al. |
| 8,048,032 B2 | 11/2011 | Root et al. |
| 8,052,636 B2 | 11/2011 | Moll et al. |
| 8,052,640 B2 | 11/2011 | Fiorella et al. |
| 8,066,757 B2 | 11/2011 | Ferrera et al. |
| 8,070,694 B2 | 12/2011 | Galdonik et al. |
| 8,084,246 B2 | 12/2011 | Hoon et al. |
| 8,092,483 B2 | 1/2012 | Galdonik et al. |
| 8,114,032 B2 | 2/2012 | Ferry et al. |
| 8,142,413 B2 | 3/2012 | Root et al. |
| RE43,300 E | 4/2012 | Saadat et al. |
| 8,152,782 B2 | 4/2012 | Jang et al. |
| 8,157,760 B2 | 4/2012 | Criado et al. |
| 8,172,831 B2 | 5/2012 | Webler, Jr. |
| 8,181,324 B2 | 5/2012 | McFadden et al. |
| 8,211,023 B2 | 7/2012 | Swan et al. |
| 8,221,348 B2 | 7/2012 | Hackett et al. |
| 8,231,600 B2 | 7/2012 | von Hoffmann |
| 8,235,968 B2 | 8/2012 | Tremaglio |
| 8,251,978 B2 | 8/2012 | Nash et al. |
| 8,252,010 B1 | 8/2012 | Raju et al. |
| 8,252,014 B2 | 8/2012 | Fisher |
| 8,292,850 B2 | 10/2012 | Root et al. |
| 8,308,712 B2 | 11/2012 | Provost et al. |
| 8,343,089 B2 | 1/2013 | Chang |
| 8,366,735 B2 | 2/2013 | Bose et al. |
| 8,414,516 B2 | 4/2013 | Chang |
| 8,419,786 B2 | 4/2013 | Cottone, Jr. et al. |
| 8,425,549 B2 | 4/2013 | Lenker et al. |
| 8,460,312 B2 | 6/2013 | Bose et al. |
| 8,465,456 B2 | 6/2013 | Stivland |
| 8,523,801 B2 | 9/2013 | Nash et al. |
| 8,535,272 B2 | 9/2013 | Wang et al. |
| 8,545,552 B2 | 10/2013 | Garrison et al. |
| 8,574,245 B2 | 11/2013 | Garrison et al. |
| 8,609,426 B2 | 12/2013 | Silver |
| 8,663,259 B2 | 3/2014 | Levine et al. |
| 8,682,411 B2 | 3/2014 | Kassab et al. |
| 8,690,907 B1 | 4/2014 | Janardhan et al. |
| 8,702,680 B2 | 4/2014 | Jimenez et al. |
| 8,708,954 B2 | 4/2014 | Webler |
| 8,725,249 B2 | 5/2014 | Bar-Yoseph et al. |
| 8,734,374 B2 | 5/2014 | Aklog et al. |
| 8,758,325 B2 | 6/2014 | Webster et al. |
| 8,764,779 B2 | 7/2014 | Levine et al. |
| 8,764,813 B2 | 7/2014 | Jantzen et al. |
| 8,795,305 B2 | 8/2014 | Martin et al. |
| 8,814,892 B2 | 8/2014 | Galdonik et al. |
| 8,870,805 B2 | 10/2014 | Chang |
| 8,876,776 B2 | 11/2014 | Kassab et al. |
| 8,932,286 B2 | 1/2015 | Terry et al. |
| 8,932,320 B1 | 1/2015 | Janardhan et al. |
| RE45,380 E | 2/2015 | Root et al. |
| 8,961,533 B2 | 2/2015 | Stabler et al. |
| 8,961,549 B2 | 2/2015 | Conn |
| 8,974,411 B2 | 3/2015 | McKinnon |
| 8,996,095 B2 | 3/2015 | Anderson et al. |
| 9,014,786 B2 | 4/2015 | Carmeli et al. |
| 9,023,070 B2 | 5/2015 | Levine et al. |
| 9,034,007 B2 | 5/2015 | Janardhan |
| 9,107,691 B2 | 8/2015 | Fojtik |
| 9,119,656 B2 | 9/2015 | Bose et al. |
| 9,126,018 B1 | 9/2015 | Garrison |
| 9,144,383 B2 | 9/2015 | Zharov |
| 9,144,662 B2 | 9/2015 | Di Caprio et al. |
| RE45,760 E | 10/2015 | Root et al. |
| RE45,776 E | 10/2015 | Root et al. |
| 9,199,057 B2 | 12/2015 | Nielsen |
| 9,220,562 B2 | 12/2015 | Brannan et al. |
| 9,233,230 B2 | 1/2016 | Puhasmagi et al. |
| 9,241,699 B1 | 1/2016 | Kume et al. |
| 9,259,215 B2 | 2/2016 | Chou et al. |
| 9,259,228 B2 | 2/2016 | Cruise et al. |
| 9,265,512 B2 | 2/2016 | Garrison et al. |
| 9,278,201 B2 | 3/2016 | Rapaport et al. |
| 9,282,992 B2 | 3/2016 | Levine et al. |
| 9,295,817 B2 | 3/2016 | Chang |
| 9,314,268 B2 | 4/2016 | Cahill |
| 9,351,993 B2 | 5/2016 | Cruise et al. |
| 9,352,123 B2 | 5/2016 | Zhou et al. |
| 9,370,639 B2 | 6/2016 | Plassman et al. |
| 9,375,223 B2 | 6/2016 | Wallace |
| 9,381,278 B2 | 7/2016 | Constant et al. |
| 9,399,118 B2 | 7/2016 | Kume et al. |
| RE46,116 E | 8/2016 | Root et al. |
| 9,408,916 B2 | 8/2016 | Cruise et al. |
| 9,414,819 B2 | 8/2016 | Fitz et al. |
| 9,433,427 B2 | 9/2016 | Look et al. |
| 9,439,791 B2 | 9/2016 | Vong et al. |
| 9,445,828 B2 | 9/2016 | Turjman et al. |
| 9,451,884 B2 | 9/2016 | Zharov et al. |
| 9,451,963 B2 | 9/2016 | Cruise et al. |
| 9,486,221 B2 | 11/2016 | Cruise et al. |
| 9,486,611 B2 | 11/2016 | Petersen et al. |
| 9,492,637 B2 | 11/2016 | Garrison et al. |
| 9,504,476 B2 | 11/2016 | Gulachenski |
| 9,510,855 B2 | 12/2016 | Rapaport et al. |
| 9,526,504 B2 | 12/2016 | Chang |
| 9,526,505 B2 | 12/2016 | Marks et al. |
| 9,532,792 B2 | 1/2017 | Galdonik et al. |
| 9,533,344 B2 | 1/2017 | Monetti et al. |
| 9,539,022 B2 | 1/2017 | Bowman |
| 9,539,122 B2 | 1/2017 | Burke et al. |
| 9,546,236 B2 | 1/2017 | Cruise et al. |
| 9,561,121 B2 | 2/2017 | Sudin et al. |
| 9,561,125 B2 | 2/2017 | Bowman et al. |
| 9,561,345 B2 | 2/2017 | Garrison et al. |
| 9,597,101 B2 | 3/2017 | Galdonik et al. |
| 9,615,832 B2 | 4/2017 | Bose et al. |
| 9,622,753 B2 | 4/2017 | Cox |
| 9,623,228 B2 | 4/2017 | Ryan et al. |
| 9,655,633 B2 | 5/2017 | Leynov et al. |
| 9,655,755 B2 | 5/2017 | Chou et al. |
| 9,655,989 B2 | 5/2017 | Cruise et al. |
| 9,662,118 B2 | 5/2017 | Chang |
| 9,662,129 B2 | 5/2017 | Galdonik et al. |
| 9,662,480 B2 | 5/2017 | Kume et al. |
| 9,669,183 B2 | 6/2017 | Chang |
| 9,669,191 B2 | 6/2017 | Chou et al. |
| 9,681,882 B2 | 6/2017 | Garrison et al. |

(56) References Cited

U.S. PATENT DOCUMENTS

| | | |
|---|---|---|
| 9,688,788 B2 | 6/2017 | Plotkin et al. |
| 9,693,789 B2 | 7/2017 | Garrison et al. |
| 9,693,852 B2 | 7/2017 | Lam et al. |
| 9,717,500 B2 | 8/2017 | Tieu et al. |
| 9,724,103 B2 | 8/2017 | Cruise et al. |
| 9,764,111 B2 | 9/2017 | Gulachenski |
| 9,770,251 B2 | 9/2017 | Bowman et al. |
| 9,789,242 B2 | 10/2017 | Criado et al. |
| 9,803,043 B2 | 10/2017 | Cruise et al. |
| 9,820,761 B2 | 11/2017 | Garrison et al. |
| 9,827,047 B2 | 11/2017 | Fudaba et al. |
| 9,861,783 B2 | 1/2018 | Garrison et al. |
| 9,877,731 B2 | 1/2018 | Cruise et al. |
| 9,883,885 B2 | 2/2018 | Hendrick et al. |
| 9,907,880 B2 | 3/2018 | Cruise et al. |
| 10,058,339 B2 | 8/2018 | Galdonik et al. |
| 10,124,146 B2 | 11/2018 | Di Caprio et al. |
| 10,183,146 B2 | 1/2019 | Yang et al. |
| 10,192,230 B2 | 1/2019 | Look et al. |
| 10,441,301 B2 | 10/2019 | Vale et al. |
| 10,485,956 B2 | 11/2019 | O'Donovan |
| 2001/0014790 A1 | 8/2001 | Heller et al. |
| 2001/0027310 A1 | 10/2001 | Parisi et al. |
| 2001/0031980 A1 | 10/2001 | Wensel et al. |
| 2001/0044598 A1 | 11/2001 | Parodi |
| 2001/0044600 A1 | 11/2001 | Elkins |
| 2001/0044632 A1 | 11/2001 | Daniel et al. |
| 2001/0049486 A1 | 12/2001 | Evans et al. |
| 2001/0049517 A1 | 12/2001 | Zadno-Azizi et al. |
| 2001/0051811 A1 | 12/2001 | Bonnette et al. |
| 2002/0016565 A1 | 2/2002 | Zadno-Azizi et al. |
| 2002/0026145 A1 | 2/2002 | Bagaoisan et al. |
| 2002/0035347 A1 | 3/2002 | Bagaoisan et al. |
| 2002/0055747 A1 | 5/2002 | Cano et al. |
| 2002/0062133 A1 | 5/2002 | Gilson et al. |
| 2002/0072705 A1 | 6/2002 | Vrba et al. |
| 2002/0087076 A1 | 7/2002 | Meguro et al. |
| 2002/0087119 A1 | 7/2002 | Parodi |
| 2002/0091407 A1 | 7/2002 | Zadno-Azizi et al. |
| 2002/0095174 A1 | 7/2002 | Tsugita et al. |
| 2002/0111648 A1 | 8/2002 | Kusleika et al. |
| 2002/0123765 A1 | 9/2002 | Sepetka et al. |
| 2002/0128679 A1 | 9/2002 | Turovskiy et al. |
| 2002/0133111 A1 | 9/2002 | Shadduck |
| 2002/0138094 A1 | 9/2002 | Borillo et al. |
| 2002/0143362 A1 | 10/2002 | Macoviak et al. |
| 2002/0151922 A1 | 10/2002 | Hogendijk et al. |
| 2002/0151927 A1 | 10/2002 | Douk et al. |
| 2002/0156455 A1 | 10/2002 | Barbut |
| 2002/0156460 A1 | 10/2002 | Ye et al. |
| 2002/0165571 A1 | 11/2002 | Hebert et al. |
| 2002/0165574 A1 | 11/2002 | Ressemann et al. |
| 2002/0165598 A1 | 11/2002 | Wahr et al. |
| 2002/0169472 A1 | 11/2002 | Douk et al. |
| 2002/0173785 A1 | 11/2002 | Spear et al. |
| 2002/0173815 A1 | 11/2002 | Hogendijk et al. |
| 2002/0177899 A1 | 11/2002 | Eum et al. |
| 2002/0183782 A1 | 12/2002 | Tsugita et al. |
| 2002/0183783 A1 | 12/2002 | Shadduck |
| 2003/0023263 A1 | 1/2003 | Krolik et al. |
| 2003/0040762 A1 | 2/2003 | Dorros et al. |
| 2003/0050600 A1 | 3/2003 | Ressemann et al. |
| 2003/0065353 A1 | 4/2003 | Horzewski et al. |
| 2003/0065356 A1 | 4/2003 | Tsugita et al. |
| 2003/0069468 A1 | 4/2003 | Bolling et al. |
| 2003/0078562 A1 | 4/2003 | Makower et al. |
| 2003/0120208 A1 | 6/2003 | Houser et al. |
| 2003/0135193 A1 | 7/2003 | Hilgers et al. |
| 2003/0135198 A1 | 7/2003 | Berhow et al. |
| 2003/0135232 A1 | 7/2003 | Douk et al. |
| 2003/0153942 A1 | 8/2003 | Wang et al. |
| 2003/0186203 A1 | 10/2003 | Aboud |
| 2003/0191492 A1 | 10/2003 | Gellman et al. |
| 2003/0212304 A1 | 11/2003 | Lattouf |
| 2003/0212384 A1 | 11/2003 | Hayden |
| 2003/0233038 A1 | 12/2003 | Hassett |
| 2004/0006344 A1 | 1/2004 | Nguyen et al. |
| 2004/0006365 A1 | 1/2004 | Brady et al. |
| 2004/0015151 A1 | 1/2004 | Chambers |
| 2004/0019322 A1 | 1/2004 | Hoffmann |
| 2004/0059243 A1 | 3/2004 | Flores et al. |
| 2004/0116878 A1 | 6/2004 | Byrd et al. |
| 2004/0122360 A1 | 6/2004 | Waldhauser et al. |
| 2004/0133232 A1 | 7/2004 | Rosenbluth et al. |
| 2004/0138608 A1 | 7/2004 | Barbut et al. |
| 2004/0153049 A1 | 8/2004 | Hewitt et al. |
| 2004/0153118 A1 | 8/2004 | Clubb et al. |
| 2004/0193177 A1 | 9/2004 | Houghton et al. |
| 2004/0210194 A1 | 10/2004 | Bonnette et al. |
| 2004/0220611 A1 | 11/2004 | Ogle |
| 2004/0236215 A1 | 11/2004 | Mihara et al. |
| 2004/0243102 A1 | 12/2004 | Berg et al. |
| 2004/0254602 A1 | 12/2004 | Lehe et al. |
| 2005/0004523 A1 | 1/2005 | Osborne et al. |
| 2005/0004553 A1 | 1/2005 | Douk |
| 2005/0021075 A1 | 1/2005 | Bonnette et al. |
| 2005/0021152 A1 | 1/2005 | Ogle et al. |
| 2005/0027236 A1 | 2/2005 | Douk |
| 2005/0049574 A1 | 3/2005 | Petrick et al. |
| 2005/0059957 A1 | 3/2005 | Campbell et al. |
| 2005/0065467 A1 | 3/2005 | Pudelko et al. |
| 2005/0065498 A1 | 3/2005 | McFerran |
| 2005/0085847 A1 | 4/2005 | Galdonik et al. |
| 2005/0090802 A1 | 4/2005 | Connors et al. |
| 2005/0103332 A1 | 5/2005 | Gingles et al. |
| 2005/0131453 A1 | 6/2005 | Parodi |
| 2005/0154344 A1 | 7/2005 | Chang |
| 2005/0154349 A1 | 7/2005 | Renz et al. |
| 2005/0182386 A1 | 8/2005 | Aggerholm |
| 2005/0209559 A1 | 9/2005 | Thornton et al. |
| 2005/0209631 A1 | 9/2005 | Galdonik et al. |
| 2005/0209675 A1 | 9/2005 | Ton et al. |
| 2005/0228479 A1 | 10/2005 | Pavcnik et al. |
| 2005/0273051 A1 | 12/2005 | Coppi |
| 2005/0277976 A1 | 12/2005 | Galdonik et al. |
| 2006/0020165 A1 | 1/2006 | Adams |
| 2006/0030835 A1 | 2/2006 | Sherman et al. |
| 2006/0030876 A1 | 2/2006 | Peacock et al. |
| 2006/0047301 A1 | 3/2006 | Ogle |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064036 A1 | 3/2006 | Osborne et al. |
| 2006/0079787 A1 | 4/2006 | Whiting et al. |
| 2006/0089618 A1 | 4/2006 | McFerran et al. |
| 2006/0095062 A1 | 5/2006 | Stephens |
| 2006/0100530 A1 | 5/2006 | Kliot et al. |
| 2006/0129091 A1 | 6/2006 | Bonnette et al. |
| 2006/0135961 A1 | 6/2006 | Rosenman et al. |
| 2006/0173440 A1 | 8/2006 | Lamson et al. |
| 2006/0195137 A1 | 8/2006 | Sepetka et al. |
| 2006/0200047 A1 | 9/2006 | Galdonik et al. |
| 2006/0200191 A1 | 9/2006 | Zadno-Azizi |
| 2006/0247755 A1 | 11/2006 | Pal et al. |
| 2006/0258987 A1 | 11/2006 | Lentz et al. |
| 2006/0264759 A1 | 11/2006 | Moehring et al. |
| 2006/0271098 A1 | 11/2006 | Peacock |
| 2007/0016132 A1 | 1/2007 | Oepen et al. |
| 2007/0021778 A1 | 1/2007 | Carly |
| 2007/0043333 A1 | 2/2007 | Kampa et al. |
| 2007/0060888 A1 | 3/2007 | Goff et al. |
| 2007/0060908 A1 | 3/2007 | Webster et al. |
| 2007/0060911 A1 | 3/2007 | Webster et al. |
| 2007/0060944 A1 | 3/2007 | Boldenow et al. |
| 2007/0073264 A1 | 3/2007 | Stedman et al. |
| 2007/0106211 A1 | 5/2007 | Provost-Tine et al. |
| 2007/0135733 A1 | 6/2007 | Soukup et al. |
| 2007/0173784 A1 | 7/2007 | Johansson et al. |
| 2007/0185501 A1 | 8/2007 | Martin et al. |
| 2007/0185522 A1 | 8/2007 | Davies et al. |
| 2007/0197956 A1 | 8/2007 | Le et al. |
| 2007/0198028 A1 | 8/2007 | Miloslavski et al. |
| 2007/0198049 A1 | 8/2007 | Barbut |
| 2007/0208302 A1 | 9/2007 | Webster et al. |

(56) References Cited

U.S. PATENT DOCUMENTS

| | | |
|---|---|---|
| 2007/0227543 A1 | 10/2007 | Peichel |
| 2007/0250040 A1 | 10/2007 | Provost et al. |
| 2007/0250096 A1 | 10/2007 | Yamane et al. |
| 2007/0260115 A1 | 11/2007 | Brock et al. |
| 2007/0260219 A1 | 11/2007 | Root et al. |
| 2008/0027379 A1 | 1/2008 | Wilkins |
| 2008/0082107 A1 | 4/2008 | Miller et al. |
| 2008/0082109 A1 | 4/2008 | Moll et al. |
| 2008/0086110 A1 | 4/2008 | Galdonik et al. |
| 2008/0097251 A1 | 4/2008 | Babaev |
| 2008/0109088 A1 | 5/2008 | Galdonik et al. |
| 2008/0140010 A1 | 6/2008 | Kennedy et al. |
| 2008/0167678 A1 | 7/2008 | Morsi |
| 2008/0172066 A9 | 7/2008 | Galdonik et al. |
| 2008/0177245 A1 | 7/2008 | Mesallum |
| 2008/0183128 A1 | 7/2008 | Morriss et al. |
| 2008/0200946 A1 | 8/2008 | Braun et al. |
| 2008/0243222 A1 | 10/2008 | Schafersman et al. |
| 2008/0262350 A1 | 10/2008 | Unger |
| 2008/0262472 A1 | 10/2008 | Lunn et al. |
| 2008/0294111 A1 | 11/2008 | Tai et al. |
| 2008/0312639 A1 | 12/2008 | Weber |
| 2009/0018455 A1 | 1/2009 | Chang |
| 2009/0018525 A1 | 1/2009 | Waite et al. |
| 2009/0024072 A1 | 1/2009 | Criado et al. |
| 2009/0024089 A1 | 1/2009 | Levine et al. |
| 2009/0030400 A1 | 1/2009 | Bose et al. |
| 2009/0082800 A1 | 3/2009 | Janardhan |
| 2009/0124956 A1 | 5/2009 | Swetlin et al. |
| 2009/0165881 A1 | 7/2009 | Tegg et al. |
| 2009/0198172 A1 | 8/2009 | Garrison et al. |
| 2009/0209857 A1 | 8/2009 | Secretain et al. |
| 2009/0227992 A1 | 9/2009 | Nir et al. |
| 2009/0234321 A1 | 9/2009 | Shapland et al. |
| 2009/0240236 A1 | 9/2009 | Fogarty |
| 2009/0254166 A1 | 10/2009 | Chou et al. |
| 2009/0264865 A1 | 10/2009 | Kawai |
| 2009/0270800 A1 | 10/2009 | Spurchise et al. |
| 2009/0299393 A1 | 12/2009 | Martin et al. |
| 2009/0312699 A1 | 12/2009 | Pudelko et al. |
| 2010/0004607 A1 | 1/2010 | Wilson et al. |
| 2010/0022948 A1 | 1/2010 | Wilson et al. |
| 2010/0030141 A1 | 2/2010 | Chermoni |
| 2010/0030186 A1 | 2/2010 | Stivland |
| 2010/0042118 A1 | 2/2010 | Garrison et al. |
| 2010/0049168 A1 | 2/2010 | Parker et al. |
| 2010/0057051 A1 | 3/2010 | Howat et al. |
| 2010/0063479 A1 | 3/2010 | Merdan et al. |
| 2010/0063480 A1 | 3/2010 | Shireman |
| 2010/0094330 A1 | 4/2010 | Barbut |
| 2010/0114017 A1 | 5/2010 | Lenker et al. |
| 2010/0145308 A1 | 6/2010 | Layman et al. |
| 2010/0185216 A1 | 7/2010 | Garrison et al. |
| 2010/0204672 A1 | 8/2010 | Lockhart et al. |
| 2010/0204684 A1 | 8/2010 | Garrison et al. |
| 2010/0211050 A1 | 8/2010 | Luther |
| 2010/0217235 A1 | 8/2010 | Thorstenson et al. |
| 2010/0217276 A1 | 8/2010 | Garrison et al. |
| 2010/0228269 A1 | 9/2010 | Garrison et al. |
| 2010/0256600 A1 | 10/2010 | Ferrera |
| 2010/0312141 A1 | 12/2010 | Keast et al. |
| 2010/0318097 A1 | 12/2010 | Ferrera et al. |
| 2011/0009875 A1 | 1/2011 | Grandfield et al. |
| 2011/0015482 A1 | 1/2011 | Carrillo, Jr. |
| 2011/0034986 A1 | 2/2011 | Chou et al. |
| 2011/0082373 A1 | 4/2011 | Gurley et al. |
| 2011/0087147 A1 | 4/2011 | Garrison et al. |
| 2011/0106200 A1 | 5/2011 | Ziegler |
| 2011/0112567 A1 | 5/2011 | Lenker et al. |
| 2011/0125181 A1 | 5/2011 | Brady et al. |
| 2011/0152760 A1 | 6/2011 | Parker |
| 2011/0172678 A1 | 7/2011 | Behl et al. |
| 2011/0172700 A1 | 7/2011 | Bose et al. |
| 2011/0230859 A1 | 9/2011 | Galdonik et al. |
| 2011/0238041 A1 | 9/2011 | Lim et al. |
| 2011/0264133 A1 | 10/2011 | Hanlon et al. |
| 2012/0040858 A1 | 2/2012 | Ford et al. |
| 2012/0065479 A1 | 3/2012 | Lahiji et al. |
| 2012/0065490 A1 | 3/2012 | Zharov et al. |
| 2012/0071856 A1 | 3/2012 | Goldfarb et al. |
| 2012/0078140 A1 | 3/2012 | Nita |
| 2012/0095485 A1 | 4/2012 | Cully et al. |
| 2012/0101561 A1 | 4/2012 | Porter |
| 2012/0109044 A1 | 5/2012 | Santamore et al. |
| 2012/0116350 A1 | 5/2012 | Strauss et al. |
| 2012/0123466 A1 | 5/2012 | Porter et al. |
| 2012/0150147 A1 | 6/2012 | Leynov et al. |
| 2012/0253313 A1 | 10/2012 | Galdonik et al. |
| 2012/0271281 A1 | 10/2012 | Schertiger |
| 2012/0310212 A1 | 12/2012 | Fischell et al. |
| 2012/0330196 A1 | 12/2012 | Nita |
| 2013/0006225 A1 | 1/2013 | Cucin |
| 2013/0018318 A1 | 1/2013 | Ravichandran et al. |
| 2013/0035628 A1 | 2/2013 | Garrison et al. |
| 2013/0046285 A1 | 2/2013 | Griffin et al. |
| 2013/0053792 A1 | 2/2013 | Fischell et al. |
| 2013/0116701 A1 | 5/2013 | Wang et al. |
| 2013/0158507 A1 | 6/2013 | Brown |
| 2013/0158578 A1 | 6/2013 | Ghodke et al. |
| 2013/0184735 A1 | 7/2013 | Fischell et al. |
| 2013/0197621 A1 | 8/2013 | Ryan et al. |
| 2013/0274783 A1 | 10/2013 | Wynberg |
| 2013/0281788 A1 | 10/2013 | Garrison |
| 2014/0018773 A1 | 1/2014 | Wang et al. |
| 2014/0025004 A1 | 1/2014 | Falk et al. |
| 2014/0025043 A1 | 1/2014 | Wang et al. |
| 2014/0039461 A1 | 2/2014 | Anderson et al. |
| 2014/0088510 A1 | 3/2014 | Nimkar et al. |
| 2014/0114287 A1 | 4/2014 | Beasley et al. |
| 2014/0155783 A1 | 6/2014 | Starksen et al. |
| 2014/0155908 A1* | 6/2014 | Rosenbluth .......... A61B 17/221 606/127 |
| 2014/0155932 A1 | 6/2014 | Weishaupt et al. |
| 2014/0207043 A1 | 7/2014 | Anand et al. |
| 2014/0228808 A1 | 8/2014 | Webster et al. |
| 2014/0249508 A1 | 9/2014 | Wang et al. |
| 2014/0257186 A1 | 9/2014 | Kerr |
| 2014/0273920 A1 | 9/2014 | Smith |
| 2014/0276618 A1 | 9/2014 | Di Caprio et al. |
| 2014/0276920 A1 | 9/2014 | Hendrick et al. |
| 2014/0276923 A1 | 9/2014 | Miller |
| 2014/0288525 A1 | 9/2014 | Fudaba et al. |
| 2014/0296769 A1 | 10/2014 | Hyde et al. |
| 2014/0296868 A1 | 10/2014 | Garrison et al. |
| 2014/0296889 A1 | 10/2014 | Avneri et al. |
| 2014/0343537 A1 | 11/2014 | Eversull et al. |
| 2014/0358123 A1 | 12/2014 | Ueda et al. |
| 2014/0358178 A1 | 12/2014 | Hewitt et al. |
| 2014/0371709 A1 | 12/2014 | Allen et al. |
| 2015/0025562 A1 | 1/2015 | Dinh et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0151090 A1 | 6/2015 | Sutton et al. |
| 2015/0165160 A1 | 6/2015 | Thungana et al. |
| 2015/0173782 A1 | 6/2015 | Garrison et al. |
| 2015/0174363 A1 | 6/2015 | Sutermeister et al. |
| 2015/0174368 A1 | 6/2015 | Garrison et al. |
| 2015/0245848 A1 | 9/2015 | Shimon |
| 2015/0265802 A1 | 9/2015 | Fukuoka et al. |
| 2015/0282821 A1 | 10/2015 | Look et al. |
| 2015/0327843 A1 | 11/2015 | Garrison |
| 2015/0327919 A1 | 11/2015 | Clopp et al. |
| 2015/0335857 A1 | 11/2015 | Ishikawa |
| 2015/0352330 A1 | 12/2015 | Wasdyke et al. |
| 2016/0008025 A1 | 1/2016 | Gupta et al. |
| 2016/0008572 A1 | 1/2016 | Di Caprio et al. |
| 2016/0015935 A1 | 1/2016 | Chan et al. |
| 2016/0022964 A1 | 1/2016 | Goyal |
| 2016/0058459 A1 | 3/2016 | Bowman |
| 2016/0066931 A1 | 3/2016 | Kugler et al. |
| 2016/0081825 A1 | 3/2016 | Sudin et al. |
| 2016/0100819 A1 | 4/2016 | Tieu |

(56) References Cited

U.S. PATENT DOCUMENTS

| | | |
|---|---|---|
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0144157 A1 | 5/2016 | Gulachenski et al. |
| 2016/0166265 A1 | 6/2016 | Nita |
| 2016/0166266 A1 | 6/2016 | Nita |
| 2016/0199204 A1 | 7/2016 | Pung et al. |
| 2016/0199620 A1 | 7/2016 | Pokorney et al. |
| 2016/0206322 A1 | 7/2016 | Fitz et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317288 A1 | 11/2016 | Rogers et al. |
| 2016/0345904 A1 | 12/2016 | Bowman |
| 2016/0346502 A1 | 12/2016 | Fuller et al. |
| 2016/0346508 A1 | 12/2016 | Williams et al. |
| 2016/0346509 A1 | 12/2016 | Anderson et al. |
| 2016/0361180 A1 | 12/2016 | Vong et al. |
| 2016/0361459 A1 | 12/2016 | Baldwin |
| 2016/0367272 A1 | 12/2016 | Garrison et al. |
| 2016/0367274 A1 | 12/2016 | Wallace |
| 2016/0367275 A1 | 12/2016 | Wallace |
| 2017/0000977 A1 | 1/2017 | Storbeck et al. |
| 2017/0007264 A1 | 1/2017 | Cruise et al. |
| 2017/0007277 A1 | 1/2017 | Drapeau et al. |
| 2017/0020540 A1* | 1/2017 | Chou ................. A61M 25/01 |
| 2017/0027604 A1 | 2/2017 | Wallace |
| 2017/0028170 A1 | 2/2017 | Ho |
| 2017/0035436 A1 | 2/2017 | Morita |
| 2017/0035446 A1 | 2/2017 | Rapaport et al. |
| 2017/0042548 A1 | 2/2017 | Lam |
| 2017/0056061 A1 | 3/2017 | Ogle et al. |
| 2017/0072163 A1 | 3/2017 | Lim et al. |
| 2017/0072165 A1 | 3/2017 | Lim et al. |
| 2017/0072452 A1 | 3/2017 | Monett et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0231647 A1 | 8/2017 | Saunders et al. |
| 2017/0238950 A1 | 8/2017 | Yang et al. |
| 2017/0238951 A1 | 8/2017 | Yang et al. |
| 2017/0238953 A1 | 8/2017 | Yang et al. |
| 2017/0239440 A1 | 8/2017 | Yang et al. |
| 2017/0239441 A1 | 8/2017 | Yang et al. |
| 2017/0239447 A1 | 8/2017 | Yang et al. |
| 2017/0246014 A1 | 8/2017 | Rapaport et al. |
| 2017/0252043 A1 | 9/2017 | Fuller et al. |
| 2017/0252536 A1 | 9/2017 | Yang et al. |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0333060 A1 | 11/2017 | Panian |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou et al. |
| 2017/0367713 A1 | 12/2017 | Greene, Jr. et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Panian |
| 2018/0015254 A1 | 1/2018 | Cragg et al. |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0055516 A1 | 3/2018 | Baldwin et al. |
| 2018/0064453 A1 | 3/2018 | Garrison et al. |
| 2018/0116684 A1 | 5/2018 | Garrison et al. |
| 2018/0133436 A1 | 5/2018 | Garrison et al. |
| 2018/0193042 A1 | 7/2018 | Wilson et al. |
| 2018/0207399 A1 | 7/2018 | Chou et al. |
| 2018/0242978 A1 | 8/2018 | Chou et al. |
| 2018/0339130 A1 | 11/2018 | Ogle |
| 2018/0361114 A1 | 12/2018 | Chou et al. |
| 2019/0008534 A1 | 1/2019 | Garrison et al. |
| 2019/0046218 A1 | 2/2019 | Garrison et al. |
| 2019/0351182 A1 | 11/2019 | Chou et al. |
| 2019/0366042 A1 | 12/2019 | Garrison et al. |
| 2019/0366043 A1 | 12/2019 | Garrison et al. |
| 2020/0016369 A1 | 1/2020 | Garrison et al. |
| 2020/0023160 A1 | 1/2020 | Chou et al. |
| 2020/0038628 A1 | 2/2020 | Chou et al. |
| 2020/0046939 A1 | 2/2020 | Garrison et al. |
| 2020/0046940 A1 | 2/2020 | Garrison et al. |
| 2020/0060722 A1 | 2/2020 | O'Connell et al. |
| 2020/0164178 A1 | 5/2020 | Garrison et al. |
| 2020/0187965 A1 | 6/2020 | Garrison et al. |
| 2020/0215306 A1 | 7/2020 | Garrison et al. |
| 2020/0253670 A1 | 8/2020 | Doisneau et al. |
| 2020/0289136 A1 | 9/2020 | Chou |
| 2020/0337716 A1 | 10/2020 | Garrison et al. |
| 2020/0345981 A1 | 11/2020 | Garrison et al. |
| 2021/0212707 A1 | 7/2021 | Chou et al. |
| 2021/0330332 A1 | 10/2021 | Chou et al. |
| 2021/0338256 A1 | 11/2021 | Chou et al. |
| 2022/0047285 A1 | 2/2022 | Chou et al. |

FOREIGN PATENT DOCUMENTS

| | | |
|---|---|---|
| CN | 103260689 A | 8/2013 |
| CN | 103648574 A | 3/2014 |
| CN | 104394785 A | 3/2015 |
| CN | 104739486 A | 7/2015 |
| CN | 105920720 A | 9/2016 |
| CN | 106039526 A | 10/2016 |
| DE | 102006039236 A1 | 2/2008 |
| EP | 117940 A2 | 9/1984 |
| EP | 0427429 A2 | 5/1991 |
| EP | 1226795 A2 | 7/2002 |
| EP | 1440663 A1 | 7/2004 |
| EP | 1639951 A1 | 3/2006 |
| EP | 2069528 B1 | 3/2013 |
| GB | 2020557 A | 11/1979 |
| JP | 3026200 U | 7/1996 |
| JP | H11-146883 A | 6/1999 |
| JP | 2002291756 A | 10/2002 |
| JP | 2008517652 A | 5/2008 |
| JP | 2014-138756 A | 7/2014 |
| WO | WO-93/17750 A1 | 9/1993 |
| WO | WO-94/02194 A1 | 2/1994 |
| WO | WO-95/05209 A1 | 2/1995 |
| WO | WO-98/38930 A1 | 9/1998 |
| WO | WO-00/16705 A1 | 3/2000 |

(56) References Cited

FOREIGN PATENT DOCUMENTS

| | | |
|---|---|---|
| WO | WO-00/32266 A1 | 6/2000 |
| WO | WO-00/76390 A2 | 12/2000 |
| WO | WO-01/15767 A1 | 3/2001 |
| WO | WO-01/58365 A1 | 8/2001 |
| WO | WO-02/32495 A1 | 4/2002 |
| WO | WO-02/055146 A1 | 7/2002 |
| WO | WO-02/085092 A2 | 10/2002 |
| WO | WO-03/018085 A2 | 3/2003 |
| WO | WO-03/090831 A2 | 11/2003 |
| WO | WO-2004/006803 A1 | 1/2004 |
| WO | WO-2005/051206 A1 | 6/2005 |
| WO | WO-2006/111944 A1 | 10/2006 |
| WO | WO-2006/127929 A2 | 11/2006 |
| WO | WO-2006/132434 A1 | 12/2006 |
| WO | WO-2008/144587 A2 | 11/2008 |
| WO | WO-2009/012473 A3 | 1/2009 |
| WO | WO-2009/099764 A1 | 8/2009 |
| WO | WO-2009/100210 A1 | 8/2009 |
| WO | WO-2010/075445 A1 | 7/2010 |
| WO | WO-2010/075565 A2 | 7/2010 |
| WO | WO-2012/047803 A2 | 4/2012 |
| WO | WO-2014/203336 A1 | 12/2014 |
| WO | WO-2015/100178 A1 | 7/2015 |
| WO | WO-2015/157330 A1 | 10/2015 |
| WO | WO-2020/061240 A1 | 3/2020 |
| WO | WO-2020/132003 A1 | 6/2020 |

OTHER PUBLICATIONS

"Asahi Fubuki Catheter Dilator Kit." Asahi-Intecc USA Medical. 2017. Web. Accessed Oct. 2, 2017. 3 pages, www.asahi-inteccusa-medical.com/medical-product/fubuki-dilator-kit/. Accessed Oct. 2, 2017.

Farooq, Vasim et al. "Forward and Back Aspiration during ST-Elevation Myocardial Infarction: a Feasibility Study." EuroIntervention, vol. 11, No. 14, 2016, pp. 1639-1648.

Farooq, Vasim et al. "The Use of A Guide Catheter Extension System as an Aid During Transradial Percutaneous Coronary Intervention of Coronary Artery Bypass Grafts." *Catheterization and Cardiovascular Interventions*, vol. 78, No. 6, 2011, pp. 847-863.

Feldman, "Transcatheter Aspiration of a Thrombus in an Aortocoronary Saphenous Vein Graft," *American Journal of Cardiology*, 60(4):379-380 (1987).

Guidezilla Guide Extension Catheter, Boston Scientific 510k Submission, Feb. 19, 2013, 5 pages. Web. Accessed Oct. 23, 2017.

Heart and Stroke Foundation of Canada. "Vacuum cleaner sucks up strokes." *ScienceDaily*, Jun. 8, 2010, 4 pages, www.sciencedaily.com/releases/2010/06/100608162240.htm.

Hopf-Jensen, S. (Nov. 2016, e-published Jul. 1, 2016) "Impact and Effectiveness of Dual Aspiration Technique in Stent-Assisted Mechanical Thrombectomy: Recent Improvements in Acute Stroke Management," *Cardiovasc Intervent Radiol*, 39:1620-1628.

Kopeck, Rachel. "Penumbra, Inc. Launches 5MAX™ ACE—The Newest Clot Extraction Device to Treat Acute Ischemic Stroke Patients." *Penumbra Inc.*, Jul. 8, 2013, 3 pages, http://www.penumbrainc.com/news/penumbra-inc-launches-5max-ace-the-newest-clot-extraction-device-to-treat-acute-ischemic-stroke-patients/.

Merit Medical Systems Acquired Distal Access's SPINR Platform, Jul. 15, 2015, Digital Access, LLC; Merit Medical Systems, 5 pages. Web. Accessed Oct. 23, 2017.

Patel, Tejas et al. (2014) "Balloon-Assisted Tracking: A Must-Know Technique to Overcome Difficult Anatomy During Transradial Approach," *Catheter Cardiovasc. Interv.*, 83(2):211-220.

Pena, Carlos. "Letter to Sequent Medical Inc Re: K150894, Trade/Device Name: VIA™ 21 Microcatheter." Department of Health & Human Services, Aug. 28, 2015, 14 pages.

Penumbra, Inc., "Penumbra, Inc. Completes Pivotal Stroke Trial of Intracranial Revascularization," Press Release, (2007). Web. Accessed Jun. 14, 2017. 2 pages.

Penumbra, Inc., "The Penumbra Pivotal Stroke Trial: Safety and Effectiveness of a New Generation of Mechanical Devices for Clot Removal in Intracranial Large Vessel Occlusive Disease," *Stroke* 2009, 40:2761-2768. Web. Downloaded Jun. 15, 2017.

Reeder et al., "Aspiration Thrombectomy for Removal of Coronary Thrombus," American Journal of Cardiology. (Jul. 1, 1992) 70:107-110 (Abstract only).

Simon et al., Exploring the efficacy of cyclic vs. static aspiration in a cerebral thrombectomy model: an initial proof of concept study, J. Neuro Intervent Surg 2014, 6, pp. 677-683. Web. Downloaded Oct. 18, 2017.

Simon et al., Hydrodynamic comparison of the Penumbra system and commonly available syringes in forced-suction thrombectomy, J. Neuro Intervent Surg 2014, 6, pp. 205-211. Web. Downloaded Oct. 18, 2017.

Spiotta et al., Evolution of thrombectomy approaches and devices for acute stroke: a technical review, J. Neuro Intervent Surg 2015, 7, pp. 2-7. Web. Downloaded Oct. 18, 2017.

Stys, Adam T. et al. "A Novel Application of GuideLiner Catheter for Thrombectomy in Acute Myocardial Infarction: A Case Series." *Journal of Invasive Cardiology*, vol. 25, No. 11, 2013, pp. E254-59. 6 pages, (http://www.invasivecardiology.com/issue/4284).

Turk, Aquilla S, et al. (2014) "Initial clinical experience with the ADAPT technique: A direct aspiration first pass technique for stroke thrombectomy." *J NeuroIntervent Surg* 2014;6:231-237. doi:10.1136/neurintsurg-2013-010713. Web. Accessed Sep. 26, 2018.

Vijaywargiya et al "Anatomical study of petrous and cavernous parts of internal carotid artery". Anatomy and Cell Biology 2017;50: 163-170. (Year: 2017).

Webb et al., "Retrieval and Analysis of Particulate Debris After Saphenous Vein Graft Intervention," *Journal of the American College of Cardiology*, 34(2);468-475 (1999).

Yoo et al., "The Penumbra Stroke System: a technical review." *Journal of NeuroInterventional Surgery*. 4:199-205 (2012). Web. Downloaded Jun. 15, 2017.

Zuckerman, Bram. "Letter to Cathera Inc: Re K151638, Trade/Device Name: Phenom™ Catheters." Department of Health & Human Services, Nov. 13, 2015, 6 pages.

Arslanian, R., M. Gounis, and J. Chueh. "Pump or Syringe? Evaluation of Aspiration Efficacy with Neurovascular Catheters," (Oral Presentation, SNIS 2018), 2 pages. Web. Date accessed Feb. 10, 2020.

Kayan, Y. and J. Delgado, "Neurointerventional Treatment of Acute Stroke in 2015 at Abbott Northwestern Hospital," (Nov. 16, 2015). (https://www.slideshare.net/AllinaHealth/neurointerventional-treatment-of-acute-stroke-in-2015-at-abbott-northwestern-hospital).

Spinnaker® Elite™ Flow Directed Catheters Go with the Flow. Indications for Use. 2 page. Web. Aug. 27, 2019.

Spinnaker® Elite™ Flow Directed Catheters Go *with the Flow*. Promotional Brochure. 1 page. Web. Aug. 27, 2019.

Vuong, S. M. et al. (2017). "Application of emerging technologies to improve access to ischemic stroke care." Neurosurgical Focus, 42(4), E8. 7 pages. https://doi.org/10.3171/2017.1.FOCUS16520.

Seidel, A. et al. (2005). "Relationship between the diameter of great saphenous vein and body mass index," J Vasc Bras, vol. 4, No. 3, p. 265-269.

Paullus WS, Pait TG, Rhoton AI Jr. Microsurgical exposure of the petrous portion of the carotid artery. J Neurosurg. 1977;47(5):713-726. (Year: 1977).

\* cited by examiner

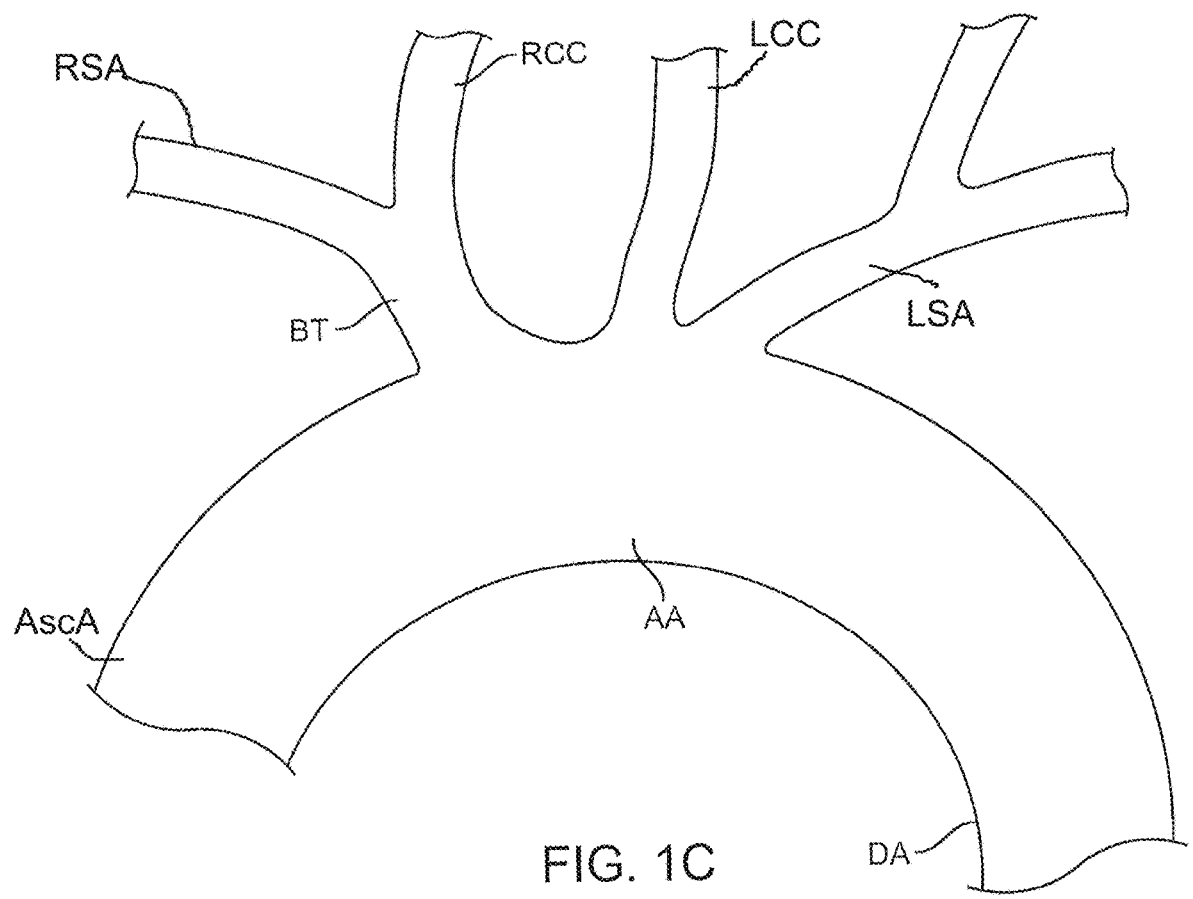

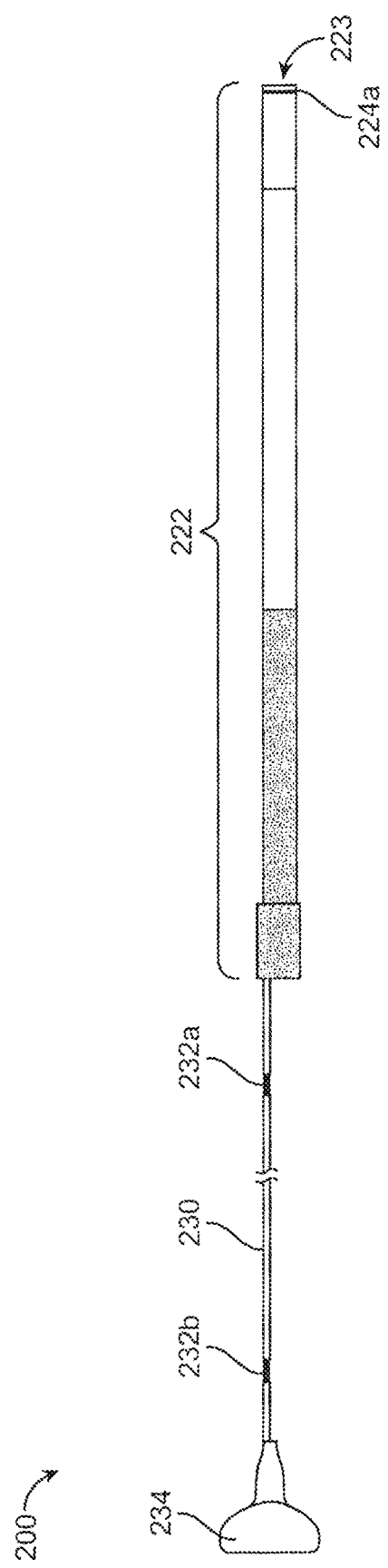

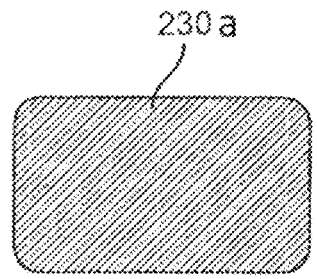
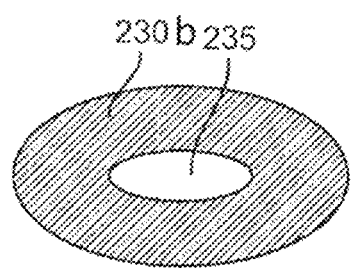
FIG. 4A          FIG. 4B
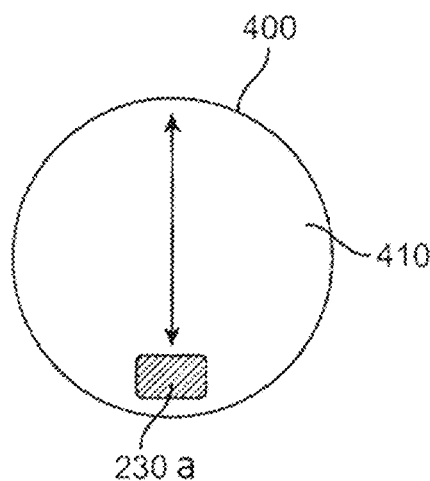
FIG. 4C
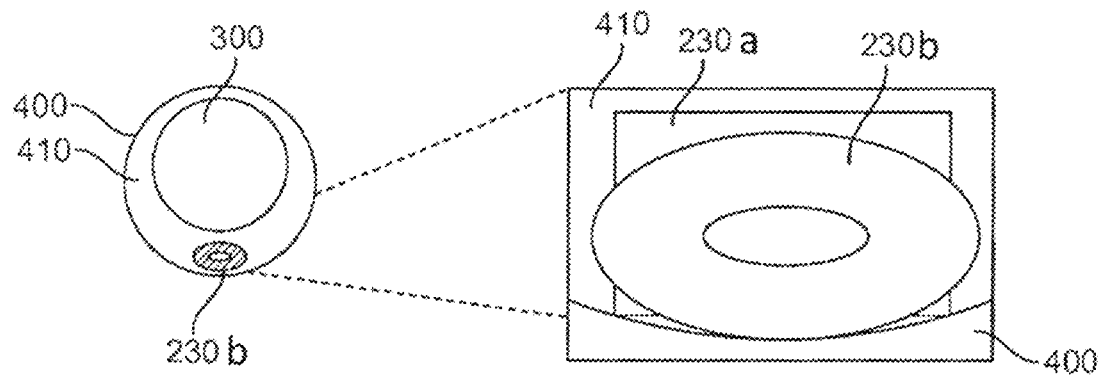
FIG. 4D          FIG. 4E

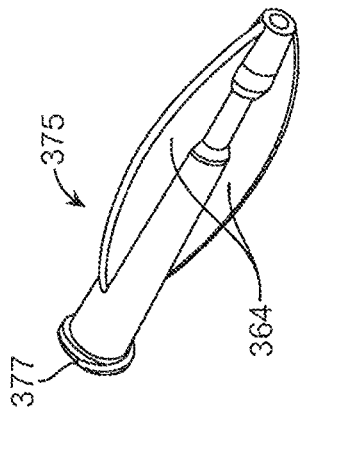
FIG. 7H
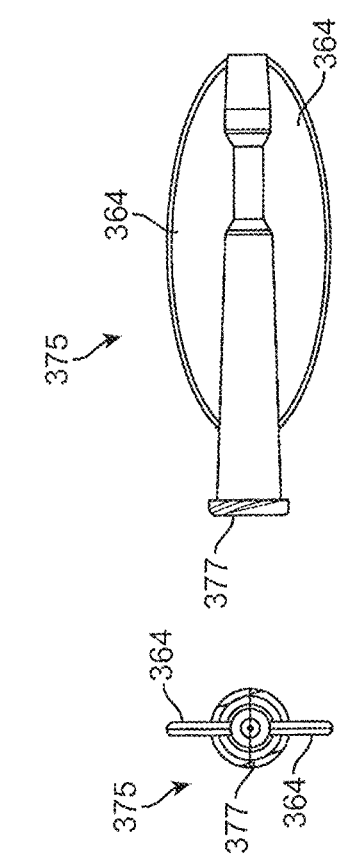
FIG. 7G
FIG. 7F
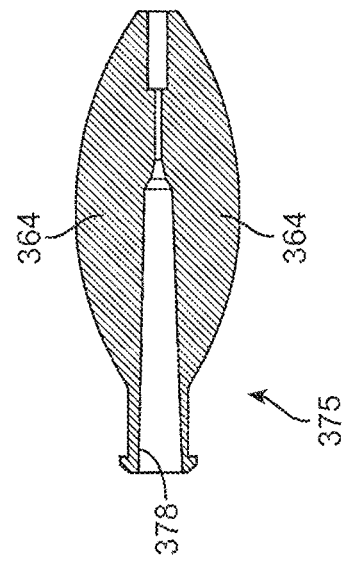
FIG. 7J
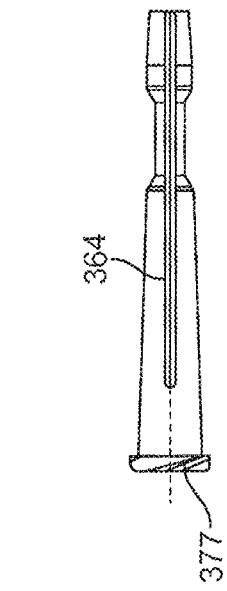
FIG. 7I

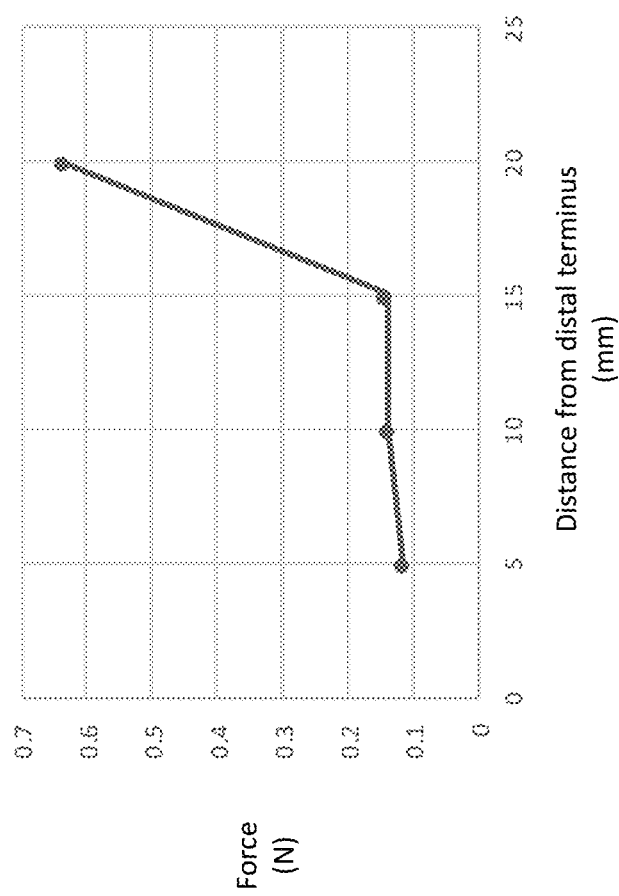

ASPIRATION CATHETER SYSTEMS AND METHODS OF USE

CROSS-REFERENCE TO RELATED APPLICATIONS

The present application claims the benefit of priority under 35 U.S.C. § 119(e) to U.S. Provisional Patent Application Ser. No. 62/673,009, filed May 17, 2018. The disclosure of the provisional application is hereby incorporated by reference in its entirety.

FIELD

The present technology relates generally to medical devices and methods, and more particularly, to aspiration catheter systems and their methods of use.

BACKGROUND

Acute ischemic stroke (AIS) usually occurs when an artery to the brain is occluded, preventing delivery of fresh oxygenated blood from the heart and lungs to the brain. These occlusions are typically caused by a thrombus or an embolus lodging in the artery and blocking the artery that feeds a territory of brain tissue. If an artery is blocked, ischemia injury follows, and brain cells may stop working. Furthermore, if the artery remains blocked for more than a few minutes, the brain cells may die, leading to permanent neurological deficit or death. Therefore, immediate treatment is critical.

Two principal therapies are employed for treating ischemic stroke: thrombolytic therapy and endovascular treatment. The most common treatment used to reestablish flow or re-perfuse the stroke territory is the use of intravenous (IV) thrombolytic therapy. The timeframe to enact thrombolytic therapy is within 3 hours of symptom onset for IV infusion (4.5 hours in selected patients) or within 6 hours for site-directed intra-arterial infusion. Instituting therapy at later times has no proven benefit and may expose the patient to greater risk of bleeding due to the thrombolytic effect. Endovascular treatment most commonly uses a set of tools to mechanically remove the embolus, with our without the use of thrombolytic therapy.

The gamut of endovascular treatments include mechanical embolectomy, which utilizes a retrievable structure, e.g., a coil-tipped retrievable stent (also known as a stent retriever or a STENTRIEVER), a woven wire stent, or a laser cut stent with struts that can be opened within a clot in the cerebral anatomy to engage the clot with the stent struts, create a channel in the emboli to restore a certain amount of blood flow, and to subsequently retrieve the retrievable structure by pulling it out of the anatomy, along with aspiration techniques. Other endovascular techniques to mechanically remove AIS-associated embolus include Manual Aspiration Thrombectomy (MAT) (also known as the "ADAPT" technique). ADAPT/MAT is an endovascular procedure where large bore catheters are inserted through the transfemoral artery and maneuvered through complex anatomy to the level of the embolus, which may be in the extracranial carotids, vertebral arteries, or intracranial arteries. Aspiration techniques may be used to remove the embolus through the large bore catheters. Another endovascular procedure is STENTRIEVER-Mediated Manual Aspiration Thrombectomy (SMAT) (similar to the STENTRIEVER-assisted "Solumbra" technique). SMAT, like MAT, involves accessing the embolus through the transfemoral artery. After access is achieved, however, a retrievable structure is utilized to pull the embolus back into a large bore catheter.

To access the cerebral anatomy, guide catheters or guide sheaths are used to guide interventional devices to the target anatomy from an arterial access site, typically the femoral artery. The length of the guide is determined by the distance between the access site and the desired location of the guide distal tip. Interventional devices such as guidewires, microcatheters, and intermediate catheters used for sub-selective guides and aspiration, are inserted through the guide and advanced to the target site. Often, devices are used in a co-axial fashion, namely, a guidewire inside a microcatheter inside an intermediate catheter is advanced as an assembly to the target site in a stepwise fashion with the inner, most atraumatic elements, advancing distally first and providing support for advancement of the outer elements. The length of each element of the coaxial assemblage takes into account the length of the guide, the length of proximal connectors on the catheters, and the length needed to extend from the distal end.

Typical tri-axial systems such as for aspiration or delivery of stent retrievers and other interventional devices require overlapped series of catheters, each with their own rotating hemostatic valves (RHV) on the proximal end. For example, a guidewire can be inserted through a Penumbra Velocity microcatheter having a first proximal RHV, which can be inserted through a Penumbra ACE68 having a second proximal RHV, which can be inserted through a Penumbra NeuronMAX 088 access catheter having a third proximal RHV positioned in the high carotid via a femoral introducer. Maintaining the coaxial relationships between these catheters can be technically challenging. The three RHVs must be constantly adjusted with two hands or, more commonly, four hands (i.e. two operators). Further, the working area of typical tri-axial systems for aspiration and/or intracranial device delivery can require working area of 3-5 feet at the base of the operating table.

The time required to access the site of the occlusion and restore, even partially, flow to the vessel is crucial in determining a successful outcome of such procedures. Similarly, the occurrence of distal emboli during the procedure and the potentially negative neurologic effect and procedural complications such as perforation and intracerebral hemorrhage are limits to success of the procedure. There is a need for a system of devices and methods that allow for rapid access, optimized catheter aspiration and treatment to fully restore flow to the blocked cerebral vessel.

SUMMARY

In an aspect described is a coaxial catheter system including a catheter and a catheter advancement element. The catheter includes a distal, catheter portion having a lumen and a distal end having an opening from the lumen, the lumen having an inner diameter at the distal end of at least about 0.052"; and a proximal extension coupled to and extending proximally from the distal, catheter portion, the proximal extension being less flexible than the distal, catheter portion. The catheter advancement element includes a tubular portion having an inner diameter that is at least about 0.014" up to about 0.024" and an outer diameter having at least one snug point. A difference between the inner diameter of the distal, catheter portion and the outer diameter of the tubular portion at such snug point is no more than about 0.010". The catheter advancement element includes a proximal extension coupled to and extending proximally from the tubular portion, the proximal extension being less flexible than the tubular portion; and a tip portion located distal to the at least one snug point of the tubular portion. The tip portion has a length and tapers along at least a portion of the length of the tip portion. The coaxial catheter system has an advancement configuration characterized by the catheter advancement element positioned coaxially within the lumen of the distal catheter portion, the at least one snug point of the tubular portion is substantially aligned with the distal end of the distal catheter portion. The advancement configuration is also characterized by the tip portion in the advancement configuration has at least three points spaced along the length of the tip portion. The at least three points include a distal point of the at least three points located a distance proximal from the distal-most end of the catheter advancement element, the distal point having a first bending force that is no greater than about 0.05 Newtons; an intermediate point of the at least three points located a distance proximal from the distal point, the intermediate point having a second bending force; and a proximal point of the at least three points located a distance proximal from the intermediate point, the proximal point having a third bending force. The advancement configuration is also characterized by the coaxial system having at least two system points along a length of the coaxial system. The at least two system points include a first system point of the at least two system points located proximal to the distal end of the catheter portion, the first system point having a first system bending force; and a second system point of the at least two system points located distal to the first system point by a distance that is at least about 1 mm distal to the distal end of the catheter portion, wherein the second system point can be the same or different from the proximal point, the second system point having a second system bending force.

A difference between the second bending force and the first bending force divided by the distance between the distal point and the intermediate point can equal a first flexibility slope. A difference between the third bending force and the second bending force divided by a distance between the intermediate point and the proximal point can equal a second flexibility slope. An average of the first flexibility slope and the second flexibility slope can define an average tip portion flexibility slope. A difference between the first system bending force and the second system bending force divided by the distance between the first system point and the second system point can equal a third flexibility slope. A ratio of the third flexibility slope to the average tip portion flexibility slope can be less than about 25.

The proximal extension of the catheter advancement element can have at least one stiffness point located within about 125 cm from the distal-most end of the catheter advancement element, the at least one stiffness point has a bending force. A ratio of the bending force of the at least one stiffness point to the first bending force of the distal point can be at least about 100. The proximal extension of the catheter advancement element can have at least one stiffness point located within about 125 cm from the distal-most end of the catheter advancement element, the at least one stiffness point has a bending force, wherein a ratio of the bending force of the at least one stiffness point to the first bending force of the distal point is at least about 200. The proximal extension of the catheter advancement element can have at least one stiffness point located within about 125 cm from the distal-most end of the catheter advancement element, the at least one stiffness point has a bending force. A ratio of the bending force of the at least one stiffness point to the first bending force of the distal point can be greater than at least about 300. The length of the tip portion can be at least about 1 cm up to about 4 cm. A ratio of the third bending force of the proximal point to the first bending force of the distal point can be at least 2. A ratio of the first system bending force to the first bending force of the distal point can be at least 2. The distal, catheter portion can have a catheter point located a distance of at least 5 mm proximal from the distal end, the catheter point having a catheter bending force. The first bending force of the distal point can be about 5%-15% the catheter bending force. The third bending force of the proximal point can be about 50%-90% the catheter bending force. A difference between the first bending force at the distal point to the third bending force at the proximal point can be a function of wall thickness. The inner diameter at the distal end of the distal, catheter portion can be about 0.054" and the difference at the snug point can be about 0.006" to about 0.008". The inner diameter at the distal end of the distal, catheter portion can be about 0.070" up to about 0.088" and the difference at the snug point can be no more than about 0.006" to about 0.008".

The tubular portion of the catheter advancement element can have a radiopaque marker band embedded within or positioned over a wall of the tubular portion, the radiopaque marker band positioned at the snug point. The radiopaque marker band can have a proximal edge, a distal edge, and a width between the proximal edge and the distal edge. When in the advancement configuration, the proximal edge of the radiopaque marker band can align substantially with the distal end of the distal, catheter portion such that the radiopaque marker band remains external to the lumen of the distal, catheter portion. The outer diameter of the tubular portion can have a length that is at least about 5 cm up to about 10 cm. The snug point can be located along at least a portion of the length. The outer diameter can be substantially uniform along the length. The outer diameter can be substantially non-uniform along the length. The distal point can be located a distance of at least 5 mm proximal from the distal-most end of the catheter advancement element. The first system point can be located at least about 5 mm proximal to the distal end of the catheter portion.

In an interrelated aspect, described is a coaxial catheter system including a catheter and a catheter advancement element. The catheter includes a distal, catheter portion having a lumen and a distal end having an opening from the lumen, the lumen having an inner diameter at the distal end of at least about 0.052". The catheter includes a proximal extension coupled to and extending proximally from the distal, catheter portion, the proximal extension being less flexible than the distal, catheter portion. The catheter advancement element includes a tubular portion having an inner diameter that is at least about 0.014" up to about 0.024", an outer diameter. The outer diameter has at least one snug point. A difference between the inner diameter of the distal, catheter portion and the outer diameter of the tubular portion at the snug point is no more than about 0.010". The catheter advancement element includes a tip portion located distal to the at least one snug point of the tubular portion. The tip portion has a length and tapers along at least a portion of the length of the tip portion. The tip portion has a distal point located a distance of at least 5 mm proximal from the distal-most end of the catheter advancement element, the distal point having a bending force that is no greater than about 0.05 Newtons.

In an interrelated aspect, described is a method of performing a medical procedure in a cerebral vessel of a patient. The method includes advancing a first assembled coaxial system of devices toward an occlusion within a cerebral blood vessel. The first assembled coaxial system of device includes a first catheter having a first catheter portion having a lumen, a proximal opening into the lumen, a distal opening from the lumen, and a distal end. A first proximal extension is coupled to and extending proximally from the first catheter portion, the first proximal extension being less flexible than the first catheter portion. The first assembled coaxial system of device includes a first delivery element having a flexible, elongate body and a soft, tapered distal tip portion. At least a portion of the elongate body positioned within the lumen of the first catheter portion and the tapered distal tip portion extending distal to the distal end of the first catheter portion. The method includes withdrawing the first delivery element proximally from the lumen of the first catheter portion and advancing a second assembled coaxial system of devices through the lumen of the first catheter portion, out the distal opening from the lumen, and to a location near a proximal face of the occlusion within the cerebral blood vessel. The second assembled coaxial system of devices includes a second catheter and a second delivery element. The second catheter includes a second catheter portion having a lumen, a proximal opening into the lumen, a distal opening from the lumen, and a distal end; and a second proximal extension coupled to and extending proximally from the second catheter portion, the second proximal extension being less flexible than the second catheter portion. The second delivery element includes a flexible, elongate body and a soft, tapered distal tip portion, at least a portion of the elongate body positioned within the lumen of the second catheter portion and the tapered distal tip portion extending distal to the distal end of the second catheter portion. The second assembled coaxial system of devices is advanced together after the distal end of the second catheter portion is distal to the petrous portion of the internal carotid artery. The method includes withdrawing the second delivery element proximally from the lumen of the second catheter portion; applying aspiration pressure through the lumen of the second catheter portion; anchoring the distal end of the second catheter portion onto the occlusion via the aspiration pressure; and applying a proximally-directed force on the second catheter to reduce slack in the second catheter relative to surrounding anatomy while the distal end of the second catheter portion remains anchored onto the occlusion.

The method can further include withdrawing the second catheter from the cerebral blood vessel, the distal end of the second catheter portion has attached occlusive material. The method can further include advancing the first catheter over the second catheter while anchoring the distal end of the second catheter portion onto the occlusion via the aspiration pressure. The method can further include positioning the distal end of the first catheter portion near the proximal face of the occlusion. The method can further include withdrawing the second catheter into the lumen of the first catheter; and automatically applying aspiration pressure through the lumen of the first catheter portion upon withdrawal of the second catheter into the lumen. The aspiration pressure applied through the lumen of the first catheter portion and the lumen of the second catheter portion can be applied from a single source of aspiration. The distal end of the second catheter portion can be attached occlusive material.

The method can further include withdrawing the second catheter from the lumen of the first catheter while the first catheter maintains the aspiration pressure through the lumen of the first catheter portion. The method can further include advancing a guide sheath from an access location, wherein the guide sheath comprises a tubular sheath body having a central lumen, a proximal end, a distal opening, and a connector operably connected with the proximal end of the sheath body. Advancing the first assembled coaxial catheter system can include advancing the first assembled coaxial catheter system through the guide sheath. The first catheter portion can have an outer diameter configured to seal with the central lumen of the guide sheath upon application of the aspiration pressure. The second catheter portion can have an outer diameter configured to seal with the lumen of the first catheter upon application of the aspiration pressure. An outer surface of the second catheter portion can seal with an inner surface of the first catheter portion forming a contiguous lumen between the distal opening of the second catheter portion to the proximal end of the guide sheath. The connector can include a single or two-headed rotating hemostatic valve. Both the first and second assembled coaxial catheter systems can be advanced through the connector. The method can further include advancing the guide sheath comprises advancing the distal opening of the guide sheath to a location in a distal internal carotid artery (ICA). The second catheter can have an inner diameter that is between 0.054" and 0.070", the first catheter has an inner diameter between 0.072" and 0.088", and the guide sheath is between 6 Fr to 8 Fr. The method can further include advancing a guidewire across the occlusion. The occlusion need not be penetrated during the method. The first assembled coaxial catheter system can further include a guidewire. When assembled, the guidewire can be positioned within a lumen of the flexible, elongate body of the first delivery element and the first delivery element can be positioned within the lumen of the first catheter portion such that the tapered distal tip portion extends distal to the distal end of the first catheter portion and the guidewire extends distal to the tapered distal tip portion. An outer surface of the second catheter portion can seal with an inner surface of the first catheter portion forming a contiguous lumen between the distal opening of the second catheter portion and the proximal opening of the first catheter portion.

In an interrelated aspect, described is a method of performing a medical procedure in a cerebral vessel of a patient. The method includes advancing a first assembled coaxial catheter system to a location near a proximal face of an occlusion within a cerebral blood vessel. The first assembled coaxial catheter system includes a first catheter and a first delivery element. The first catheter includes a first catheter portion having a lumen, a proximal opening into the lumen, a distal opening from the lumen, and a distal end; and a first proximal extension coupled to and extending proximally from the first catheter portion, the first proximal extension being less flexible than the first catheter portion. The first delivery element includes a flexible, elongate body and a soft, tapered distal tip portion, at least a portion of the elongate body positioned within the lumen of the first catheter portion and the tapered distal tip portion extending distal to the distal end of the first catheter portion. The first assembled coaxial system of devices is advanced together after the distal end of the first catheter portion is distal to the petrous portion of the internal carotid artery. The method includes withdrawing the first delivery element proximally from the lumen of the first catheter portion; applying aspiration pressure through the lumen of the first catheter portion; anchoring the distal end of the first catheter portion onto the occlusion via the aspiration pressure; applying a proximally-directed force on the first catheter to reduce slack in the first catheter relative to surrounding anatomy while the distal end of the first catheter remains anchored onto the occlusion; and advancing a second catheter over the first catheter while anchoring the distal end of the first catheter portion onto the occlusion via the aspiration pressure. The second catheter includes a second catheter portion having a lumen, a proximal opening into the lumen, a distal opening from the lumen, and a distal end; and a second proximal extension coupled to and extending proximally from the second catheter portion. The second proximal extension is less flexible than the second catheter portion.

The method can further include withdrawing the first catheter from the cerebral blood vessel. The distal end of the first catheter portion may have attached occlusive material. The method can further include positioning the distal end of the second catheter portion near the proximal face of the occlusion. The method can further include withdrawing the first catheter into the lumen of the second catheter; and automatically applying aspiration pressure through the lumen of the second catheter portion upon withdrawal of the first catheter into the lumen. The aspiration pressure can be applied through the lumen of the first catheter portion and the lumen of the second catheter portion is applied from a single source of aspiration. The distal end of the first catheter can have attached occlusive material. The method can further include withdrawing the first catheter from the lumen of the second catheter while the second catheter maintains the aspiration pressure through the lumen of the second catheter portion. The method can further include advancing a guide sheath from an access location. The guide sheath can include a tubular sheath body having a central lumen, a proximal end, a distal opening, and a connector operably connected with the proximal end of the sheath body. The second catheter portion can include an outer diameter configured to seal with the central lumen of the guide sheath upon application of the aspiration pressure. The first catheter portion can have an outer diameter configured to seal with the lumen of the second catheter upon application of the aspiration pressure. An outer surface of the first catheter portion can seal with an inner surface of the second catheter portion forming a contiguous lumen between the distal opening of the first catheter portion to the proximal end of the guide sheath. The connector can include a single or two-headed rotating hemostatic valve. Both the first assembled coaxial catheter system and the second catheter can be advanced through the connector.

The method can include advancing the guide sheath comprises advancing the distal opening of the guide sheath to a location in a distal internal carotid artery (ICA). The first catheter can have an inner diameter between 0.054" and 0.070". The second catheter can have an inner diameter between 0.072" and 0.088". The guide sheath can be between 6 Fr to 8 Fr. The method can further include advancing a guidewire across the occlusion. The occlusion need not be penetrated during the method. An inner surface of the second catheter portion can seal with an outer surface of the first catheter portion forming a contiguous aspiration lumen between the distal opening of the first catheter portion and the proximal opening of the second catheter portion.

In an interrelated aspect, disclosed is a system of devices for performing a medical procedure in a cerebral vessel of a patient including a first catheter and a second catheter. The first catheter includes a first catheter portion having a lumen, a proximal opening into the lumen, a distal opening from the lumen, and a distal end; and a first proximal extension coupled to and extending proximally from the first catheter portion, the first proximal extension being less flexible than the first catheter portion. The second catheter is configured to be coaxially disposed within the lumen of the first catheter portion. The second catheter includes a second catheter portion having a lumen, a proximal opening into the lumen, a distal opening from the lumen, and a distal end; and a second proximal extension coupled to and extending proximally from the second catheter portion, the second proximal extension being less flexible than the second catheter portion. The system includes a guide sheath having a tubular sheath body with a central lumen, a proximal end, a distal opening, and a connector operably connected with the proximal end of the sheath body. A single, shared vacuum source is coupled to the connector of the guide sheath and configured to apply aspiration pressure through the central lumen of the guide sheath, the lumen of the first catheter portion, and the lumen of the second catheter portion. An outer surface of the second catheter portion can seal with an inner surface of the first catheter portion forming a contiguous lumen between the distal opening of the first catheter portion and the proximal opening of the second catheter portion.

In an interrelated aspect, disclosed is a method of performing a medical procedure in a cerebral vessel of a patient. The method includes advancing a first catheter towards an occlusion within a cerebral blood vessel. The first catheter includes a first catheter portion having a lumen, a proximal opening into the lumen, a distal opening from the lumen, and a distal end; and a first proximal extension coupled to the first catheter portion near the proximal opening, the first proximal extension being less flexible than the first catheter portion. The method includes advancing a second catheter through the lumen of the first catheter portion, out the distal opening from the lumen, and to a location near a proximal face of the occlusion within the cerebral blood vessel. The second catheter includes a second catheter portion having a lumen, a proximal opening into the lumen, a distal opening from the lumen, and a distal end; and a second proximal extension coupled to the second catheter portion near the proximal opening, the second proximal extension being less flexible than the second catheter portion. The method includes forming a seal between an outer diameter of the second catheter portion and an inner diameter of the first catheter portion; and applying aspiration pressure through at least one of the lumen of the second catheter portion, the lumen of the first catheter portion, or a contiguous aspiration lumen formed by the lumens of the first and second catheter portions. The contiguous aspiration lumen extends from the distal end of the second catheter portion towards the proximal opening of the first catheter portion. The method can further include anchoring the distal end of the second catheter portion onto the occlusion via the aspiration pressure. The method can further include applying a proximally-directed force on the second catheter to reduce slack in the second catheter relative to surrounding anatomy while the distal end of the second catheter portion remains anchored onto the occlusion.

In some variations, one or more of the following can optionally be included in any feasible combination in the above methods, apparatus, devices, and system. More details of the methods, apparatus, devices, and systems are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively, but are intended to be illustrative. Also, relative placement of features and elements may be modified for the purpose of illustrative clarity.

FIG. 1C illustrates the aortic arch including the take-offs of the brachiocephalic BT, left common carotid LCC, and left subclavian arteries LSA from the aortic arch AA;

FIG. 3 is a side view of an implementation of a spined distal access catheter;

FIG. 4A is a cross-sectional view of first implementation of a proximal control element of a spined distal access catheter;

FIG. 4B is a cross-sectional view of another implementation of a proximal control element of a spined distal access catheter;

FIG. 4C is a cross-sectional view of the proximal control element of FIG. 4A within a working lumen of an access sheath;

FIG. 4D is a cross-sectional view of the proximal control element of FIG. 4B within a working lumen of an access sheath having a catheter advancement element extending therethrough;

FIG. 4E is a cross-sectional, schematic view comparing the surface area of the proximal control element of FIG. 4A and the proximal control element of FIG. 4B within the working lumen of an access sheath of FIG. 4D;

FIGS. 7F-7J are various views of an implementation of a proximal hub for coupling to the proximal portion shown in FIG. 7E;

FIG. 14E is a graph of the bending forces along a length of another catheter system;

Figure 1A:
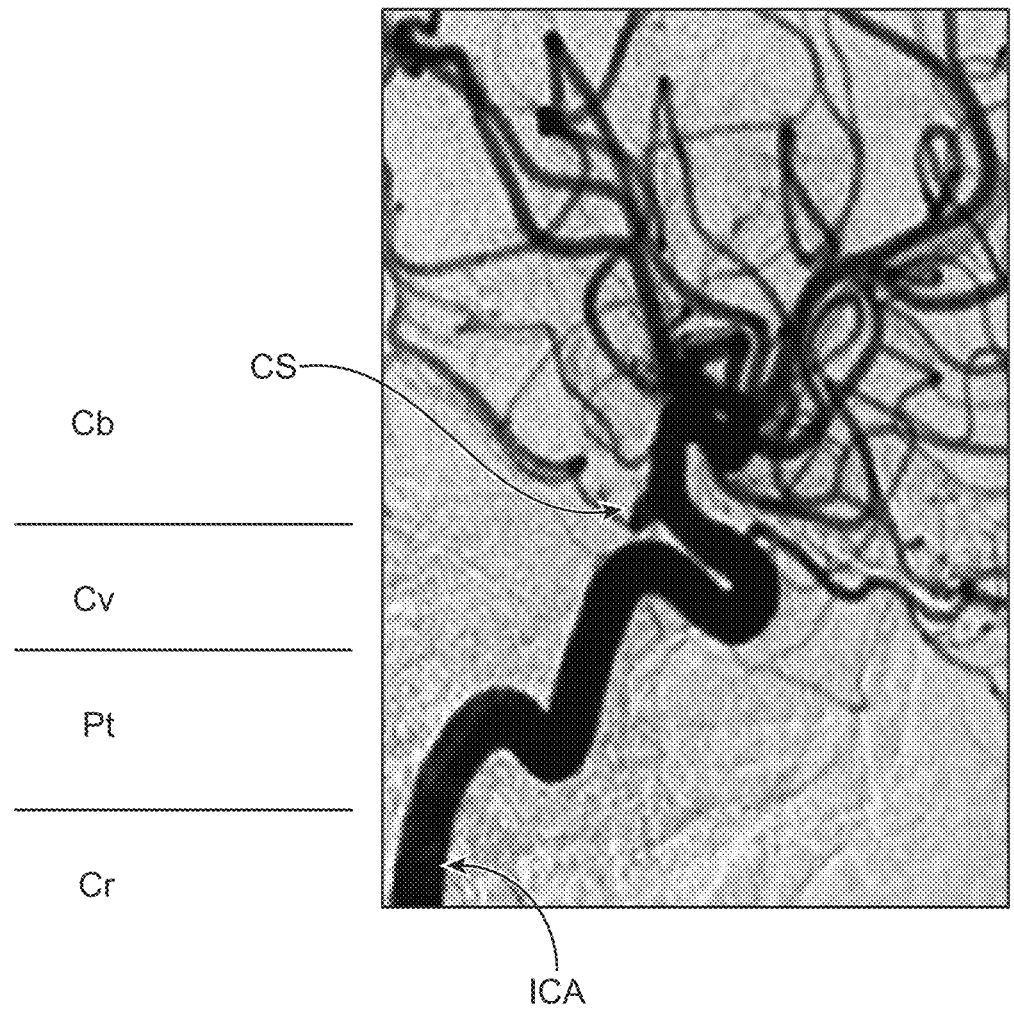
FIGS. 1A-1B illustrate the course of the terminal internal carotid artery through to the cerebral vasculature.

It should be appreciated that the drawings are for example only and are not meant to be to scale. It is to be understood that devices described herein may include features not necessarily depicted in each figure.

DETAILED DESCRIPTION

Navigating the carotid anatomy in order to treat various neurovascular pathologies at the level of the cerebral arteries, such as acute ischemic stroke (AIS), requires catheter systems having superior flexibility and deliverability. The internal carotid artery (ICA) arises from the bifurcation of the common carotid artery (CCA) at the level of the intervertebral disc between C3 and C4 vertebrae. As shown in FIG.

1A, the course of the ICA is divided into four parts—cervical Cr, petrous Pt, cavernous Cv and cerebral Cb parts. In the anterior circulation, the consistent tortuous terminal carotid is locked into its position by bony elements. The cervical carotid Cr enters the petrous bone and is locked into a set of turns as it is encased in bone. The cavernous carotid is an artery that passes through a venous bed, the cavernous sinus, and while flexible, is locked as it exits the cavernous sinus by another bony element, which surrounds and fixes the entry into the cranial cavity. Because of these bony points of fixation, the petrous and cavernous carotid (Pt and Cv) and above are relatively consistent in their tortuosity. The carotid siphon CS is an S-shaped part of the terminal ICA. The carotid siphon CS begins at the posterior bend of the cavernous ICA and ends at the ICA bifurcation into the anterior cerebral artery ACA and middle cerebral artery MCA. The ophthalmic artery arises from the cerebral ICA, which represents a common point of catheter hang-up in accessing the anterior circulation. The MCA is initially defined by a single M1 segment and then further bifurcates in two or three M2 segments and then further arborizes to create M3 segments. These points of catheter hang-up can significantly increase the amount of time needed to restore blood perfusion to the brain, which in the treatment of AIS is a disadvantage with severe consequences.

With advancing age, the large vessels often enlarge and lengthen. Fixed proximally and distally, the cervical internal carotid artery often becomes tortuous with age. The common carotid artery CCA is relatively fixed in the thoracic cavity as it exits into the cervical area by the clavicle. The external and internal carotid arteries ECA, ICA are not fixed relative to the common carotid artery CCA, and thus they develop tortuosity with advancing age with lengthening of the entire carotid system. This can cause them to elongate and develop kinks and tortuosity or, in worst case, a complete loop or so-called "cervical loop". If catheters used to cross these kinked or curved areas are too stiff or inflexible, these areas can undergo a straightening that can cause the vessel to wrap around or "barbershop pole" causing focused kinking and folding of the vessel. These sorts of extreme tortuosity also can significantly increase the amount of time needed to restore blood perfusion to the brain, particularly in the aging population. In certain circumstances, the twisting of vessels upon themselves or if the untwisted artery is kinked, normal antegrade flow may be reduced to a standstill creating ischemia. Managing the unkinking or unlooping the vessels such as the cervical ICA can also increase the time it takes to perform a procedure.

A major drawback of current catheter systems for stroke intervention procedures is the amount of time required to restore blood perfusion to the brain, including the time it takes to access the occlusive site or sites in the cerebral artery and the time it takes to completely remove the occlusion in the artery. Because it is often the case that more than one attempt must be made to completely remove the occlusion, reducing the number of attempts as well as reducing the time required to exchange devices for additional attempts is an important factor in minimizing the overall time. Additionally, each attempt is associated with potential procedural risk due to device advancement in the delicate cerebral vasculature. Another limitation is the need for multiple operators to deliver and effectively manipulate long tri-axial systems with multiple RHVs typically used with conventional guide and distal access catheters.

Described herein are catheter systems and methods for treating various neurovascular pathologies, such as acute ischemic stroke (AIS). The systems described herein provide quick and simple single-operator access to distal target anatomy, in particular tortuous anatomy of the cerebral vasculature at a single point of manipulation. The medical methods, devices, and systems described herein allow for navigating complex, tortuous anatomy to perform rapid and safe aspiration and removal of cerebral occlusions for the treatment of acute ischemic stroke. The medical methods, devices and systems described herein can also be used to deliver intracranial medical devices, with or without aspiration for the removal of cerebral occlusions in the treatment of acute ischemic stroke. The systems described herein can be particularly useful for the treatment of AIS whether a user intends to perform aspiration alone as a frontline treatment for AIS. Further, the extreme flexibility and deliverability of the distal access catheter systems described herein allow the catheters to take the shape of the tortuous anatomy rather than exert straightening forces creating new anatomy. The distal access catheter systems described herein can pass through tortuous loops while maintaining the natural curves of the anatomy therein decreasing the risk of vessel straightening. The distal access catheter systems described herein can thereby create a safe conduit through the neurovasculature maintaining the natural tortuosity of the anatomy for other catheters to traverse (e.g. larger bore aspiration catheters).

The devices, systems, and methods of use described herein are related to and can be used in combination and in the alternative with the devices, systems, and methods of use described in U.S. Publication No. 2013/0035628, filed Aug. 3, 2012; U.S. Publication No. 2015/0173782, filed Dec. 19, 2014; and U.S. Publication No. 2016/0220741, filed Feb. 4, 2016. The disclosures of each of these publications are incorporated by reference herein in their entireties.

While some implementations are described herein with specific regard to accessing a neurovascular anatomy for application of aspiration, the systems and methods described herein should not be limited to this and may also be applicable to other uses. For example, the catheter systems described herein may be used to deliver working devices to a target vessel of a coronary anatomy or other vasculature anatomy. Where the phrase "distal access catheter" or "aspiration catheter" is used herein that the catheter can be used for aspiration, the delivery of fluids to a treatment site or as a support catheter, or distal access providing a conduit that facilitates and guides the delivery or exchange of other devices such as a guidewire or interventional devices such as stent retrievers. Alternatively, the access systems described herein may also be useful for access to other parts of the body outside the vasculature. Similarly, where the working device is described as being an expandable cerebral treatment device, stent retriever or self-expanding stent other interventional devices can be delivered using the delivery systems described herein.

Figure 2A:
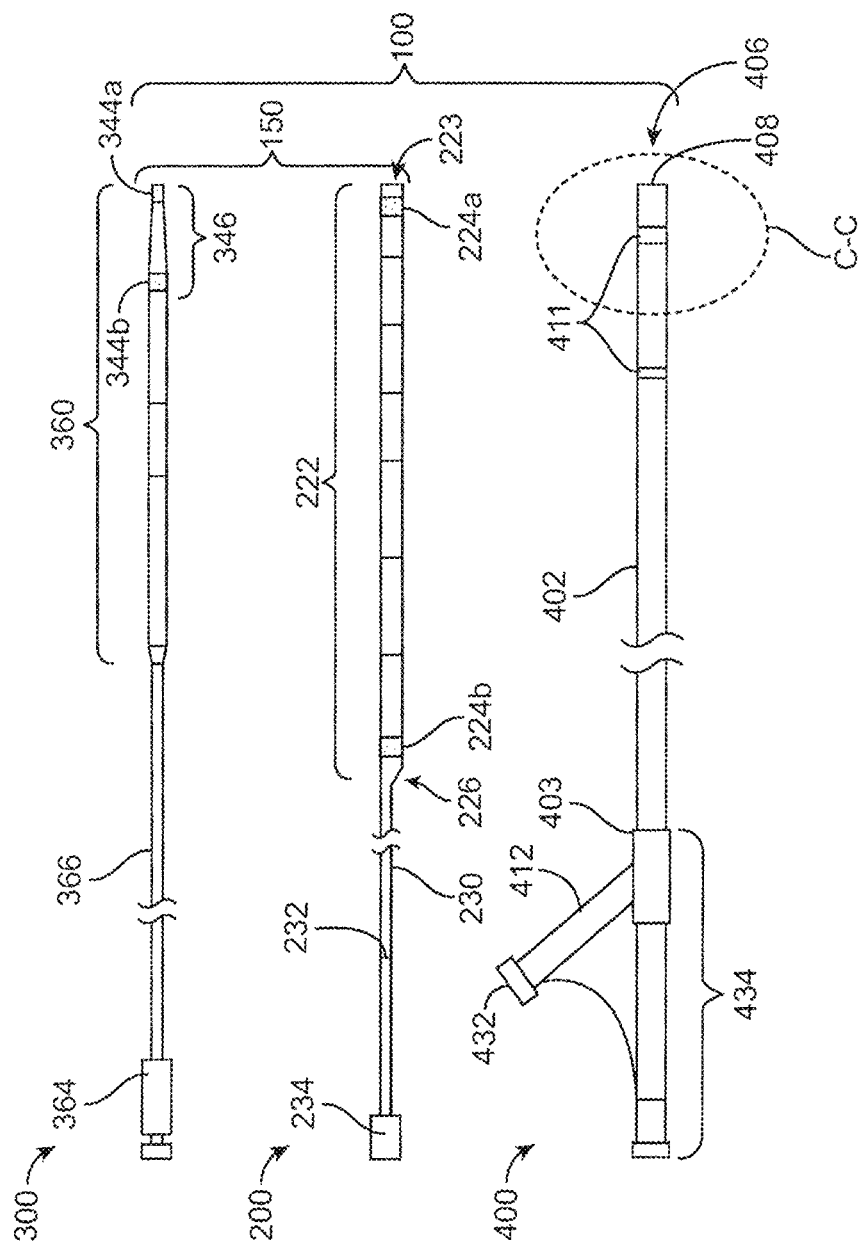
FIG. 2A is an exploded view of an implementation of an aspiration catheter system.
Figure 2B:
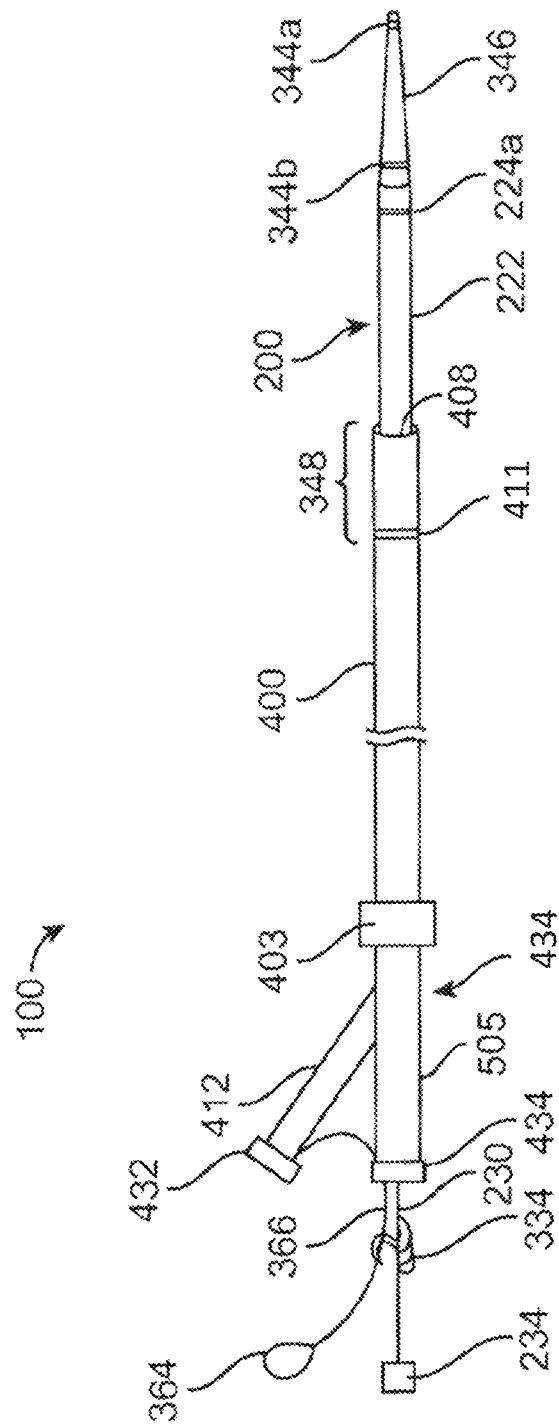
FIG. 2B is an assembled view of the aspiration catheter system of FIG. 2A.

Referring now to the drawings, FIGS. 2A-2B illustrate a system 100 including devices for accessing and removing a cerebral occlusion to treat acute ischemic stroke. The system 100 can be a single operator system such that each of the components and systems can be delivered and used together by one operator through a single point of manipulation requiring minimal hand movements. As will be described in more detail below, all wire and catheter manipulations can occur at or in close proximity to a single rotating hemostatic valve (RHV) 434 or more than a single RHV co-located in the same device. The system 100 can include one or more catheter delivery systems 150, each having a catheter 200 and a catheter advancement element 300. The catheter delivery system 150 is configured to be advanced through an access guide sheath 400. The catheter 200 is configured to be received through the guide sheath 400 and is designed to have exceptional deliverability. The catheter 200 can be a spined, distal access catheter co-axial with a lumen of the guide sheath 400 thereby providing a step-up in inner diameter within the conduit. The catheter 200 can be delivered using a catheter advancement element 300 inserted through a lumen 223 of the catheter 200. The system 100 can be a distal access system that can create a variable length from point of entry at the percutaneous arteriotomy (e.g. the femoral artery or other point of entry) to the target control point of the distal catheter. Conventional distal access systems for stroke intervention typically include a long guide sheath or guide catheter placed through a shorter "introducer" sheath (e.g. 11-30 cm in length) at the groin. The long guide sheath is typically positioned in the ICA to support neurovascular interventions including stroke embolectomy (sometimes referred to as "thrombectomy"). For added support, these can be advanced up to the bony terminal petrous and rarely into the cavernous or clinoid or supraclinoid terminal ICA when possible. To reach targets in the M1 or M2 distribution for ADAPT/MAT or Solumbra/SMAT approaches, an additional catheter may be inserted through the long guide catheter. These catheters are typically large-bore aspiration catheters that can be, for example 130 cm in length or longer. As will be described in more detail below, the distal access systems 100 described herein can be shorter, for example, only 115 cm in length when taken as a system as measured from the access point, typically the common femoral artery. Additionally, the single operator can use the systems described herein by inserting them through a single rotating hemostatic valve (RHV) 434 on the guide sheath 400 or more than one RHV co-located in the same device such as a dual-headed RHV. Thus, what was once a two-person procedure can be a one-person procedure.

Each of the various components of the various systems will now be described in more detail.

Access Guide Sheath

Again with respect to FIGS. 2A-2D, the distal access system 100 can include an access guide sheath 400 having a body 402 through which a working lumen extends from a proximal hemostasis valve 434 coupled to a proximal end region 403 of the body 402 to a distal opening 408 of a distal end region. The working lumen is configured to receive the catheter 200 therethrough such that a distal end of the catheter 200 can extend beyond a distal end of the sheath 400 through the distal opening 408. The guide sheath 400 can be used to deliver the catheters described herein as well as any of a variety of working devices known in the art. For example, the working devices can be configured to provide thrombotic treatments and can include large-bore catheters, aspiration embolectomy (or thrombectomy), advanced catheters, wires, balloons, retrievable structures such as coil-tipped retrievable stents "stent retriever". The guide sheath 400 in combination with the catheter 200 can be used to apply distal aspiration as will be described in more detail below.

The guide sheath 400 can be any of a variety of commercially available guide sheaths. For example, the guide sheath 400 can have an ID between 0.087"-0.089" such as the Cook SHUTTLE 6 F (Cook Medical, Inc., Bloomington, Ind.), Terumo DESTINATION 6 F (Terumo Europe NV), Cordis VISTA BRITE TIP (Cordis Corp., Hialeah, Fla.), and Penumbra NEURON MAX 088 (Penumbra, Inc., Alameda, Calif.), Stryker Infinity (Stryker Neurovascular, Fremont, Calif.) or comparable commercially available guiding sheath. Generally, sheath sizes are described herein using the French (F) scale. For example, where a sheath is described as being 6 French, the inner diameter of that sheath is able to receive a catheter having a 6 F outer diameter, which is about 1.98 mm or 0.078". A catheter may be described herein as having a particular size in French to refer to the compatibility of its inner diameter to receive an outer diameter of another catheter. A catheter may also be described herein as having a particular size in French to refer to its outer diameter being compatible with another catheter having a particular inner diameter.

The guide sheath 400 can be a variety of sizes to accept various working devices, such as catheter 200, and can be accommodated to the operator's preference. The working lumen of the guide sheath 400 can be sized to receive its respective catheter 200 in a sliding fit. Generally, it is desirable to minimize the overall size of the vessel insertion site by limiting the outer diameter of the guide sheath 400 to under 0.122". It is also desirable to select corresponding outer and inner diameters to provide a good sliding fit between the catheter 200 and the guide sheath 400. The working lumen of the guide sheath may have an inner diameter that is at least 0.001" larger than a maximum outer diameter of any catheter 200 it is intended to receive, particularly if the catheter 200 is to be used for aspiration. The working lumen can have an inner diameter sized to accommodate at least 6 French catheters (1.98 mm or 0.078"), or at least 6.3 French catheters (2.079 mm or 0.082" OD), or at least 7 French (2.31 mm or 0.091" OD) catheters or 8 French (2.64 mm or 0.104" OD) or larger catheters. The inner diameter of the guide sheath 400, however, may be smaller or larger to be compatible with other catheter sizes. Regardless of the length and inner diameter, the guide sheath 400 is resistant to kinking during distal advancement through the vessels.

The aspiration catheters described herein can have an ID of between 0.054" to 0.088". If the catheter 200 has an 0.088" inner diameter and have a maximum outer diameter of between 0.105" and 0.107". The guide sheath 400 can, in turn, have a working lumen with an inner diameter that is between 0.106" and 0.108". Generally, the difference or clearance between the maximum outer diameter of the catheter 200 and the inner diameter of the guide sheath 400 is less than about 0.002", for example between 0.001" up to 0.002". The region of low clearance between the maximum outer diameter of the catheter 200 and the inner diameter of the guide sheath 400 can be limited to a localized region. Meaning, the low clearance fit between the two can extend only a fraction of a cylindrical length of the catheter 200 and the sheath 400. Thus, the OD-ID difference between the catheter 200 and the guide sheath 400 can be greater than or equal to 0.002" along a first cylindrical length of where the two devices overlap during use and below 0.002" along a different cylindrical length of the overlap, thereby providing a localized region of low clearance within the overlap. This allows for a convenient relative slidability and sufficient sealing when placed under aspiration pressure as will be described in more detail below. For example, a distal region of the guide sheath 400 can have a first inner diameter at a distal end region and a second, different inner diameter at a proximal end region such that the low clearance of the sliding fit with the catheter 200 varies along its length. In some implementations, the catheter 200 has a first outer diameter at a distal end region and a second, larger outer diameter at a proximal end region. The second, larger outer diameter can be less than 0.002" the inner diameter of the sheath 400 and the first outer diameter greater than 0.002" the inner diameter of the sheath 400. The provides a tighter overall fit between the guide sheath 400 and the proximal end region of the catheter 200 at the location of this second, larger outer diameter.

Again with respect to FIGS. 2A-2D, the sheath body 402 can extend from a proximal furcation or rotating hemostatic valve (RHV) 434 at a proximal end region 403 to a tip 406 at a distal end of the body 402. The proximal RHV 434 may include one or more lumens molded into a connector body to connect to the working lumen of the body 402 of the guide sheath 400. The working lumen can receive the catheter 200 and/or any of a variety of working devices for delivery to a target anatomy. The RHV 434 can be constructed of thick-walled polymer tubing or reinforced polymer tubing. The RHV 434 allows for the introduction of devices through the guide sheath 400 into the vasculature, while preventing or minimizing blood loss and preventing air introduction into the guide sheath 400. The RHV 434 can be integral to the guide sheath 400 or the guide sheath 400 can terminate on a proximal end in a female Luer adaptor to which a separate hemostasis valve component, such as a passive seal valve, a Tuohy-Borst valve or rotating hemostasis valve may be attached. The RHV 434 can have an adjustable opening that is open large enough to allow removal of devices that have adherent clot on the tip without causing the clot to dislodge at the RHV 434 during removal. Alternately, the RHV 434 can be removable such as when a device is being removed from the sheath 400 to prevent clot dislodgement at the RHV 434. The RHV 434 can be a dual RHV.

The RHV 434 can form a Y-connector on the proximal end 403 of the sheath 400 such that the first port of the RHV 434 can be used for insertion of a working catheter into the working lumen of the sheath 400 and a second port into arm 412 can be used for another purpose. For example, a syringe or other device can be connected at arm 412 via a connector 432 to deliver a forward drip, a flush line for contrast or saline injections through the body 402 toward the tip 406 and into the target anatomy. Arm 412 can also connect to an aspiration source 505 (see FIG. 2B). The aspiration source 505 can be an active source of aspiration such as an aspiration pump, a regular or locking syringe, a hand-held aspirator, hospital suction, or the like, configured to draw suction through the working lumen. In an embodiment, the aspiration source 505 is a locking syringe (for example a VacLok Syringe) attached to a flow controller. The plunger on the syringe can be pulled back into a locked position by the user while the connection to the flow line is closed prior to an embolectomy step of the procedure. During the procedure when the tip of the catheter is near or at the face of the occlusion, the user may open the connection to the aspiration syringe. This allows for a maximum communication of aspiration force being applied through the working lumen of the sheath 400 and any catheter extending through the sheath 400 that in turn is in communication with the vessel at its distal end. The aspiration can be applied in a rapid fashion by a single user at the single, shared source. In another implementations, the arm 412 can be connected to an aspiration source 505 that is a pump configured to apply an aspiration pressure through the working lumen of the guide sheath 400. The single, shared source of aspiration is sufficient to draw aspiration through the entire system 100, even when multiple aspiration catheters 200 are nested within one another through the working lumen of the guide sheath 400. The arm 412 can also allow the guide sheath 400 to be flushed with saline or radiopaque contrast during a procedure. The working lumen can extend from a distal end to a working proximal port of the proximal end region 403 of the sheath body 402.

The length of the catheter body 402 is configured to allow the distal tip 406 of the body 402 to be positioned as far distal in the internal carotid artery (ICA), for example, from a transfemoral approach, with additional length providing for adjustments if needed. In some implementations (e.g. femoral or radial percutaneous access), the length of the body 402 can be in the range of 80 to 90 cm or can be longer, for example, up to about 100 cm or up to about 105 cm. In implementations, the body 402 length is suitable for a transcarotid approach to the bifurcation of the carotid artery, in the range of 20-25 cm. In further implementations, the body 402 length is suitable for a percutaneous transcarotid approach to the CCA or proximal ICA, and is in the range of 10-15 cm. The body 402 is configured to assume and navigate the bends of the vasculature without kinking, collapsing, or causing vascular trauma, even, for example, when subjected to high aspiration forces.

In some implementations, the system 100 can further include a select tool for advancing the guide sheath 400. The select tool can have an outer diameter configured to be received within the working lumen of the guide sheath 400 such that a distal end region of the select tool extends a distance distal to the distal end of the guide sheath 400. The outer diameter of the select tool sufficiently fills the inner diameter of the working lumen of the guide sheath 400 to minimize the lip at the distal opening 408 of the guide sheath 400. For example, if the working lumen of the guide sheath 400 has an inner diameter that is between about 0.087" to about 0.113", the outer diameter of the select tool can be about 0.006" less than this, or between about 0.081" to about 0.107". The brachiocephalic take-off (BT) is typically a very severe turn off the aortic arch AA for a transfemorally-delivered catheter seeking the right-sided cerebral circulation (shown in FIG. 1C). A catheter traverses from the femoral artery through the iliac circulation into the descending aorta DA. The catheter turns as it approaches the aortic arch AA and reaches across the take-off of other great vessels to reach the brachiocephalic take-off (BT), which is the furthest "reach" of the great vessels of the aortic arch AA. FIG. 1C shows the substantial and obligatory S-turn created by that anatomy. A catheter must traverse this S-turn along a path of insertion from a femoral artery insertion location in order to reach the internal carotid artery (ICA). The left ICA often takes off from the brachiocephalic and thus, has a similar challenge and can create an even tighter S-turn. Should the left ICA have a typical take-off between the brachiocephalic BT and the left subclavian artery LSA take-off, then the reach may be less severe, but an S-turn still develops of lesser severity. The distal end region of the select tool can be tapered and/or shaped to provide support and guidance to advance the sheath 400 around this turn into the ICA. In some implementations, the select tool can have a Bernstein Select-style or a Simmons-style reverse curve catheter tip as is known in the art.

The tip 406 of the guide sheath 400 can have a same or similar outer diameter as a section of the body 402 leading up to the distal end. Accordingly, the tip 406 may have a distal face orthogonal to a longitudinal axis passing through the body 402 and the distal face may have an outer diameter substantially equal to a cross-sectional outer dimension of the body 402. In an implementation, the tip 406 includes a chamfer, fillet, or taper, making the distal face diameter slightly less than the cross-sectional dimension of the body 402. In a further implementation, the tip 406 may be an elongated tubular portion extending distal to a region of the body 402 having a uniform outer diameter such that the elongated tubular portion has a reduced diameter compared to the uniform outer diameter of the body 402. Thus, the tip 406 can be elongated or can be more bluntly shaped. Accordingly, the tip 406 may be configured to smoothly track through a vasculature and/or to dilate vascular restrictions as it tracks through the vasculature. The working lumen may have a distal end forming a distal opening 408.

The guide sheath 400 may include a tip 406 that tapers from a section of the body 402 leading up to the distal end. That is, an outer surface of the body 402 may have a diameter that reduces from a larger dimension to a smaller dimension at a distal end. For example, the tip 406 can taper from an outer diameter of approximately 0.114" to about 0.035" or from about 0.110" to about 0.035" or from about 0.106" to about 0.035". The angle of the taper of the tip 406 can vary depending on the length of the tapered tip 406. For example, in some implementations, the tip 406 tapers from 0.110" to 0.035" over a length of approximately 50 mm.

In an implementation, the guide sheath 400 includes one or more radiopaque markers 411. The radiopaque markers 411 can be disposed near the distal tip 406. For example, a pair of radiopaque bands may be swaged, painted, embedded, or otherwise disposed in or on the body 402. In some implementations, the radiopaque markers 411 include a barium polymer, tungsten polymer blend, tungsten-filled or platinum-filled marker that maintains flexibility of the distal end of the device and improves transition along the length of the guide sheath 400 and its resistance to kinking. In some implementations, the radiopaque marker 411 is a tungsten-loaded PEBAX or polyurethane that is heat welded to the body 402. The markers 411 are shown in the figures as rings around a circumference of one or more regions of the body 402. However, the markers 411 can have other shapes or create a variety of patterns that provide orientation to an operator regarding the position of the distal opening 408 within the vessel. Accordingly, an operator may visualize a location of the distal opening 408 under fluoroscopy to confirm that the distal opening 408 is directed toward a target anatomy where a catheter 200 is to be delivered. For example, radiopaque marker(s) 411 allow an operator to rotate the body 402 of the guide sheath 400 at an anatomical access point, e.g., a groin of a patient, such that the distal opening provides access to an ICA by subsequent working device(s), e.g., catheters and wires advanced to the ICA. In some implementations, the radiopaque marker(s) 411 include platinum, gold, tantalum, tungsten or any other substance visible under an x-ray fluoroscope. Any of the various components of the systems described herein can incorporate radiopaque markers.

In some implementations, the guide sheath 400 can have performance characteristics similar to other sheaths used in carotid access and AIS procedures in terms of kinkability, radiopacity, column strength, and flexibility. The inner liners can be constructed from a low friction polymer such as PTFE (polytetrafluoroethylene) or FEP (fluorinated ethylene propylene) to provide a smooth surface for the advancement of devices through the inner lumen. An outer jacket material can provide mechanical integrity to the inner liners and can be constructed from materials such as PEBAX, thermoplastic polyurethane, polyethylene, nylon, or the like. The body 402 can include a hydrophilic coating. A third layer can be incorporated that can provide reinforcement between the inner liner and the outer jacket. The reinforcement layer can prevent flattening or kinking of the inner lumen of the body 402 to allow unimpeded device navigation through bends in the vasculature as well as aspiration or reverse flow. The body 402 can be circumferentially reinforced. The reinforcement layer can be made from metal such as stainless steel, Nitinol, Nitinol braid, helical ribbon, helical wire, cut stainless steel, or the like, or stiff polymer such as PEEK. The reinforcement layer can be a structure such as a coil or braid, or tubing that has been laser-cut or machine-cut so as to be flexible. In another implementation, the reinforcement layer can be a cut hypotube such as a Nitinol hypotube or cut rigid polymer, or the like. The outer jacket of the body 402 can be formed of increasingly softer materials towards the distal end. The flexibility of the body 402 can vary over its length, with increasing flexibility towards the distal portion of the body 402. The variability in flexibility may be achieved in various ways. For example, the outer jacket may change in durometer and/or material at various sections. A lower durometer outer jacket material can be used in a distal section of the guide sheath compared to other sections of the guide sheath. Alternately, the wall thickness of the jacket material may be reduced, and/or the density of the reinforcement layer may be varied to increase the flexibility. For example, the pitch of the coil or braid may be stretched out, or the cut pattern in the tubing may be varied to be more flexible. Alternately, the reinforcement structure or the materials may change over the length of the sheath body 402. In another implementation, there is a transition section between the distal-most flexible section and the proximal section, with one or more sections of varying flexibilities between the distal-most section and the remainder of the sheath body 402. In this implementation, the distal-most section is about 2 cm to about 5 cm, the transition section is about 2 cm to about 10 cm and the proximal section takes up the remainder of the sheath length. In some implementations, the proximal region of the body 402 can be formed of a material such as Nylon, a region of the body 402 distal to the proximal region of the body 402 can have a material hardness of 72 D whereas areas more distal can be increasingly more flexible and formed of materials having a material hardness of 55 D, 45 D, 35 D extending towards the distal tip 406, which can be formed of a material having a material hardness of 35 D, for example.

The working lumen of the guide sheath 400 can have different inner diameters configured to receive different outer diameter catheters 200. In some implementations, the working lumen of a first guide sheath 400 can have an inner diameter sized to receive a 6 F catheter and the working lumen of a second guide sheath 400 can have an inner diameter sized to receive a 8 F catheter. The guide sheaths 400 can receive catheters having an outer diameter along at least a length that is snug to the inner diameter dimension of the guide sheath 400. The guide sheath 400 (as well as any of the variety of components used in combination with the sheath 400) can be an over-the-wire (OTW) or rapid exchange type device, which will be described in more detail below.

The sheath 400 can include a body 402 formed of generally three layers, including a lubricious inner liner, a reinforcement layer, and an outer jacket layer. The reinforcement layer can include a braid to provide good torqueability optionally overlaid by a coil to provide good kink resistance. In sheaths where the reinforcement layer is a braid alone, the polymers of the outer jacket layer can be generally higher durometer and thicker to avoid issues with kinking. The wall thickness of such sheaths that are braid alone with thicker polymer can be about 0.011". The wall thickness of the sheaths 400 described herein having a braid with a coil overlay provide both torqueability and kink resistance and can have a generally thinner wall, for example, a wall thickness of about 0.0085". The proximal end outer diameter can thereby be reduced to less than 0.112", for example, about 0.107" outer diameter. It is generally beneficial to limit the overall OD of the guide sheath 400 such that the entry wound into the patient (e.g. at the femoral artery) can be kept to a minimum size. Thus, the sheath 400 is a high performance sheath 400 that has good torque and kink resistance with a thinner wall providing an overall lower profile to the system. The thinner wall and lower profile allows for a smaller insertion hole through the vessel without impacting overall lumen size. In some implementations, the wall thickness of the guide sheath 400 can slowly step down to be thinner towards a distal end of the sheath compared to a proximal end.

The system can include localized points of low clearance between the guide sheath 400 and the catheter 200 extending through it. The localized points of low clearance can provide localized sealing between the structures. In some implementations, the localized sealing can be near the distal end region of the guide sheath 400 and in others the localized sealing can be a distance away from the distal end of the guide sheath 400. The catheter 200 can have an increase in OD near a proximal end region creating a cylindrical region of the catheter that forms a snug fit (e.g. less than about 0.002" clearance) with the ID of the guide sheath 400. The length of this low clearance sealing region can vary and depend on the overall clearance between the ID and OD. Greater differences in ID/OD (i.e. higher clearance) can provide sufficient sealing at aspirational pressures by increasing the length of the cylindrical sealing region. Smaller differences in ID/OD (i.e. lower clearance) can provide sufficient sealing at aspirational pressures while having a shorter cylindrical length. In other words, a shorter sealing zone may have a closer fit or lower clearance whereas a longer sealing zone need not have such a close fit and can have a higher clearance.

The guide sheath 400 can also include additional localized sealing points with the catheter extending through its working lumen. In some implementations, the localized sealing can occur a distance away from the distal end 406 of the sheath 400. In some implementations, a localized sealing can occur at the distal end 406 of the sheath 400. For example, the guide sheath 400 may include a distal tip 406 that is designed to seal well with an outer diameter of a catheter extending through its working lumen. The distal tip 406 can be formed of soft material that is devoid of both liner and reinforcement layers. The lubricious liner layer and also the reinforcement layer can extend through a majority of the body 402 except for a length of the distal tip 406 (see FIG. 2C). The length of this unlined, unreinforced portion of the distal tip 406 of the sheath 400 can vary. In some implementations, the length is between about 3 mm to about 6 mm of the distal end region of the sheath 400. Thus, the liner 409 of the sheath 400 can terminate at least about 3 mm away from the distal-most terminus of the sheath 400 leaving the last 3 mm unlined soft material forming the distal tip 406. In some implementations, the coil and braid of the reinforcement layer can have their ends held in place by a radiopaque markers 411, such as a marker band positioned near a distal-most terminus of the sheath 400. The liner layer 409 can extend at least a length distal to the marker band 411 before terminating, for example, a length of about 1 mm. The staggered termination of the wall layers can aid in the transition from the marker band 411 to the soft polymer material 407 of the distal tip 406. The soft polymer material 407 can extend a length beyond the liner layer 409. The unlined, soft material 407 forming the distal tip 406 can be a PEBAX material having a durometer of no more than about 40 D, no more than about 35 D, no more than about 62 A, or no more than about 25 D. The softness of the material and the length of this unlined distal tip 406 of the sheath 400 can vary. Generally, the material is soft enough to be compressed down onto the outer diameter of the catheter 200 extending through the lumen of the sheath 400, such as upon application of a negative pressure through the lumen. The length of this unlined, unreinforced region 407 of the distal tip 406 is long enough to provide a good seal, but not so long as to cause problems with accordioning or folding over during relative sliding between the sheath 400 and the catheter 200 that might blocking the sheath lumen or negatively impacting slidability of the catheter 200 within the sheath lumen.

The distal tip 406 can have an inner diameter that approaches the outer diameter of the catheter 200 that extends through the sheath 400. In some implementations, the inner diameter of the distal tip 406 can vary depending on what size catheter is to be used. For example, the inner diameter of the sheath at the distal tip 406 can be about 0.106" when the outer diameter of the catheter near the proximal end is about 0.101" such that the difference in diameters is about 0.005". Upon application of a vacuum, the soft unlined and unreinforced distal tip 406 can move to eliminate this 0.005" gap and compress down onto the outer diameter of the catheter 200 near its proximal end region upon extension of the catheter 200 out its distal opening 408. The difference between the inner diameter of the distal tip 406 and the outer diameter of the catheter can be between about 0.002"-0.006". The inner diameter of the distal tip 406 can also be tapered such the inner diameter at the distal-most terminus of the opening 408 is only 0.001" to 0.002" larger than the outer diameter of the proximal end of the catheter 200 extending through the working lumen. In some implementations, the distal tip 406 is shaped such that the walls are beveled at an angle relative to a central axis of the sheath 400, such as about 60 degrees.

In some instances it is desirable for the sheath body 402 to also be able to occlude the artery in which it is positioned, for example, during procedures that may create distal emboli. Occluding the artery stops antegrade blood flow and thereby reduces the risk of distal emboli that may lead to neurologic symptoms such as TIA or stroke. FIG. 2D shows an arterial access device or sheath 400 that has a distal occlusion balloon 440 that upon inflation occludes the artery at the position of the sheath distal tip 406. At any point in a procedure, for example, during removal of an occlusion by aspiration and/or delivery of a stent retriever or other interventional device, the occlusion balloon 440 can be inflated to occlude the vessel to reduce the risk of distal emboli to cerebral vessels. The sheath 400 can include an inflation lumen configured to deliver a fluid for inflation of the occlusion balloon 440 in addition to the working lumen of the sheath 400. The inflation lumen can fluidly connect the balloon 440, for example, to arm 412 on the proximal adaptor. This arm 412 can be attached to an inflation device such as a syringe to inflate the balloon 440 with a fluid when vascular occlusion is desired. The arm 412 may be connected to a passive or active aspiration source to further reduce the risk of distal emboli.

According to some implementations, the length of the guide sheath 400 is long enough to access the target anatomy and exit the arterial access site with extra length outside of a patient's body for adjustments. For example, the guide sheath 400 (whether having a distal occlusion balloon 440 or not) can be long enough to access the petrous ICA from the femoral artery such that an extra length is still available for adjustment.

The sealing clearance between the guide sheath 400 and the catheter 200 can be a function of localized low clearance regions in ID/OD. The size of the clearance can change depending on whether aspiration pressure is applied through the system. For example, the catheter 200 can also include a slit 236 in the luminal portion 222 (shown in FIG. 5B) configured to widen slightly upon application of suction from an aspiration source and improve sealing between the catheter 200 and the guide sheath 400. Additionally or alternatively, the distal tip 406 of the sheath 400 can be designed to move downward onto the outer diameter of the catheter 200 to improve sealing. The strength of the localized seal(s) achieved allows for a continuous aspiration lumen from the distal tip of the catheter 200 to a proximal end 403 of the guide sheath 400 where it is connected to the aspiration source, even in the presence of lower suction forces, with minimal to no leakage. Generally, when there is enough overlap between the catheter 200 and the guide sheath 400 there is no substantial leakage. However, when trying to reach distal anatomy, the catheter 200 may be advanced to its limit and the overlap between the catheter 200 and the guide sheath 400 is minimal. Thus, additional sealing can be desirable to prevent leakage around the catheter 200 into the sheath 400. The sealing between the catheter 200 and the guide sheath 400 can prevent this leakage upon maximal extension of catheter 200 relative to sheath 400.

Distal Access Catheters

Again with respect to FIGS. 2A-2B, the distal access system 100 can include one or more catheters 200 configured to extend through and out the distal end of the guide sheath 400. The catheter 200 can be a distal access, support, or aspiration catheter depending on the method being performed. FIG. 3 illustrates a side elevational view of an implementation of the catheter 200. The catheter 200 can include a relatively flexible, distal luminal portion 222 coupled to a stiffer, kink-resistant proximal extension or proximal control element 230. The term "control element" as used herein can refer to a proximal region configured for a user to cause pushing movement in a distal direction as well as pulling movement in a proximal direction. The control elements described herein may also be referred to as spines, tethers, push wires, push tubes, or other elements having any of a variety of configurations. The proximal control element can be a hollow or tubular element. The proximal control element can also be solid and have no inner lumen, such as a solid rod, ribbon or other solid wire type element. Generally, the proximal control elements described herein are configured to move its respective component (to which it may be attached or integral) in a bidirectional manner through a lumen.

Figure 1B:
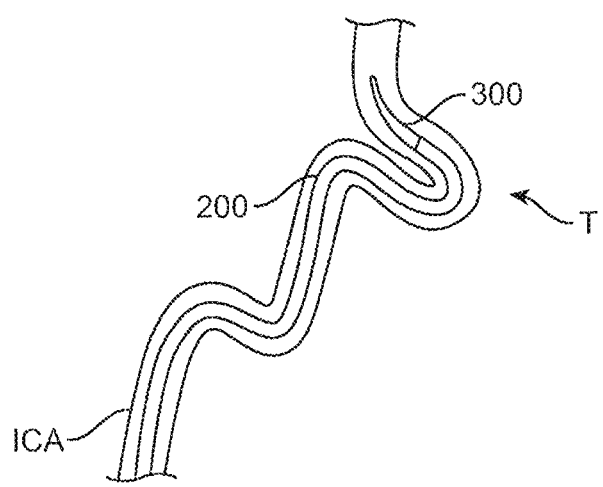

The catheter 200 provides a quick way to access stroke locations with simplicity even through the extreme tortuosity of the cerebral vasculature. The catheters described herein have a degree of flexibility and deliverability that makes them optimally suitable to be advanced through the cerebral vascular anatomy without kinking or ovalizing even when navigating hairpin turns. For example, the distal luminal portion 222 can perform a 180 degree turn (see turn T shown in FIG. 1B near the carotid siphon) and maintain a folded width across of 4.0 mm without kinking or ovalizing. Further, the distal luminal portion 222 has a degree of flexibility that maintains the natural tortuosity of the vessels through which it is advanced without applying straightening forces such that the natural shape and curvature of the anatomy is maintained during use. The catheter 200, particularly in combination with a catheter advancement element 300, which will be described in more detail below, provides an extended conduit beyond the guide sheath 400 having exceptional deliverability through convoluted anatomy that allows for delivering aspirational forces to a target stroke site as well as for the delivery of stroke interventional devices such as another aspiration catheter, or a device such as a stent retriever, stent, flow diverter or other working devices.

A single, inner lumen 223 extends through the luminal portion 222 between a proximal end and a distal end of the luminal portion 222. The inner lumen 223 of the catheter 200 can have a first inner diameter and the working lumen of the guide sheath 400 can have a second, larger inner diameter. Upon insertion of the catheter 200 through the working lumen of the sheath 400, the lumen 223 of the catheter 200 can be configured to be fluidly connected and contiguous with the working lumen of the sheath 400 such that fluid flow into and/or out of the system 100 is possible, such as by applying suction from an aspiration source coupled to the system 100 at a proximal end. The combination of sheath 400 and catheter 200 can be continuously in communication with the bloodstream during aspiration at the proximal end with advancement and withdrawal of catheter 200.

The spined catheter system can create advantages for distal access over conventional, full-length catheters particularly in terms of aspiration. The step change in the internal diameter of the catheter (i.e. from the inner lumen 223 of the catheter to the working lumen of the sheath 400) creates a great advantage in aspiration flow and force that can be generated by the spined catheter 200 in combination with the conventional guide catheter. For example, where a spined catheter 200 with a 0.070" internal diameter is paired with a standard 6 F outer diameter/0.088" internal diameter guide catheter (e.g. Penumbra Neuron MAX 088) can create aspiration physics where the 0.088" catheter diameter will predominate and create a 0.080 equivalent flow in the entire system.

In addition to aspiration procedures, the catheter 200 and distal access system 100 can be used for delivery of tools and interventional working devices. For example, a typical stent retriever to be delivered through the catheter 200 can have a long push wire control element (e.g. 180 cm long). The distal access system 100 having a spined support catheter 200 allows for reaching distal stroke sites using much shorter lengths (e.g. 120 cm-150 cm). The overall length can be as important as diameter and radius on aspiration through the catheter. The shorter lengths in combination with the elimination of the multiple RHVs typical in tri-axial systems allows for a single-operator use.

Where the catheter is described herein as an aspiration catheter it should not be limited to only aspiration. Similarly, where the catheter is described herein as a way to deliver a stent retriever or other working device it should not be limited as such. The systems described herein can be used to perform procedures that incorporate a combination of treatments. For example, the catheter 200 can be used for the delivery of a stent retriever delivery system, optionally in the presence of aspiration through the catheter 200. As another example, a user may start out performing a first interventional procedure using the systems described herein, such as aspiration embolectomy (sometimes referred to as "thrombectomy"), and switch to another interventional procedure, such as delivery of a stent retriever or implant.

The terms "support catheter," "spined catheter," "tethered catheter," "distal access catheter," "aspiration catheter," and "intermediate catheter" may be used interchangeably herein.

It is desirable to have a catheter 200 having an inner diameter that is as large as possible that can be navigated safely to the site of the occlusion, in order to optimize the aspiration force in the case of aspiration and/or provide ample clearance for delivery of a working device. A suitable size for the inner diameter of the distal luminal portion 222 may range between 0.040" and 0.100", or more preferably between 0.054" and 0.088", depending on the patient anatomy and the clot size and composition. The outer diameter of the distal luminal portion 222 can be sized for navigation into cerebral arteries, for example, at the level of the M1 segment or M2 segment of the cerebral vessels. The outer diameter (OD) should be as small as possible while still maintaining the mechanical integrity of the catheter 200. In an implementation, the difference between the OD of distal luminal portion 222 of the catheter 200 and the inner diameter of the working lumen of the guide sheath 400 is between 0.001" and 0.002". In another implementation, the difference is between 0.001" and 0.004". The clearance between inner diameter of the guide sheath 400 and the outer diameter of the catheter 200 can vary throughout the length of the catheter 200. For example, the distal luminal portion 222 of the catheter 200 can have localized regions of enlarged outer diameter creating localized low clearance regions (e.g. about 0.001" difference) configured for localized sealing upon application of aspiration pressure through the system.

In some implementations, the distal luminal portion 222 of the catheter 200 has a maximum outer diameter (OD) configured to fit through a 6 F introducer sheath (0.070"-0.071") and the lumen 223 has an inner diameter (ID) that is sized to receive a 0.054" catheter. In some implementations, the distal luminal portion 222 has a lumen and a distal end having an opening from the lumen, the lumen can have an inner diameter (ID) at the distal end that is at least about 0.052". In some implementations, the distal luminal portion 222 of the catheter 200 has a maximum OD configured to fit through an 8 F introducer sheath (0.088") and the lumen 223 has an ID that is sized to receive a 0.070" or 0.071" catheter. In some implementations, the maximum OD of the distal luminal portion 222 is 2.1 mm and the lumen 223 has an ID that is 0.071". In some implementations, the lumen 223 has an ID that is 0.070" to 0.073". The outer diameter of the guide sheath 400 can be suitable for insertion into at least the carotid artery, with a working lumen suitably sized for providing a passageway for the catheter 200 to treat an occlusion distal to the carotid artery towards the brain. In some implementations, the ID of the working lumen can be about 0.074" and the OD of the body of the guide sheath 400 can be about 0.090", corresponding to a 5 French sheath size. In some implementations, the ID of the working lumen can be about 0.087" and the OD of the body of the guide sheath 400 can be about 0.104", corresponding to a 6 French sheath size. In some implementations, the ID of the working lumen can be about 0.100" and the OD of the body of the guide sheath 400 can be about 0.117", corresponding to a 7 French sheath size. In some implementations, the guide sheath 400 ID is between 0.087" and 0.088" and the OD of the distal luminal portion 222 of the catheter 200 is approximately 0.082" and 0.086" such that the difference in diameters is between 0.001" and 0.005". Smaller or larger sheath sizes are considered. For example, in some implementations the ID of the lumen 223 is about 0.088" and the OD of the distal luminal portion is between 0.101"-0.102". However, a conventional 7 French sheath has an ID that is only about 0.100" and a conventional 8 French sheath has an ID that is about 0.113" such that it would not provide a suitable sealing fit with the OD of the distal luminal portion of the catheter for aspiration embolectomy (i.e. 0.011" clearance). Thus, the guide sheath 400 can be designed to have an inner diameter that is better suited for the 0.088" catheter, namely between 0.106"-0.107". Additionally, the 0.088" catheter can have a step-up in OD from 0.101"-0.102" to about 0.105"-0.107" OD near a proximal end region to provide a localized area optimized for sealing with the guide sheath during application of high pressure.

In an implementation, the luminal portion 222 of the catheter 200 has a uniform diameter from a proximal end to a distal end. In other implementations, the luminal portion 222 of the catheter 200 is tapered and/or has a step-down towards the distal end of the distal luminal portion 222 such that the distal-most end of the catheter 200 has a smaller outer diameter compared to a more proximal region of the catheter 200, for example, near where the distal luminal portion 222 seals with the guide sheath 400. In another implementation, the luminal portion 222 of the catheter OD steps up at or near an overlap portion to more closely match the sheath inner diameter as will be described in more detail below. This step-up in outer diameter can be due to varying the wall thickness of the catheter 200. For example, the catheter 200 can have a wall thickness that is slightly thicker near the proximal end to provide better sealing with the sheath compared to a wall thickness of the catheter 200 near the distal end. The catheter 200 can have a thicker wall at this location while maintaining a uniform inner diameter. This implementation is especially useful in a system with more than one catheter suitable for use with a single access sheath size. In some implementations, a thicker wall can be created by embedding a radiopaque material (e.g. tungsten) such that the localized step-up in OD can be visualized during a procedure. The catheter 200 may have a step-up in outer diameter near the proximal end region that does not result from a thicker wall. For example, the inner diameter of the lumen may also step-up such that the wall thickness remains uniform, but the lumen size increases thereby increasing the overall OD at this location.

The length of the luminal portion 222 can be shorter than a length of the working lumen of the guide sheath 400 such that upon advancement of the luminal portion 222 towards the target location results in an overlap region 348 between the luminal portion 222 and the working lumen (see FIG. 2B). The length of the overlap region 348 can vary depending on the length of the distal luminal portion 222 and the distance to the target location relative to the distal end of the guide sheath 400. Taking into account the variation in occlusion sites and sites where the guide sheath 400 distal tip 406 may be positioned, the length of the luminal portion 222 may range from about 10 cm to about 80 cm, or between 35 cm to about 75 cm, or between about 45 cm to about 60 cm. In some implementations, the distal luminal portion 222 of the catheter 200 can be between 45 cm-70 cm and the control element 230 of the catheter 200 can be between about 90 cm to about 100 cm. In some implementations, the catheter 200 can have a total working length that is approximately 115 cm. In other implementations, the working length of the catheter 200 between a proximal end of the catheter to a distal end of the catheter can be greater than 115 cm up to about 130 cm. In some implementations, the catheter 200 can have a working length greater than 130 cm between a proximal tab 234 (or proximal hub) and the distal tip, for example, 133 cm. The distal luminal portion 222 can have a shaft length of about 40 cm±3 cm. The distal luminal portion 222 can have a shaft length that is at least about 45 cm up to a length that is shorter than the working length of the sheath 400. The body 402 of the guide sheath 400 can be between about 80 cm to about 90 cm.

The length of the luminal portion 222 can be less than the length of the body 402 of the guide sheath 400 such that as the catheter 200 is extended from the working lumen there remains an overlap region 348 of the catheter 200 and the inner diameter of the working lumen. A seal can be formed within a region of the overlap region 348. In some implementations, the length of the luminal portion 222 is sufficient to reach a region of the M1 segment of the middle cerebral artery (MCA) and other major vessels from a region of the internal carotid artery while the proximal end region of the luminal portion 222 of the catheter 200 is still maintained proximal to certain tortuous anatomies (e.g. brachiocephalic take-off BT, the aortic arch AA, or within the descending aorta DA). In an implementation, the luminal portion 222 of the catheter has a length sufficient to position its distal end within the M1 segment of the MCA and a proximal end within the aortic arch proximal to take-offs from the arch. In an implementation, the luminal portion 222 of the catheter has a length sufficient to position its distal end within the M1 segment of the MCA and a proximal end within the descending aorta DA proximal to the aortic arch AA. Used in conjunction with a guide sheath 400 having a sheath body 402 and a working lumen, in an implementation where the catheter 200 reaches the ICA and the distance to embolus can be less than 20 cm.

The distal luminal portion 222 having a length that is less than 80 cm, for example approximately 45 cm up to about 70 cm, The distal luminal portion 222, can allow for an overlap region 348 with the body 402 within which a seal forms with the sheath while still providing sufficient reach to intracranial vessels. The carotid siphon CS is an S-shaped part of the terminal ICA beginning at the posterior bend of the cavernous ICA and ending at the ICA bifurcation into the anterior cerebral artery ACA and middle cerebral artery MCA. In some implementations, the distal luminal portion 222 can be between about 35 cm-80 cm, or between 40 cm-75 cm, or between 45 cm-60 cm long to allow for the distal end of the catheter 200 to extend into at least the middle cerebral arteries while the proximal control element 230 and/or the sealing element on the proximal end region of the distal luminal portion 222 remains proximal to the carotid siphon, and preferably within the aorta as will be described in more detail below.

The distal luminal portion 222 can have a length measured from its point of attachment to the proximal control element 230 to its distal end that is long enough to extend from a region of the internal carotid artery (ICA) that is proximal to the carotid siphon to a region of the ICA that is distal to the carotid siphon, including at least the M1 region of the brain. There exists an overlap region 348 between the luminal portion 222 of the catheter 200 and the working lumen of the guide sheath 400 upon extension of the luminal portion 222 into the target anatomy. A seal to fluid being injected or aspirated can be achieved within the overlap region 348 where the OD of the catheter 200 along at least a portion of the distal luminal portion 222 substantially matches the inner diameter of the guide sheath 400 or the difference can be between 0.001"-0.002". The difference between the catheter OD and the inner diameter of the guide sheath 400 can vary, for example, between 1-2 thousandths of an inch, or between 1-4 thousandths of an inch, or between 1-12 thousandths of an inch. This difference in OD/ID between the sheath and the catheter can be along the entire length of the distal luminal portion 222 or can be a difference in a discrete region of the distal luminal portion 222, for example, a cylindrical, proximal end region of the distal luminal portion 222. In some implementations, a seal to fluid being injected or aspirated between the catheter and the sheath can be achieved within the overlap 348 between their substantially similar dimensions without incorporating any separate sealing structure or seal feature. In some implementations, an additional sealing structure located near the proximal end region of the distal luminal portion 222 provides sealing between the inner diameter of the sheath and the outer diameter of the catheter.

The length of the overlap region 348 between the sheath and the distal luminal portion varies depending on the distance between the distal end of the sheath and the embolus as well as the length of the luminal portion 222 between its proximal and distal ends. The overlap region 348 can be sized and configured to create a seal that allows for a continuous aspiration lumen from the distal tip region of the catheter 200 to a proximal end region 403 of the guide sheath 400 where it can be connected to an aspiration source. In some implementations, the strength of the seal achieved can be a function of the difference between the outer diameter of the catheter 200 and the inner diameter of the working lumen as well as the length of the overlap region 348, the force of the suction applied, and the materials of the components. For example, the sealing can be improved by increasing the length of the overlap region 348. However, increasing the length of the overlap region 348 can result in a greater length through which aspiration is pulled through the smaller diameter of the luminal portion 222 rather than the larger diameter of the working lumen. As another example, higher suction forces applied by the aspiration source can create a stronger seal between the luminal portion 222 and the working lumen even in the presence of a shorter overlap region 348. Further, a relatively softer material forming the luminal portion and/or the body 402 can still provide a sufficient seal even if the suction forces are less and the overlap region 348 is shorter. In an implementation, the clearance of the overlap region 348 can enable sealing against a vacuum of up to approximately 28 inHg with minimal to no leakage. The clearance of the overlap region can enable sealing against a vacuum of up to about 730 mmHg with minimal to no leakage.

In other implementations, the overlap region 348 itself does not provide the sealing between the body 402 and the luminal portion 222. Rather, an additional sealing element positioned within the overlap region 348, for example, a discreet location along a region of the luminal portion 222 narrows the gap between their respective ID and ODs such that sealing is provided by the sealing element within the overlap region 348. In this implementation, the location of the seal between the luminal portion 222 and the body 402 can be positioned more proximally relative to certain tortuous regions of the anatomy. For example, the proximal end region of the luminal portion 222 can have a discreet step-up in outer diameter that narrows the gap between the OD of the luminal portion 222 and the ID of the body 402. This step-up in outer diameter of the luminal portion 222 can be positioned relative to the overall length of the luminal portion 222 such that the sealing region between the two components avoids making sharp turns. For example, the sealing region can include the proximal end region of the luminal portion 222 a certain distance away from the distal tip of the catheter and this sealing region can be designed to remain within the descending aorta DA when the distal end region of the luminal portion 222 is advanced through the aortic arch, into the brachiocephalic trunk BT, the right common carotid RCC, up to the level of the petrous portion of the internal carotid artery and beyond. Maintaining the sealing region below the level of the aortic arch while the distal end of the catheter is positioned within, for example, the M1 region of the MCA is a function of the length of the luminal portion 222 as well as the length and position of the sealing portion on the catheter. The sealing region on the luminal portion 222 can be located a distance from the distal tip of the catheter that is at least about 40 cm, 45 cm, 50 cm, 55 cm, 60 cm, 65 cm, 70 cm, up to about 75 cm from the distal tip of the catheter.

Use of the term "seal" in the context of the catheter and the guide sheath refers to a condition where upon application of an aspiration force fluid is prevented from substantially passing from one side of the seal to the other. For example, the low clearance between the OD of the catheter and the ID of the sheath at the seal can prevent, upon application of aspiration pressure through the system, substantial passage of blood between outer surface of the catheter and the inner surface of the sheath and thereby create a seal. The seal does not necessarily mean the entire catheter system is sealed. For example, even when the catheter is "sealed" with the sheath, blood can still be aspirated into the lumen of the catheter and through the guide sheath (at least until "corking" of the distal end of the catheter 200 where a full seal of the entire system may occur).

The catheter 200 can telescope relative to the sheath (and/or relative to another catheter 200) such that the distal end of the distal luminal portion 222 can reach cerebrovascular targets within, for example, the M 1, M2 regions while the proximal end of the distal luminal portion 222 remains proximal to or below the level of severe turns along the path of insertion. For example, the entry location of the catheter system can be in the femoral artery and the target embolus can be distal to the right common carotid artery (RCC), such as within the M1 segment of the middle cerebral artery on the right side. The proximal end region of the distal luminal portion 222 (e.g. where the sealing element is located and/or where the material transition to the proximal control element 230 occurs) can remain within a vessel that is proximal to severely tortuous anatomy: the carotid siphon, the right common carotid RCC, the brachiocephalic trunk BT, the take-off of the brachiocephalic artery from the aortic arch, the aortic arch AA as it transitions from the descending aorta DA. The descending aorta DA is a consistently straight segment in most anatomies. FIG. 1C illustrates the aortic arch AA, which separates the ascending aorta AscA and descending aorta DA. The distal-most carotid from a femoral access point is the right common carotid RCC artery, which takes off from the brachiocephalic trunk BT (or the left common carotid LCC, which takes off from the same brachiocephalic trunk BT in some patients—the so-called "bovine anatomy"). The distal luminal portion 222 may have a length that, when inserted into the RCC, is configured to extend from a target location in the M1 or M2 regions down to the brachiocephalic trunk BT, or down to the level of the aortic arch AA, or down to the descending aorta DA, which is sometimes referred to herein as being "below the takeoff" of the brachiocephalic trunk BT. This avoids inserting the stiffer proximal control element 230, or the material transition between the stiffer proximal control element 230 and the distal luminal portion 222, from taking the turn of the aortic arch or the turn of the brachiocephalic take-off, which can often be very severe. The turn of the aortic arch and the takeoff of the brachiocephalic are often the first severe turns catheters are likely to traverse as they ascend to the brain via the RCC artery. The less flexible portions of the catheter segment are able to avoid the regions of increased tortuosity near the level of the internal carotid artery. The distal luminal portion 222 can transition in flexibility towards the proximal region to approach the flexibility of the stiffer proximal control element 230. The distal end of the catheter can be used to target the left cerebral circulation while the proximal control element 230 of the catheter 200 as well as the material transitions of the distal luminal portion 222 near the proximal control element 230 remain below the level of tortuosity of the brachiocephalic turn (e.g., within the aorta, proximal to the take-off of the left common carotid (LCC) artery, and preferably within the descending aorta DA). Similarly, the sealing region or a majority of the sealing region between the distal luminal portion 222 and the sheath preferably remains proximal to these severe turns.

In some implementations, the distal luminal portion 222 can have a length that allows the distal end of the distal luminal portion 222 to reach distal to the carotid siphon into the cerebral portion of the internal carotid artery while at the same time the proximal end of the distal luminal portion 222 (e.g. where it transitions to the proximal control element 230 as will be described in more detail below) remains within the aorta proximal to the take-off of the brachiocephalic trunk BT, for example within the descending aorta DA (see FIG. 2C). In this implementation, the distal luminal portion can be between about 35 cm and 75 cm in length, for example, between 45 cm-70 cm, or 65 cm long.

The attachment region between the more rigid, proximal control element 230 and the more flexible, distal luminal portion 222 creates a transition in material and flexibility that can be prone to kinking. Thus, it is preferable to avoid advancing the attachment region into extreme curvatures. For example, the distal luminal portion 222 can have a length that allows the point of attachment to be advanced no further than the first turn of the carotid siphon, or no further than the brachiocephalic artery take-off 610, or nor further than the aortic arch AA, or no further than the descending aorta DA when the catheter is advanced from a femoral access site. In some implementations, the distal luminal portion 222 has a length sufficient to allow the point of attachment to remain within the descending aorta DA while still accessing M1 or M2 regions of the neurovasculature. Locating the material transition within the extreme turn of the brachiocephalic take-off BT from the aortic arch AA is generally avoided when the distal luminal portion 222 has a length that is between about 35 cm to about 75 cm, or 45 cm-70 cm, or 65 cm.

A seal can be created at and/or within the overlap region 348 between the distal luminal portion 222 and the sheath body 402. It can be generally desirable to position the sealing between the distal luminal portion 222 and the sheath body 402 outside of extreme curvatures of the neurovasculature. In some implementations, the distal luminal portion 222 can have a length that allows for the distal end of the distal luminal portion 222 to extend distal to the carotid siphon into the cerebral portion of the internal carotid artery while at the same time the sealing region with the sheath body 402 remains proximal to the brachiocephalic takeoff BT, the aortic arch AA, or within the descending aorta DA. In this implementation, the length can be between about 35 cm to about 75 cm, about 40 cm to about 65 cm, or greater than 40 cm up to a length that is less than the working length of the sheath body 402.

Figure 2C:
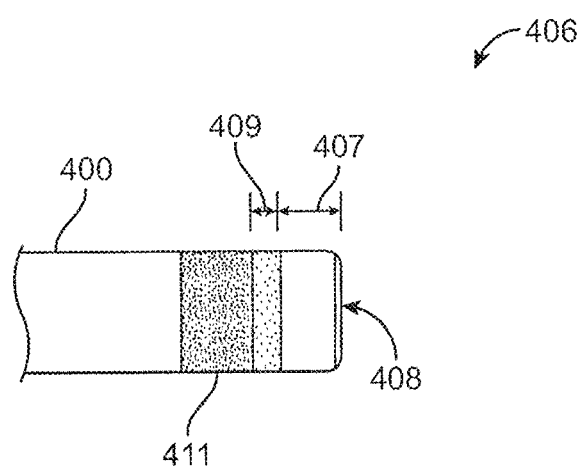
FIG. 2C is a detail view of FIG. 2A taken at circle C-C.
Figure 2D:
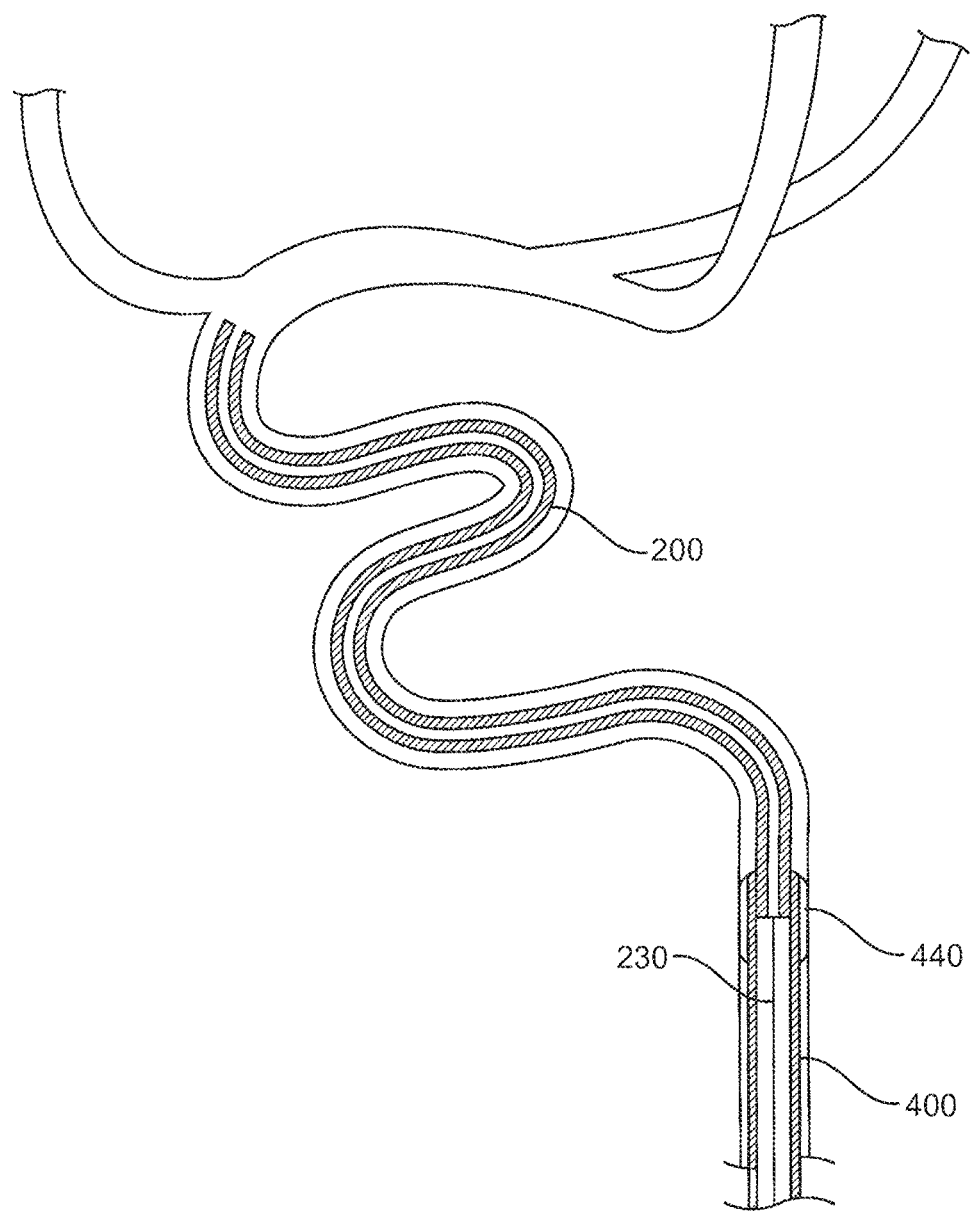
FIG. 2D illustrates an implementation of an arterial access device having a distal occlusion balloon.

With respect to FIG. 2C, the unreinforced region 407 of the distal tip 406 of the sheath 400 can have a length that allows it to provide sufficient sealing force onto the outer surface of the catheter 200 upon application of a negative pressure. The distal luminal portion 222 of the catheter 200 used with this implementation of sheath 400 can have a length that is shorter than 60 cm, shorter than 50 cm, shorter than 40 cm, shorter than 35 cm, shorter than 30 cm to about 10 cm. For example, the distal luminal portion 222 of the catheter 200 when used with a sheath 400 having an unreinforced region 407 configured for sealing against the outer diameter of the catheter 200 can be less than about 30 cm, for example, between about 10 cm and about 30 cm.

Sealing within the overlap region 348 can be due to the small difference in inner and outer diameters. The proximal end region of the distal luminal portion 222 can have a step-up in outer diameter (e.g. increased wall thickness) providing a region of localized sealing with the inner diameter of the guide sheath. Additionally or alternatively, the localized sealing can be due to an additional sealing element positioned on an external surface of the distal luminal portion or an inner surface of the sheath body. A sealing element can include a stepped up diameter or protruding feature in the overlap region. The sealing element can include one or more external ridge features. The one or more ridge features can be compressible when the luminal portion is inserted into the lumen of the sheath body. The ridge geometry can be such that the sealing element behaves as an O-ring, quad ring, or other piston seal design. The sealing element can include one or more inclined surfaces biased against an inner surface of the sheath body lumen. The sealing element can include one or more expandable members actuated to seal. The inflatable or expandable member can be a balloon or covered braid structure that can be inflated or expanded and provide sealing between the two devices at any time, including after the catheter is positioned at the desired site. Thus, no sealing force need be exerted on the catheter during positioning, but rather applied or actuated to seal after the catheter is positioned. The sealing element can be positioned on the external surface of the distal luminal portion, for example, near the proximal end region of the distal luminal portion and may be located within the overlap region. More than a single sealing element can be positioned on a length of the catheter.

The additional sealing element of the distal luminal portion 222 can be a cup seal, a balloon seal, or a disc seal formed of a soft polymer positioned around the exterior of the distal luminal portion near the overlap region to provide additional sealing. The sealing element can be a thin-wall tubing with an outer diameter that substantially matches the inner diameter of the sheath body lumen. The tubing can be sealed on one end to create a cup seal or on both ends to create a disc or balloon seal. The balloon seal can include trapped air that creates a collapsible space. One or more slits can be formed through the wall tubing such that the balloon seal can be collapsible and more easily passed through an RHV. The balloon seal need not include slits for a less collapsible sealing element that maintains the trapped air. The sealing element can be tunable for sheath fit and collapse achieved.

In some implementations, the system can include one or more features that restrict extension of the catheter 200 relative to the sheath 400 to a particular distance such that the overlap region 348 achieved is optimum and/or the catheter 200 is prevented from being over-inserted. For example, a tab can be positioned on a region of the catheter 200 such that upon insertion of the catheter 200 through the sheath 400 a selected distance, the tab has a size configured to abut against the port through which the catheter 200 is inserted to prevent further distal extension of the catheter 200 through the sheath 400. A tab can also be positioned on a region of the catheter advancement element 300 to ensure optimum extension of the catheter advancement element 300 relative to the distal end of the catheter 200 to aid in advancement of the catheter 200 into the intracranial vessels.

Again with respect to FIG. 3, the proximal control element 230 is configured to move the distal luminal portion 222 in a bidirectional manner through the working lumen of the guide sheath 400 such that the distal luminal portion 222 can be advanced out of the guide sheath 400 into a target location for treatment within the target vessel. In some implementations and as shown in FIG. 3, the proximal control element 230 of the catheter 200 can have a smaller outer diameter than the outer diameter of the distal luminal portion 222 forming a proximal spine or tether to the catheter 200. A smaller outer diameter for the proximal control element 230 than the outer diameter of the distal luminal portion 222 allows for the larger diameter working lumen of the sheath 400 to maintain greater aspiration forces than would otherwise be provided by the smaller diameter luminal portion 222 of the catheter 200 or allow for the delivery of working devices through the lumen with less frictional forces. The markedly shorter length of the luminal portion 222 results in a step-up in luminal diameter between the luminal portion 222 contiguous with the working lumen providing a markedly increased radius and luminal area for delivery of a working device and/or aspiration of the clot, particularly in comparison to other systems where the aspiration lumen runs along the entire inner diameter of the aspiration catheter. More particularly, the combined volume of the luminal area of the catheter 200 and the luminal area of the working lumen proximal to the distal luminal portion 222 is greater than the luminal area of the large bore catheter along the entire length of the system. Thus, the likelihood of removing the embolus during a single aspiration attempt may be increased. More particularly, the stepped up luminal diameter along the proximal control element 230 may enable a greater aspiration force to be achieved resulting in improved aspiration of the embolus. Further, this configuration of the catheter 200 and proximal control element 230 greatly speeds up the time required to retract and re-advance the catheter 200 and/or working devices through the working lumen out the distal opening 408. The proximal control element 230 of the catheter 200 has a length and structure that extends through the working lumen of the sheath-guide 400 to a proximal end of the system 100 such that the proximal control element 230 can be used to advance and retract the catheter 200 through the working lumen. The proximal control element 230 of the catheter 200, however, takes up only a fraction of the luminal space of the system 100 resulting in increased luminal area for aspiration and/or delivery of working devices. The stepped up luminal diameter also increases the annular area available for forward flushing of contrast, saline, or other solutions while devices such as microcatheters or other devices may be coaxially positioned in the luminal portion 222 of the catheter 200 and/or the working lumen. This can increase the ease and ability to perform angiograms during device navigation.

In an implementation, the distal luminal portion 222 of the catheter 200 is constructed to be flexible and lubricious, so as to be able to safely navigate to the target location. The distal luminal portion 222 can be kink resistant and collapse resistant when subjected to high aspiration forces so as to be able to effectively aspirate a clot. The luminal portion 222 can have increasing flexibility towards the distal end with smooth material transitions along its length to prevent any kinks, angulations or sharp bends in its structure, for example, during navigation of severe angulations such as those having 90° or greater to 180° turns, for example at the aorto-iliac junction, the left subclavian artery LSA take-off from the aorta AA, the takeoff of the brachiocephalic (innominate) artery BT from the ascending aorta AscA and many other peripheral locations just as in the carotid siphon. The distal luminal portion 222 can transition from being less flexible near its junction with the proximal control element 230 to being more flexible at the distal-most end. For example, a first portion of the distal luminal portion 222 can be formed of a material having a material hardness of 72 D along a first length, a second portion can be formed of a material having a material hardness of 55 D along a second length, a third portion can be formed of a material such as Pebax or MX1205 having a material hardness of 40 D along a third length, a fourth portion can be formed of a material having a material hardness of 35 D along a fourth length, a fifth portion can be formed of a material having a material hardness of 25 D along a fifth length, a sixth portion can be formed of a material such as Tecoflex having a material hardness of 85 A along a sixth length, and a final distal portion of the catheter can be formed of a material such as Tecoflex having a material hardness of 80 A. In some implementations, the final distal portion of the distal luminal portion 222 of the catheter 200 can be formed of a material such as Tecothane having a material hardness of 62 A. Thus, the distal luminal portion 222 transitions from being less flexible near its junction with the proximal control element 230 to being more flexible at the distal-most end where, for example, a distal tip of the catheter advancement element 300 can extend from the distal end of the catheter 200. Other procedural catheters described herein can have a similar construction providing a variable relative stiffness that transitions from the proximal end towards the distal end of the catheter as will be described elsewhere herein. The change in flexibility from proximal to distal end of the distal luminal portion 222 can be achieved by any of a variety of methods.

The distal luminal portion 222 can include two or more layers. In some implementations, the distal luminal portion 222 includes an inner lubricious liner, a reinforcement layer, and an outer jacket layer, each of which will be described in more detail.

The lubricious inner liner can be a PTFE liner, with one or more thicknesses along variable sections of flexibility. The PTFE liner can be a tubular liner formed by dip coating or film-casting a removable mandrel, such as a silver-plated copper wire as is known in the art. Various layers can be applied having different thicknesses. For example, a base layer of etched PTFE can be formed having a thickness of about 0.005". A second, middle layer can be formed over the base layer that is Tecoflex SG-80A having a thickness of about 0.0004". A third, top layer can be formed over the middle layer that is Tecoflex SG-93A having a thickness of about 0.0001" or less. A reinforcement layer and/or reinforcement fiber can be applied to the inner liner, followed by the outer jacket layer and/or additional outer coating prior to removing the mandrel by axial elongation.

The reinforcement layer is a generally tubular structure formed of, for example, a wound ribbon or wire coil or braid. The material for the reinforcement structure may be stainless steel, for example 304 stainless steel, Nitinol, cobalt chromium alloy, or other metal alloy that provides the desired combination of strengths, flexibility, and resistance to crush. In some implementations, the distal luminal portion 222 has a reinforcement structure that is a Nitinol ribbon wrapped into a coil. For example, the coil reinforcement can be a tapered ribbon of Nitinol set to a particular inner diameter (e.g. 0.078" to 0.085" inner diameter) and having a pitch (e.g. between 0.012" and 0.016"). The ribbon can be 304 stainless steel (e.g. about 0.012"×0.020"). The coil can be heat-set prior to transferring the coil onto the catheter. The pitch of the coil can increase from proximal end towards distal end of the distal luminal portion 222. For example, the ribbon coils can have gaps in between them and the size of the gaps can increase moving towards the distal end of the distal luminal portion 222. For example, the size of the gap between the ribbon coils can be approximately 0.016" gap near the proximal end of the distal luminal portion 222 and the size of the gap between the ribbon coils near the distal end can be larger such as 0.036" gap. This change in pitch provides for increasing flexibility near the distal-most end of the distal luminal portion 222. The distal luminal portion 222 can additionally incorporate one or more reinforcement fibers (see FIGS. 8B-8C) configured to prevent elongation of the coils, as will be described in more detail below. The reinforcement structure can include multiple materials and/or designs, again to vary the flexibility along the length of the distal luminal portion 222.

The outer jacket layer may be composed of discreet sections of polymer with different durometers, composition, and/or thickness to vary the flexibility along the length of the distal luminal portion 222.

At least a portion of the outer surface of the catheter 200 can be coated with a lubricious coating such as a hydrophilic coating. In some implementations, the coating may be on an inner surface and/or an outer surface to reduce friction during tracking. The coating may include a variety of materials as is known in the art. The proximal control element 230 may also be coated to improve tracking through the working lumen. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, HYDAK coatings (e.g. B-23K, HydroSleek), and the like, and mixtures and combinations thereof. Hydrophilic polymers may be blended among themselves or with formulated amounts of water insoluble compounds (including some polymers) to yield coatings with suitable lubricity, bonding, and solubility.

In some implementations, the distal luminal portion 222 includes two or more layers. In some implementations, the distal luminal portion 222 includes an inner lubricious liner, a reinforcement layer, and an outer jacket layer. The outer jacket layer may be composed of discreet sections of polymer with different durometers, composition, and/or thickness to vary the flexibility along the length of the distal luminal portion 222. In an implementation, the lubricious inner liner is a PTFE liner, with one or more thicknesses along variable sections of flexibility. In an implementation, the reinforcement layer is a generally tubular structure formed of, for example, a wound ribbon or wire coil or braid. The material for the reinforcement structure may be stainless steel, for example 304 stainless steel, nitinol, cobalt chromium alloy, or other metal alloy that provides the desired combination of strengths, flexibility, and resistance to crush. In an implementation, the reinforcement structure includes multiple materials and/or designs, again to vary the flexibility along the length of the distal luminal portion 222. In an implementation, the outer surface of the catheter 200 is coated with a lubricious coating such as a hydrophilic coating. The proximal control element 230 may also be coated to improve tracking through the working lumen. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof.

Again with respect to FIGS. 2A-2B, the distal luminal portion 222 of the catheter 200 can have a plurality of radiopaque markings. A first radiopaque marker 224a can be located near the distal tip region to aid in navigation and proper positioning of the tip under fluoroscopy. Additionally, a proximal region of the catheter 200 may have one or more proximal radiopaque markers 224b so that the overlap region 348 can be visualized as the relationship between a radiopaque marker 411 on the guide sheath 400 and the radiopaque marker 224b on the catheter 200. The proximal region of the catheter 200 may also have one or more radiopaque markings providing visualization, for example, of the proximal opening into the single lumen of the catheter as will be described in more detail below. In an implementation, the two radiopaque markers (marker 224a at distal tip and a more proximal marker 224b) are distinct so as to minimize confusion of the fluoroscopic image, for example the catheter proximal marker 224b may be a single band and the marker 411 on the guide sheath 400 may be a double band and any markers on a working device delivered through the distal access system can have another type of band or mark. The radiopaque markers 224 of the distal luminal portion 222, particularly those near the distal tip region navigating extremely tortuous anatomy, can be relatively flexible such that they do not affect the overall flexibility of the distal luminal portion 222 near the distal tip region. The radiopaque markers 224 can be tungsten-loaded or platinum-loaded markers that are relatively flexible compared to other types of radiopaque markers used in devices where flexibility is not paramount. In some implementations, the radiopaque marker can be a band of tungsten-loaded PEBAX having a durometer of 35 D.

Figure 8A:
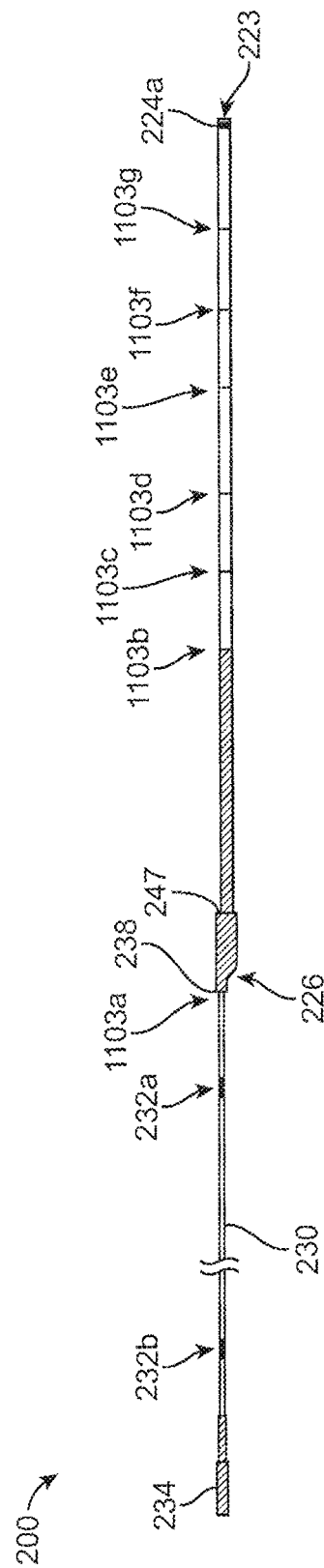
FIG. 8A is a side view of an implementation of a catheter.
Figure 8B:
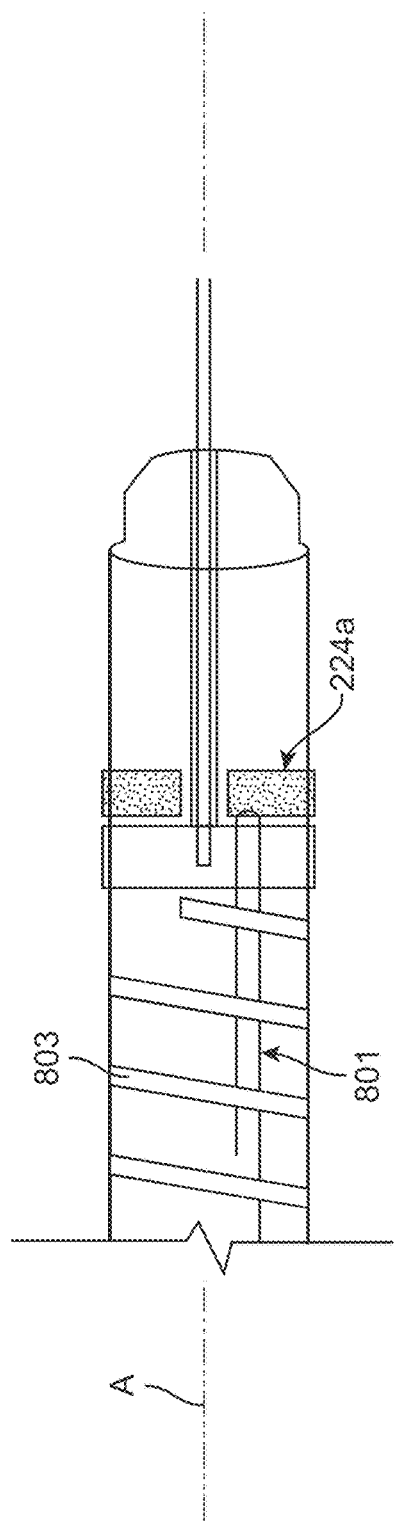
FIG. 8B is a schematic cut-away view of the distal end region of the catheter of FIG. 8A.
Figure 8C:
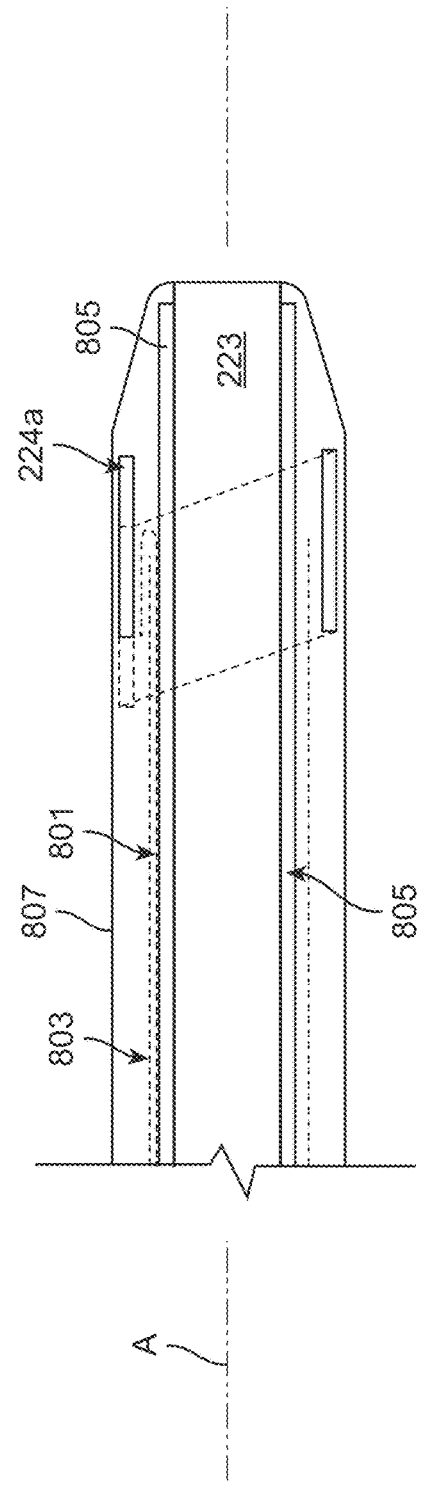
FIG. 8C is a schematic cross-sectional view of the distal end region of the catheter of FIG. 8A.

As best shown in FIGS. 8B-8C, at least one reinforcement fiber 801 can be incorporated within a wall of the distal luminal portion 222 to prevent elongation of a coiled reinforcement layer 803. The fiber 801 can be positioned between the liner layer 805 and the reinforcement layer 803. The fiber 801 can extend along the longitudinal axis A of the catheter 200 from a proximal end region of the distal luminal portion 222 to a distal end region of the portion 222. The proximal end of the fiber 801 can be coupled to a region of the distal luminal portion 222 near where it couples to the proximal control element 230. A distal end of the fiber 801 can terminate near the distal end of the distal luminal portion 222. The distal end of the fiber 801 can be captured between the distal marker band 224a and an end of the reinforcement layer 803. The distal marker band 224a can be fully encapsulated between the inner liner 805 and the outer jacket 807. In some implementations, the distal end of the fiber 801 extends distal to the last coil of the reinforcement layer 803 running under the marker band 224a and then looping around the band 224a back in a proximal direction. The free end of the fiber 801 is thereby captured under the reinforcement layer 803 and the marker band 224a. The reinforcement fiber 801 thus terminates at the location the reinforcement layer 803 terminates thereby leaving a length of between about 10 cm-12 cm of the unreinforced distal-most tip region. The catheter 200 can include a plurality of reinforcement fibers 801 extending longitudinally along the distal luminal portion 222, such as two, three, four, or more fibers 801 distributed around the circumference of the portion 222 and aligned parallel with one another and with the longitudinal axis A of the catheter 200. The reinforcement fiber 801 may also terminate at a more distal location or at a more proximal location than the location of the distal terminal marker 224a. The material of the reinforcement fiber 801 can vary, including but not limited to various high tenacity polymers like polyester, PEEK, and other similar materials.

Figure 9A:
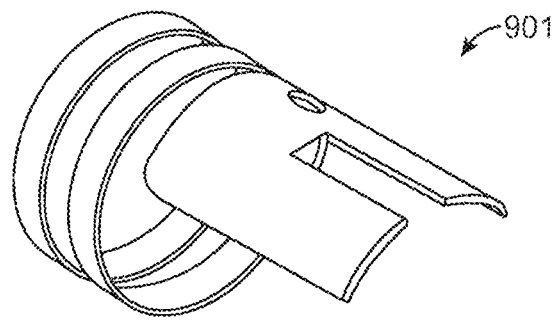
FIGS. 9A-9C are various views of a proximal extension connector.
Figure 9B:
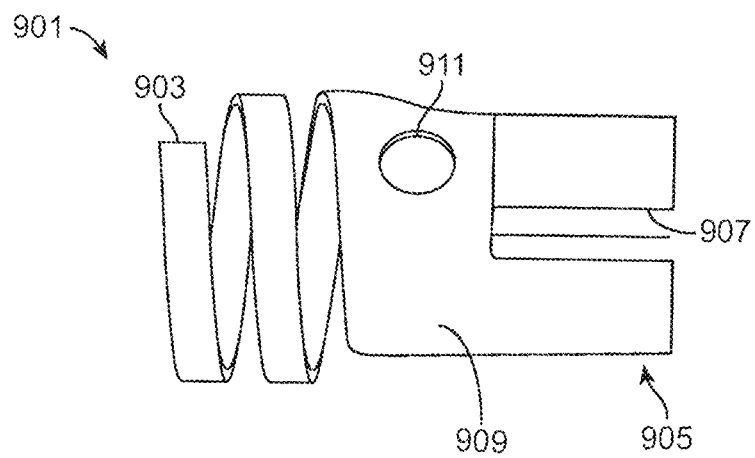
Figure 9C:
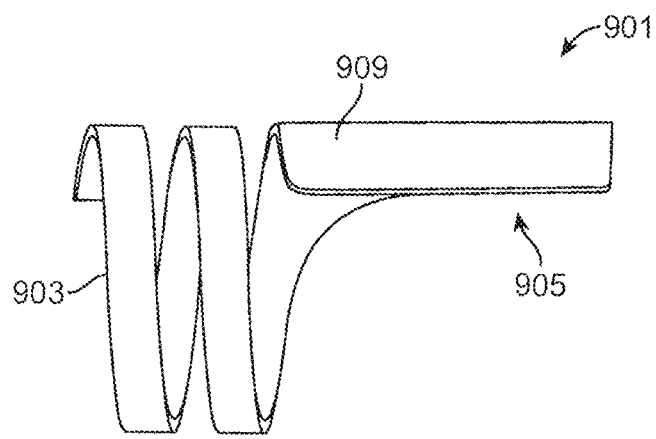

The distal luminal portion 222 of the catheter 200 can have a proximal control element 230 coupled near a proximal opening into the single lumen of the distal luminal portion 222. The distal luminal portion 222 and the proximal control element 230 can be attached to one another by a coupling band 901 (see FIGS. 9A-9C). A proximal end 905 of the coupling band 901 can attach to a distal end of the proximal control element 230 and a distal end of the coupling band 901 can attach to the distal luminal portion 222. The proximal end 905 of the coupling band 901 may include a slot 907 configured to be welded with the proximal control element 230 of the catheter 200. The catheter 200 may include a strain relief along a skive length such as a tungsten loaded PEBAX. The distal end of the coupling band 901 can be cut to form a plurality of spirals 903. These spirals 903 are configured to intersperse with the coils of the reinforcement layer 803 at the proximal end region of the distal luminal portion 222. The size of the gap between the spirals 903 of the coupling band 901 can be substantially similar to the size of the gap between the coils of the reinforcement layer 803 such that they can neatly intersperse with one another without creating any localized areas of increased wall thickness due to overlap. The thickness of the spirals 903 can, but need not, be similar to the thickness of the ribbon forming the reinforcement layer 803. For example, the coiled reinforcement layer 803 can be formed of a Nitinol ribbon having a thickness of about 0.003". The coupling band 901 can have a wall thickness that is about 0.003" such that the spirals 903 and the coils of the reinforcement layer 803 can be similar in material thickness. This similarity in material thickness between the coils and the spirals 903 contribute to a generally uniform outer profile that can be kept to a minimum and avoid creating a substantially increased wall thickness in this coupling region. A low profile proximal end of the distal luminal portion 222 aids in maximizing the inner diameter while keeping the outer diameter as small as possible, for example, such that the inner diameter of the guide sheath to a minimum (e.g. less than about 0.113" or about 0.107"). The coupling band 901 can include an aperture 911 through middle region 909 that is configured to receive a proximal end of the reinforcement fiber 801 extending longitudinally through the distal luminal portion 222. The region of overlap between the distal end of the proximal control element and the distal luminal portion 222 can vary, but can be at least about 5 mm, at least about 7 mm, at least about 10 mm to provide a smooth and even transition. The overlap between the proximal control element and the distal luminal portion 222 may be about 5 mm up to about 15 mm.

As mentioned the distal end of the proximal control element 230 can be welded to the proximal end 905 of the coupling band 901. In some implementations, the distal end region of the proximal control element 230 is skived in places and is flat in other places. The proximal control element 230 can be a stainless steel ribbon (e.g. 0.012"×0.020" or 0.014"×0.020" along a majority of its length). A distal end region of the proximal control element 230 can have a discontinuous taper that allows for the thickness of the ribbon to transition from the thickness of 0.012" or 0.014" down to a thickness that matches or is not significantly different from a thickness of the spirals 903 on the coupling band 901 that is attached to a proximal end region of the distal luminal portion 222. The discontinuous taper can include a flat length bound on proximal and distal ends by a tapered length. The flat length allows for a more uniform, minimum material thickness between the distal luminal portion 222 and the proximal control element 230 that avoids introducing weak points that are more prone to kinking. For example, the distal end region of the proximal control element 230 can have a first tapered length that transitions in thickness from 0.012" to a thickness of 0.008" and a second tapered length that transitions from the flat length thickness down to about 0.003". In other implementations, the distal end region of the proximal control element 230 can have a first tapered length that transitions in thickness from 0.014" to a thickness of 0.010" and a second tapered length that transitions from the flat length thickness down to about 0.003". The spirals 903 of the coupling band 901 can have a thickness matches this terminal thickness of the proximal control element 230. The lengths of the tapered and flat portions can vary. In some implementations, the first tapered length can be approximately 0.12 cm, the flat length can be approximately 0.2 cm, and the second tapered length can be approximately 0.15 cm. The uniform thickness along this flat length provides for a useful target in terms of manufacturing the catheter. The catheter need not incorporate a ribbon proximal control element 230 and can have any of a variety of configuration as described elsewhere herein.

As mentioned previously, the proximal control element 230 is configured to allow distal advancement and proximal retraction of the catheter 200 through the working lumen of the guide sheath 400 including passage out the distal opening 408. In an implementation, the length of the proximal control element 230 is longer than the entire length of the guide sheath 400 (from distal tip to proximal valve), such as by about 5 cm to 15 cm. The length of the body 402 can be in the range of 80 to 90 cm or up to about 100 cm or up to about 105 cm and the length of the proximal control element 230 can be between 90-100 cm.

Again with respect to FIG. 3, the proximal control element 230 can include one or more markers 232 to indicate the overlap between the distal luminal portion 222 of the catheter 200 and the sheath body 402 as well as the overlap between the distal luminal portion 222 of the catheter 200 and other interventional devices that may extend through the distal luminal portion 222. At least a first mark 232*a* can be an RHV proximity marker positioned so that when the mark 232*a* is aligned with the sheath proximal hemostasis valve 434 during insertion of the catheter 200 through the guide sheath 400, the catheter 200 is positioned at the distal-most position with the minimal overlap length needed to create the seal between the catheter 200 and the working lumen. At least a second mark 232*b* can be a Fluoro-saver marker that can be positioned on the control element 230 and located a distance away from the distal tip of the distal luminal portion 222. In some implementations, a mark 232 can be positioned about 100 cm away from the distal tip of the distal luminal portion 222.

The proximal control element 230 can include a gripping feature such as a tab 234 on the proximal end to make the proximal control element 230 easy to grasp and advance or retract. The tab 234 can couple with one or more other components of the system as will be described in more detail below. The proximal tab 234 can be designed to be easily identifiable amongst any other devices that may be inserted in the sheath proximal valve 434, such as guidewires or retrievable stent device wires. A portion of the proximal control element 230 and/or tab 234 can be colored a bright color, or marked with a bright color, to make it easily distinguishable from guidewire, retrievable stent tethers, or the like. Where multiple catheters 200 are used together in a nesting fashion to reach more distal locations within the brain, each proximal control element 230 and/or tab 234 can be color-coded or otherwise labeled to clearly show to an operator which proximal control element 230 of which catheter 200 it is coupled to. The proximal portion 366 of the catheter advancement element 300 can also include a color to distinguish it from the proximal control element 230 of the catheter 200.

The tab 234 can be integrated with or in addition to a proximal hub coupled to a proximal end of the control element 230. For example, as will be described in more detail below, the proximal control element 230 can be a hypotube having a lumen. The lumen of the hypotube can be in fluid communication with the proximal hub at a proximal end of the control element 230 such that aspiration forces and/or fluids can be delivered through the hypotube via the proximal hub. The proximal control element 230 can also be a solid element and need not include a lumen to direct aspiration forces to the distal end of the catheter 200.

The proximal control element 230 can be configured with sufficient stiffness to allow advancement and retraction of the distal luminal portion 222 of the catheter 200, yet also be flexible enough to navigate through the cerebral anatomy as needed without kinking. The configuration of the proximal control element 230 can vary. In some implementations, the proximal control element 230 can be a tubular element having an outer diameter that is substantially identical to the outer diameter of the distal luminal portion 222 similar to a typical catheter device. In other implementations, the outer diameter of the proximal control element 230 is sized to avoid taking up too much luminal area in the lumen of the guide sheath 400 to provide a step-up in inner diameter for aspiration.

Figure 4F:
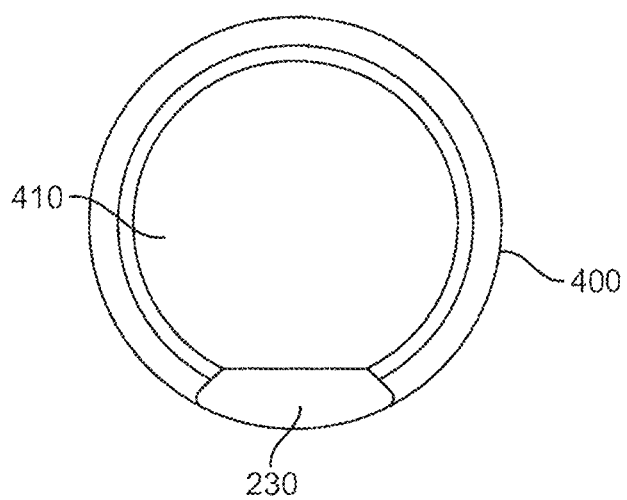
FIGS. 4F-4G are cross-sectional, schematic views comparing trapezoid- and D-shaped proximal extensions, respectively, relative to a working lumen of an access sheath.
Figure 4G:
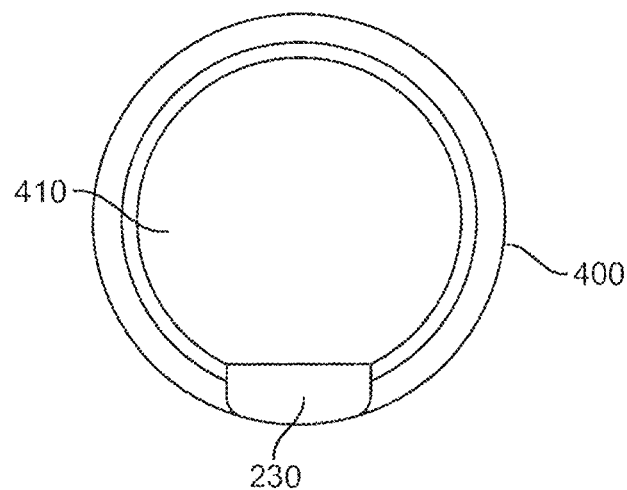

The proximal control element 230 can be a solid metal wire that is round, rectangular, trapezoid, D-shape, or oval cross-sectional shape (see FIGS. 4A-4G). The proximal control element 230 can be a flattened ribbon of wire having a rectangular cross-sectional shape as shown in FIG. 4A. The flattened ribbon of wire can also have square, rectangular, or other cross-sectional shape. The ribbon of wire can be curved into a circular, oval, c-shape, or quarter circle or other cross-sectional area along an arc. As such, an inner-facing surface of the ribbon can be substantially flat and an outer-facing surface of the ribbon (i.e. the surface configured to abut against an inner diameter of the access sheath through which it extends) can be substantially curved (see FIGS. 4F-4G). The curvature of the surface can substantially match the curvature of the inner surface of the access sheath. The resulting cross-sectional shape of such a ribbon can be generally trapezoidal. The overall dimensions of the ribbon can vary depending on its cross-sectional shape and the size of the distal luminal portion. The 0.054" sized catheter 200 can have a proximal control element 230 that is trapezoidal or D-shaped in cross-section. The inner-facing, flat surface can have a width that is approximately 0.020" wide and in the case of the trapezoidal-shaped implementation, the outer-facing, curved surface can extend along an arc that is approximately 0.030" long. The 0.070" sized catheter 200 can have a proximal extension that is trapezoidal or D-shaped in cross-section, and the width of the inner-facing, flat surface is slightly greater, for example, approximately 0.025" and in the case of the trapezoidal-shaped implementation, the outer-facing, curved surface can extend along an arc that is approximately 0.040" long. The 0.088" sized catheter 200 can have a proximal extension that is trapezoidal or D-shaped in cross-section, and the width of the inner-facing, flat surface is approximately 0.035" and the outer-facing, curved surface of the trapezoidal-shaped implementation can extend along an arc that is approximately 0.050" long.

The proximal control element 230 can be a hollow wire having a lumen 235 extending through it, such as a hypotube as shown in FIG. 4B. The hypotube can have an oval or circular shape. In an implementation, the proximal control element 230 is a ribbon of stainless steel having dimensions of about 0.012"×0.020". In an implementation, the proximal control element 230 is a ribbon of stainless steel having dimensions of about 0.014"×0.020". In an implementation, the proximal control element 230 is a round wire, with dimensions from 0.014" to 0.018". In another implementation, the proximal control element 230 is a ribbon with dimensions ranging from 0.010" to 0.015" thick, and 0.015" thick to 0.025" thick. In an implementation, the proximal control element 230 is a hypotube formed from a flattened ribbon of stiff material rolled into a tubular shape to have a lumen 235. In some implementations, the proximal control element 230 can be formed of a flattened ribbon of stainless steel and rolled into a hypotube such that the proximal control element 230 has a wall thickness of about 0.007", an inner diameter of about 0.004" and an outer diameter of about 0.018" before the hypotube is modified into an oval cross-sectional shape. The ovalized hypotube can maintain an inner diameter that is at least 0.001" along at least a first dimension and an outer diameter that is at least 0.015" along at least a first dimension. In an implementation, the proximal control element 230 material is a metal such as a stainless steel or nitinol as well as a plastic such as any of a variety of polymers.

In an implementation, the proximal control element 230 is a stainless steel hypotube having an oval cross-sectional shape (see FIG. 4B). The oval tubular shape can increase the column strength, pushability and kink resistance of the proximal control element 230 for improved advancement through tortuous anatomy. The cross-sectional area of an oval hypotube minimizes the impact of the catheter 200 on movement of other tools through the working lumen 410 of the sheath 400. FIG. 4C illustrates a cross-sectional view of the working lumen 410 of the sheath 400 having a proximal control element 230a extending therethrough. The proximal control element 230a has a rectangular cross-sectional shape. FIG. 4D illustrates a cross-sectional view of the working lumen 410 having an ovalized hypotube proximal control element 230b and a catheter advancement element 300 extending therethrough. FIG. 4E illustrates the comparison of surface area between the rectangular-shaped ribbon 230a and the oval hypotube 230b. The oval hypotube 230b has less surface area compared to the rectangular-shaped ribbon 230b allowing for a greater flow rate through the working lumen 410, for example, during application of aspirating forces. The materials, dimensions, and shape of the proximal control element 230 can be selected based on the materials, dimensions, and shape of the distal luminal portion 222. For example, the proximal control element 230 can be a rectangular ribbon of 340 stainless steel that is 0.012"×0.020" and the distal luminal portion 222 can have an inner diameter of about 0.054" to about 0.072". In a further implementation, the proximal control element 230 can be a rectangular ribbon of 340 stainless steel that is 0.014"×0.020" and the distal luminal portion 222 can have an inner diameter of about 0.088". The additional heft of the stainless steel ribbon 230 can be useful in advancing a larger inner diameter catheter without kinking.

Now with respect to FIGS. 5A-5F, the junction between the distal luminal portion 222 of the catheter 200 and the proximal control element 230 can be configured to allow a smooth transition of flexibility between the two portions so as not to create a kink or weak point. The smooth transition at the joint between the distal luminal portion 222 and the proximal control element 230 also allows for smooth passage of devices through the contiguous inner lumen created by the working lumen of the guide sheath 400 and the lumen 223 of the luminal portion 222 of the catheter 200. In an implementation, the distal luminal portion 222 has a transition section 226 near the proximal opening into the single lumen and where the luminal portion 222 couples to the proximal control element 230 (see FIG. 5A). The transition section 226 can have an angled cut such that there is no abrupt step transition from the working lumen of the guide sheath 400 to the inner lumen 223 of the catheter 200. The angled cut can be generally planer. In an alternate implementation, the angled cut is curved or stepped to provide a more gradual transition zone. The proximal end region of the distal luminal portion 222 can be angled in an oblique manner relative to a longitudinal axis of the catheter 200 such that the proximal end and proximal opening into the lumen are at an angle other than 90° to the longitudinal axis of the catheter 200, for example between approximately 0°, 5°, 10°, 15°, 20°, 25°, 30°, 35°, 40°, or 45° up to less than 90°. The proximal end region of the distal luminal portion 222 can also be aligned substantially perpendicular to the longitudinal axis of the catheter 200 such that the proximal end and proximal opening into the lumen are substantially 90° to the longitudinal axis of the catheter 200. Similarly, the distal end region of the distal luminal portion 222 can be angled in an oblique manner relative to a longitudinal axis of the catheter 200 such that the distal end and distal opening from the lumen 223 are at an angle other than 90° to the longitudinal axis of the catheter 200, for example between approximately 0°, 5°, 10°, 15°, 20°, 25°, 30°, 35°, 40°, or 45° up to less than 90°. The distal end region of the distal luminal portion 222 can also be aligned substantially perpendicular to the longitudinal axis of the catheter 200 such that the distal end and distal opening into the lumen are substantially 90° to the longitudinal axis of the catheter 200.

The proximal control element 230 can be coupled to a proximal end region of the catheter 200 and/or may extend along at least a portion of the distal luminal portion 222 such that the proximal control element 230 couples to the distal luminal portion 222 a distance away from the proximal end defining the proximal opening into the lumen, for example via the coupling band 901. The proximal control element 230 can be coupled to the distal luminal portion 222 by a variety of mechanisms including bonding, welding, gluing, sandwiching, stringing, tethering, or tying one or more components making up the proximal control element 230 and/or portion 222. The distal luminal portion 222 and the proximal control element 230 may be joined by a weld bond, a mechanical bond, an adhesive bond, or some combination thereof. In some implementations, the proximal control element 230 and luminal portion 222 are coupled together by sandwiching the proximal control element 230 between layers of the distal luminal portion 222. For example, the proximal control element 230 can be a hypotube or rod having a distal end that is skived, ground or cut such that the distal end can be laminated or otherwise attached to the layers of the catheter portion 222 near a proximal end region. The skive length of the proximal control element 230 can be about 7 mm and can incorporate a tungsten loaded Pebax strain relief along the length. The region of overlap between the distal end of the proximal control element 230 and the portion 222 can be at least about 1 cm. This type of coupling allows for a smooth and even transition from the proximal control element 230 to the luminal portion 222.

Still with respect to FIGS. 5A-5F, the transition section 226 of the distal luminal portion 222 can open up into a proximal tail 238 extending a length proximal to the transition section 226. In some implementations, the proximal tail 238 has a cross-sectional geometry that is substantially curved. For example, the proximal tail 238 can extend along an arc of the longitudinal axis of the catheter 200 between about 20 to about 90 degrees. In some implementations, the proximal tail 238 is curved to create a funnel-shape and aids in loading and reloading a catheter advancement element 300 into the lumen of the catheter 200. In other implementations, the edges of the proximal tail 238 curve such that the proximal tail 238 is not substantially flat. The curved shape can vary including a tear-drop shape that allows for a smooth transition and better loading/reloading of the catheter advancement element 300 into the lumen and avoids flat edges that can abut and catch the component as it is inserted. In other implementations, the proximal tail 238 is substantially flat. The proximal tail 238 can provide a smooth transition between distal luminal portion 222 and proximal control element 230 when the device is forced to bend. This can reduce the likelihood of kinking and facilitate pushing against resistance.

The dimensions of the proximal tail 238 can vary. The proximal tail 238 shown in FIGS. 5A-5F is relatively wide compared to the width of the proximal control element 230 and, in turn, can have a greater length without negatively impacting the ability of other devices to insert through the proximal opening into the lumen at the transition region 226. In other implementations, the proximal tail 238, defined by a region that is unsupported by the coils of the reinforcement layer 803 and located proximal to the coupling band 901, can have a shorter length. The width of this proximal tail 238 can taper along this shorter length to a width of the proximal control element 230. The tapered shorter proximal tail 238 can mitigate issues with insertion of tools into the proximal opening. Generally speaking, wide proximal tails 238 can be longer than proximal tails 238 that taper down to the width of the proximal control element 230.

A proximal region of the distal luminal portion 222 can incorporate one or more markers to provide visualization under fluoro during loading/reloading of the catheter advancement element 300. For example, the proximal end region can include a region of Pebax (e.g. 35 D) loaded with tungsten (80%) for radiopacity. In some implementations, the proximal tail 228 and/or the transition section 226 defining the proximal opening into the lumen of the luminal portion 222 can be coated or embedded with a radiopaque material such that the opening into the lumen can be fully visualized during use. The radiopaque material embedded in this proximal end region can create a step-up in outer diameter.

The distal end of the proximal control element 230 and/or the distal luminal portion 222 may have features that facilitate a mechanical joint during a weld, such as a textured surface, protruding features, or cut-out features. During a heat weld process, the features would facilitate a mechanical bond between the polymer distal luminal portion 222 and the proximal control element 230. For example, as shown in FIGS. 6A-6F the proximal end of the distal luminal portion 222 can include a short mating sleeve 240 coupled to a proximal edge 221 of the distal luminal portion 222. The sleeve 240 can include an inner lumen extending between a proximal opening 242 and a distal opening 241. The distal end of the proximal control element 230 can insert through the proximal opening 242 and within the inner lumen of the sleeve 240 to couple the proximal control element 230 to the distal luminal portion 222. In some implementations, the proximal control element 230 can couple with the distal luminal portion 222 such that a distal opening 231 of the hypotube forming the proximal control element 230 can communicate with the lumen 223 of the distal luminal portion 222, for example, through the distal opening 241 of the sleeve 240. The sleeve 240 can also provide transition between distal luminal portion 222 and proximal control element 230 similar to the proximal tail 238. The distal luminal portion 222 need not include a mating sleeve 240 to couple with the proximal control element 230. For example, the distal end of the proximal control element 230 can insert through a wall of the proximal tail 238 at the proximal end of the distal luminal portion 222 (see FIG. 5A, 5E-5F). The distal end of the proximal control element 230 can extend along the length of the proximal tail 238 and along at least a length of the wall of the distal luminal portion 222.

Figure 5A:
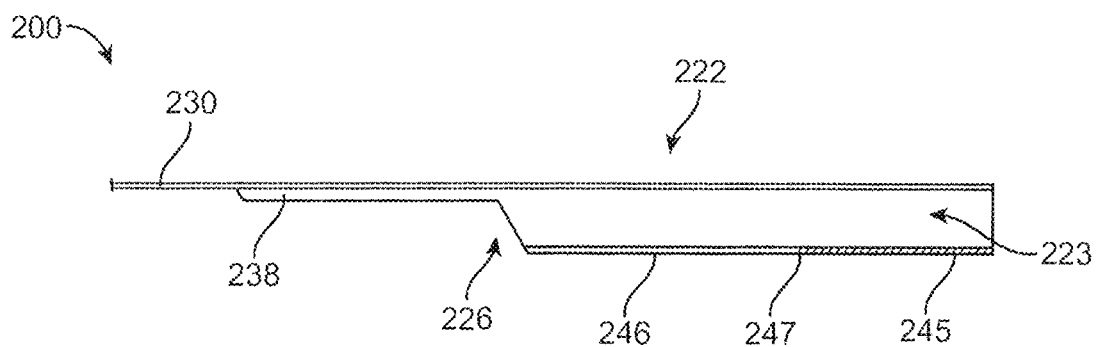
FIG. 5A is a side elevational view of an implementation of a spined distal access catheter.
Figure 5B:
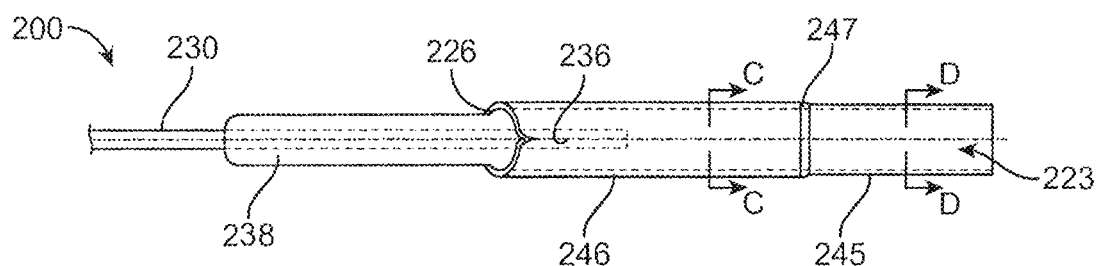
FIG. 5B is a top plan view of the spined distal access catheter of FIG. 5A.
Figure 5C:
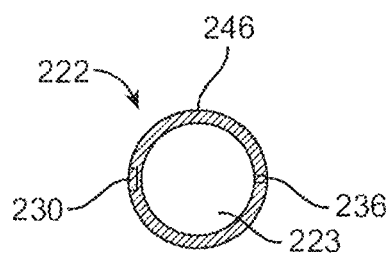
FIG. 5C is a cross-sectional view of the spined distal access catheter taken along line C-C of FIG. 5B.
Figure 5D:
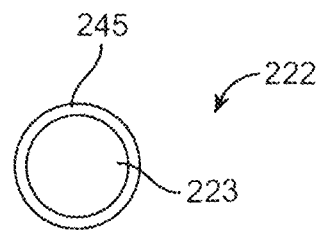
FIG. 5D is a cross-sectional view of the spined distal access catheter taken along line D-D of FIG. 5B.
Figure 5E:
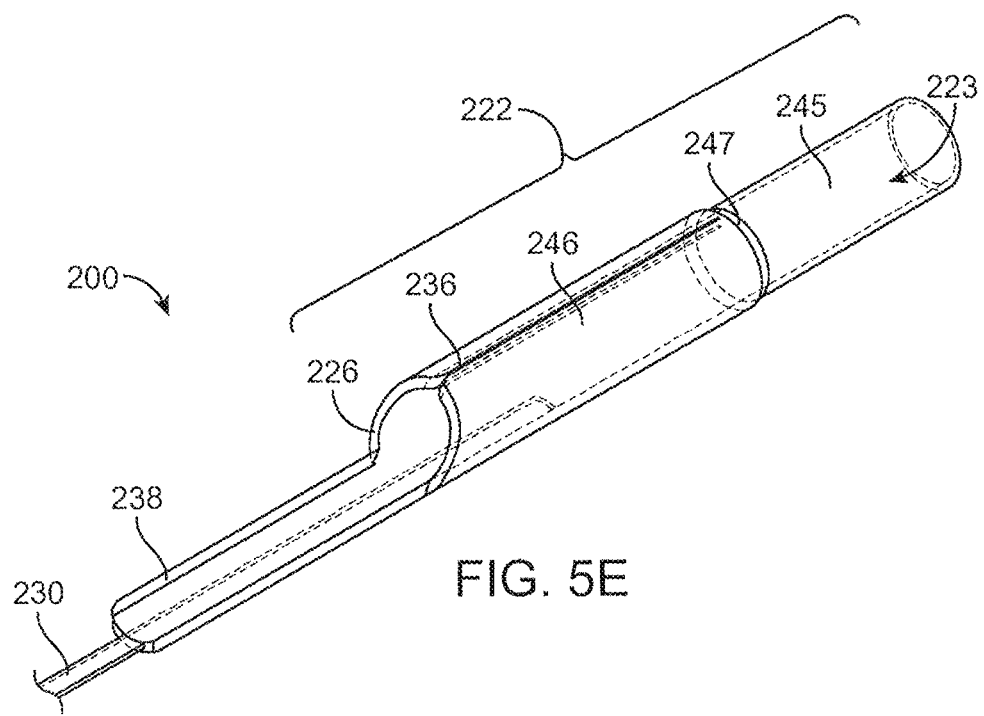
FIGS. 5E-5F are partial perspective views of the spined distal access catheter of FIG. 5A.
Figure 5F:
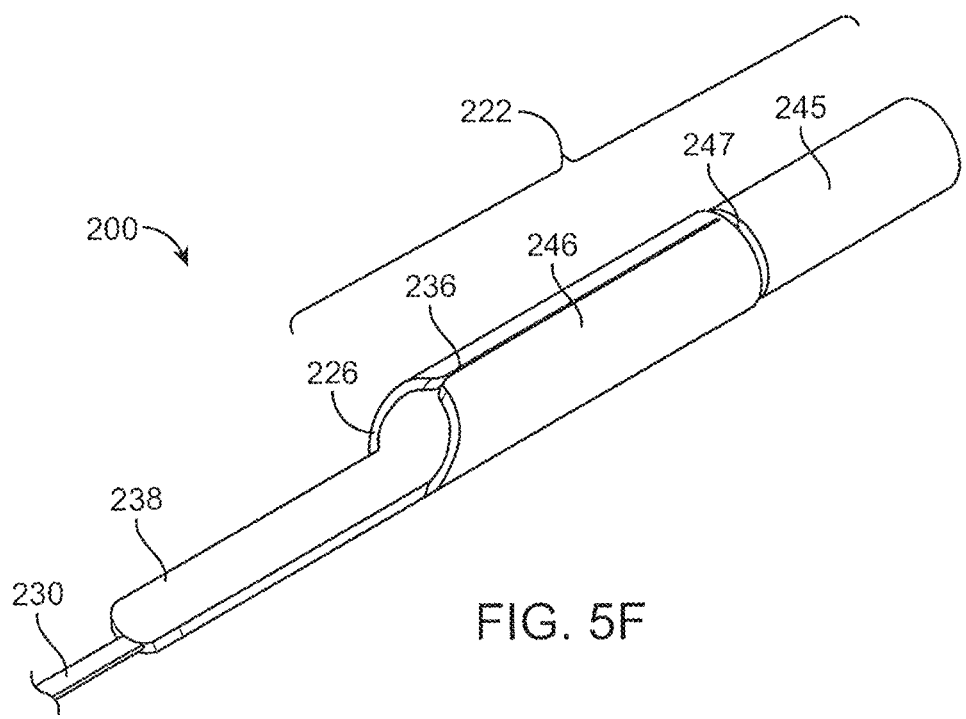
Figure 6A:
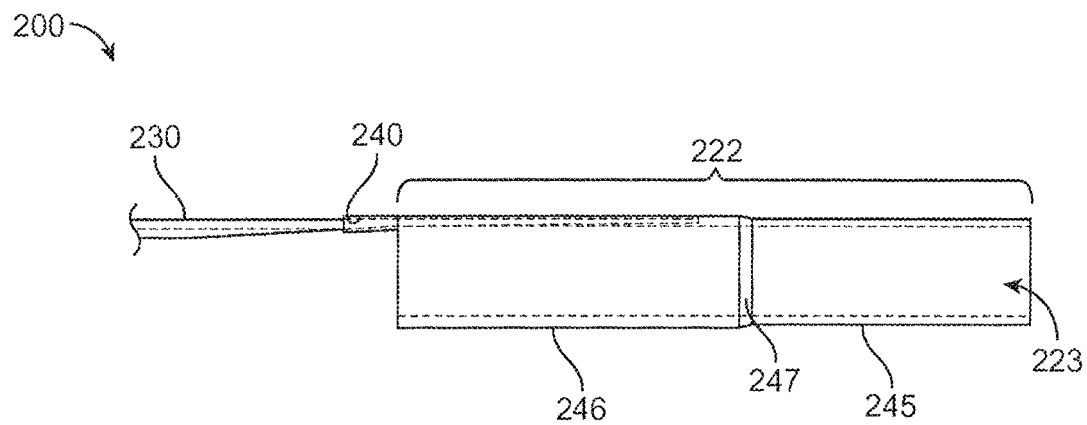
FIG. 6A is a side elevational view of an implementation of a spined distal access catheter.
Figure 6B:
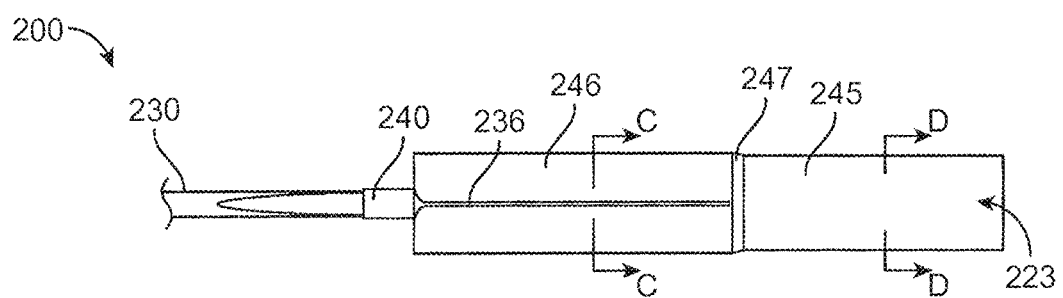
FIG. 6B is a top plan view of the spined distal access catheter of FIG. 6A.
Figure 6C:
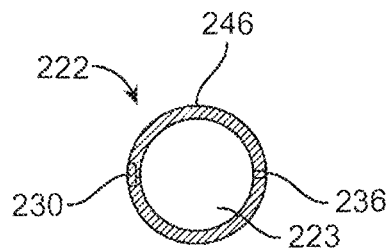
FIG. 6C is a cross-sectional view of the spined distal access catheter taken along line C-C of FIG. 6B.
Figure 6D:
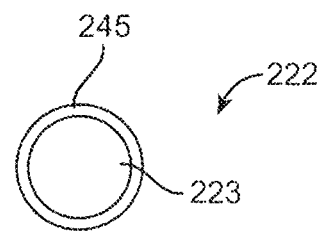
FIG. 6D is a cross-sectional view of the spined distal access catheter taken along line D-D of FIG. 6B.
Figure 6E:
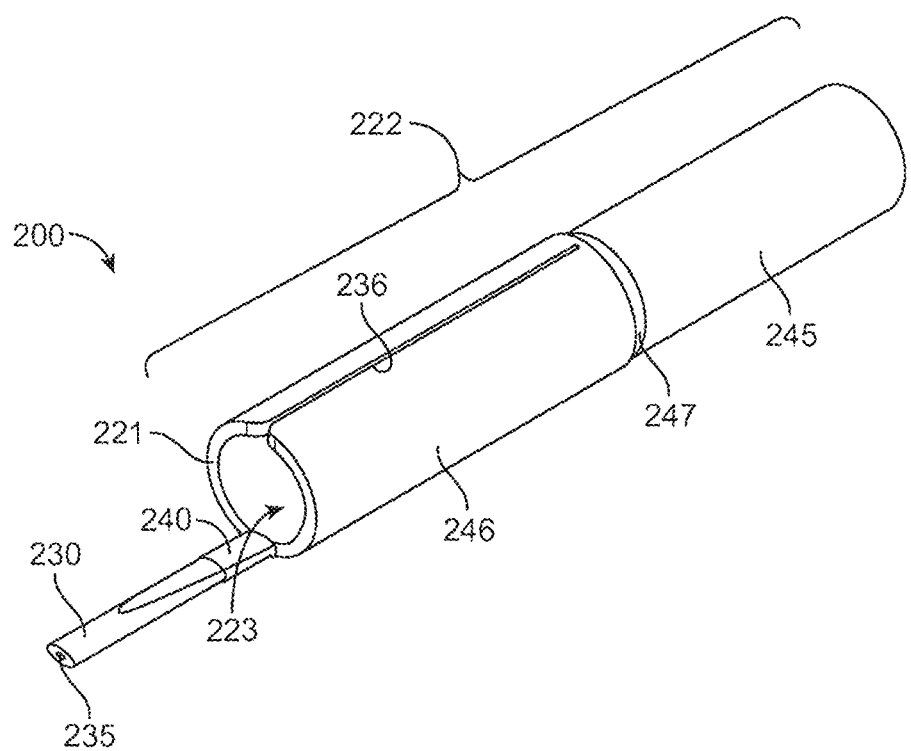
FIGS. 6E-6F are partial perspective views of the spined distal access catheter of FIG. 6A.
Figure 6F:
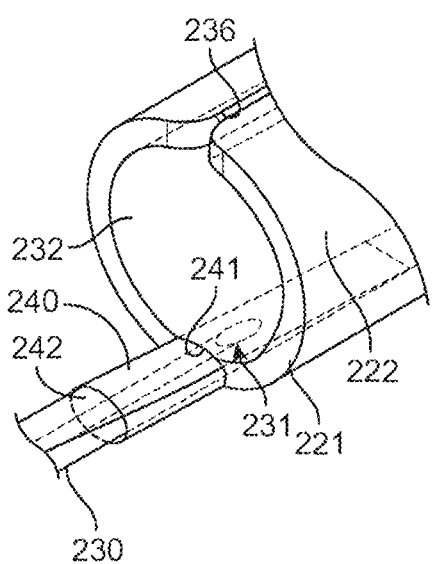

The luminal portion 222 of the catheter 200 can have a uniform diameter or wall thickness from a proximal end to a distal end or the luminal portion 222 can have different outer diameters or wall thicknesses along its length. For example, the distal-most end of the distal luminal portion 222 can have a smaller outer diameter compared to a more proximal region of the distal luminal portion 222. FIGS. 5A-5B, 5E-5F as well as FIGS. 6A-6B, 6E-6F, and FIG. 8A show a distal luminal portion 222 having a distal tubular region or distal tube 245 having a smaller outer diameter and a proximal tubular region or proximal tube 246 have a larger outer diameter. The distal tube 245 transitions via a step-up 247 to the proximal tube 246. As best shown in FIGS. 5A and 6A, the inner diameters of distal tube 245 and the proximal tube 246 are substantially the same providing a smooth inner wall surface for the lumen 223. The outer diameter of the distal tube 245 may be smaller than the outer diameter of the proximal tube 246. The step-up 247 is formed by a transition in wall thickness between the distal tube 245 and the proximal tube 246. In some implementations, the outer diameter of the distal tube 245 can be about 0.080" to about 0.084" and the outer diameter of the proximal tube 246 can be about 0.087" to about 0.088". In other implementations, the outer diameter of the proximal tube 246 can be 0.106" to about 0.107". The relative lengths of the proximal and distal tubes 245, 246 may vary as described elsewhere herein. For example, the proximal tube 246 can create a proximal sealing zone that is a cylindrical segment having a length that is about 1 mm, 2 mm, 3 mm, 4 mm, 5 mm, up to about 10 mm, or 15 mm. The proximal sealing zone of the proximal tube 246 may have a larger OD compared to the OD of the distal tube. In some implementations, the distal tube may have an OD that is about 0.082", the proximal tube 246 at the proximal sealing zone may have an OD that is about 0.087". In other implementations, where the distal tube may have an OD that is about 0.102", and the proximal tube 246 at the proximal sealing zone may have an OD that is about 0.105".

At least a portion of the wall of the larger outer diameter proximal tube 246 can be discontinuous such that it includes a slit 236 (see FIGS. 5A-5C, 5E-5F, 6A-6C, and 6E-6F). The slit 236 can extend a distance along the length of the proximal tube 246. The slit 236 can extend from an edge 221 of the proximal tube 246 at least about 2 cm of a length of the proximal tube 246. The slit 236 can, but need not, extend along the entire length of the proximal tube 246 to the location of the step-up 247. Additionally, the proximal tube 246 can include more than one slit 236. The slit 236 can be positioned in the larger diameter proximal tube 246 at a location opposite from where the distal end of the proximal control element 230 couples with the wall of the distal luminal portion 222. As such that distal end of the proximal control element 230 embedded within the wall of the proximal tube 246 lies opposite the slit 236 (see FIGS. 5C and 6C). The slit 236 can be positioned around the proximal tube 246 at another location.

The slit 236 can allow for the proximal tube 246 to expand slightly such that the ends of the wall forming the slit 236 separate forming a gap therebetween. For example, upon insertion of the catheter 200 through the working lumen of the sheath 400, the outer diameter can be received in a sliding fit such that at least an overlap region 348 remains. Upon application of an aspirational force through the working lumen, for example, by applying suction from an aspiration source coupled to the proximal end 403 of the guide sheath 400, the sealing provided at the overlap region 348 can be enhanced by a slight widening of the gap formed by the slit 236. This slight expansion provides for better sealing between the outer diameter of the proximal tube 246 and the inner diameter of the working lumen of the sheath 400 because the outer surface of the walls of the catheter 200 can press against the inner surface of the working lumen creating a tight fit between the catheter 200 and the sheath 400. This improved sealing between the outer surface of the catheter 200 and the inner surface of the working lumen minimizes the seepage of blood from the vessel into the working lumen directly through the distal opening 408. Thus, the larger outer diameter of the proximal tube 246 in combination with the slit 236 can enhance sealing between the catheter 200 and the sheath 400 by accommodating for variations of sheath inner diameters. The slit 236 can effectively increase the outer diameter of the proximal tube 246 depending on whether the walls forming the slit 236 are separated a distance. The walls forming the slit 236 can separate away from one another and increase a width of slit. The outer diameter of the proximal tube 246 including the increased width upon separation of the walls forming the slit 236 can be the same size or larger than the inner diameter of the sheath through which the proximal tube 246 is inserted. This allows for a single catheter to be compatible with a larger range of inner diameters. In some implementations, the outer diameter of the proximal tube 246 can be 0.081" or about 0.100" when the walls forming the slit 236 abut one another and no gap is present. The outer diameter of the proximal tube 246 can increase up to about 0.087" or up to about 0.106" when the walls forming the slit 236 are separated a maximum distance away from one another. Additionally, the increased wall thickness of the proximal tube 246 allows for creating a more robust joint between the distal luminal portion 222 and the proximal control element 230 of the catheter.

Additionally or alternatively, the distal tip 406 of the sheath 400 can include one or more features that improve sealing between the inner diameter of the working lumen of the sheath 400 and the outer diameter of the proximal end region of the catheter 200.

Catheter Advancement Element

The distal access system 100 can, but need not, include a catheter advancement element 300 for delivery of the catheter 200 to the distal anatomy. Similarly, the catheter advancement element 300 can be used together to advance other catheters besides the catheter 200 described herein. For example, the catheter advancement element 300 can be used to deliver a 5MAX Reperfusion Catheter (Penumbra, Inc. Alameda, Calif.) for clot removal in patients with acute ischemic stroke or other reperfusion catheters known in the art. Although the catheter advancement element 300 is described herein in reference to catheter 200 it can be used to advance other catheters and it is not intended to be limiting to its use.

The distal access system 100 is capable of providing quick and simple access to distal target anatomy, particularly the tortuous anatomy of the cerebral vasculature. The flexibility and deliverability of the distal access catheter 200 allow the catheter 200 to take the shape of the tortuous anatomy and avoids exerting straightening forces creating new anatomy. The distal access catheter 200 is capable of this even in the presence of the catheter advancement element 300 extending through its lumen. Thus, the flexibility and deliverability of the catheter advancement element 300 is on par or better than the flexibility and deliverability of the distal luminal portion 222 of the distal access catheter 200 in that both are configured to reach the middle cerebral artery (MCA) circulation without straightening out the curves of the anatomy along the way.

The catheter advancement element 300 can include a non-expandable, flexible elongate body 360 coupled to a proximal portion 366. The catheter advancement element 300 and the catheter 200 described herein may be configured for rapid exchange or over-the-wire methods. For example, the flexible elongate body 360 can be a tubular portion extending the entire length of the catheter advancement element 300 and can have a proximal opening from the lumen of the flexible elongate body 360 that is configured to extend outside the patient's body during use. Alternatively, the tubular portion can have a proximal opening positioned such that the proximal opening remains inside the patient's body during use. The proximal portion 366 can be a proximal element coupled to a distal tubular portion and extending proximally therefrom. A proximal opening from the tubular portion can be positioned near where the proximal element couples to the tubular portion. Alternatively, the proximal portion 366 can be a proximal extension of the tubular portion having a length that extends to a proximal opening near a proximal terminus of the catheter advancement element 300 (i.e. outside a patient's body).

The configuration of the proximal portion 366 can vary. In some implementations, the proximal portion 366 is simply a proximal extension of the flexible elongate body 360 that does not change significantly in structure but in flexibility. For example, the proximal portion 366 transitions from the very flexible distal regions of the catheter advancement element 300 towards less flexible proximal regions of the catheter advancement element 300. The proximal portion 366 provides a relatively stiff proximal end suitable for manipulating and torqueing the more distal regions of the catheter advancement element 300. In other implementations, the proximal portion 366 is a hypotube. The hypotube may be exposed or may be coated by a polymer. In still further implementations, the proximal portion 366 may be a polymer portion reinforced by a coiled ribbon. The proximal portion 366 can have the same outer diameter as the flexible elongate body or can have a smaller outer diameter as the flexible elongate body.

The proximal portion 366 need not include a lumen. For example, the proximal portion 366 can be a solid rod, ribbon, or wire have no lumen extending through it that couples to the tubular elongate body 360. Where the proximal portion 366 is described herein as having a lumen, it should be appreciated that the proximal portion 366 can also be solid and have no lumen. The proximal portion 366 is generally less flexible than the elongate body 360 and can transition to be even more stiff towards the proximal-most end of the proximal portion 366. Thus, the catheter advancement element 300 can have an extremely soft and flexible distal-most tip that transitions proximally to a stiff proximal portion 366 well suited for torqueing and pushing the distal elongate body 360. The transition in flexibility of the catheter advancement element 300 and the system as a whole is described in more detail below and in the Examples.

The elongate body 360 can be received within and extended through the internal lumen 223 of the distal luminal portion 222 of the catheter 200 (see FIG. 2B). The elongate body 360 or tubular portion can have an outer diameter. The outer diameter of the tubular portion can have at least one snug point, a difference between the inner diameter of the catheter 200 and the outer diameter of the tubular portion at the snug point can be no more than about 0.010", for example, from 0.003" up to about 0.010", preferably about 0.006" to about 0.008". As will be described in more detail below, the catheter advancement element 300 can also include a tip portion or distal tip 346 located distal to the at least one snug point of the tubular portion. The tip portion can have a length and taper along at least a portion of the length. The distal tip 346 of the catheter advancement element 300 can be extended beyond the distal end of the catheter 200 as shown in FIG. 2B. The proximal portion 366 of the catheter advancement element 300 or proximal extension is coupled to a proximal end region of the elongate body 360 and extends proximally therefrom. The proximal portion 366 can be less flexible than the elongate body 360 and configured for bi-directional movement of the elongate body 360 of the catheter advancement element 300 within the luminal portion 222 of the catheter 200, as well as for movement of the catheter system 100 as a whole. The elongate body 360 can be inserted in a coaxial fashion through the internal lumen 223 of the luminal portion 222. The outer diameter of at least a region of the elongate body 360 can be sized to substantially fill at least a portion of the internal lumen 223 of the luminal portion 222.

The overall length of the catheter advancement element 300 (e.g. between the proximal end through to the distal-most tip) can vary, but generally is long enough to extend through the support catheter 200 plus at least a distance beyond the distal end of the support catheter 200 while at least a length of the proximal portion 366 remains outside the proximal end of the guide sheath 400 and outside the body of the patient. In some implementations, the overall length of the catheter advancement element 300 is about 145 to about 150 cm and has a working length of about 140 cm to about 145 cm from a proximal tab or hub to the distal-most tip. The elongate body 360 can have a length that is at least as long as the luminal portion 222 of the catheter 200 although the elongate body 360 can be shorter than the luminal portion 222 so long as at least a minimum length remains inside the luminal portion 222 when a distal portion of the elongate body 360 is extended distal to the distal end of the luminal portion 222 to form a snug point or snug region with the catheter. In some implementations, this minimum length of the elongate body 360 that remains inside the luminal portion 222 when the distal tip 346 is positioned at its optimal advancement configuration is at least about 5 cm, at least about 6 cm, at least about 7 cm, at least about 8 cm, at least about 9 cm, at least about 10 cm, at least about 11 cm, or at least about 12 cm up to about 50 cm. In some implementations, the shaft length of the distal luminal portion 222 can be about 35 cm up to about 75 cm and shorter than a working length of the guide sheath and the insert length of the elongate body 360 can be at least about 45 cm, 46 cm, 47 cm, 48 cm, 48.5 cm, 49 cm, 49.5 cm up to about 85 cm.

The length of the elongate body 360 can allow for the distal end of the elongate body 360 to reach cerebrovascular targets within, for example, the M1 or M2 regions while the proximal end region of the elongate body 360 remains proximal to or below the level of severe turns along the path of insertion. For example, the entry location of the catheter system can be in the femoral artery and the target embolus can be distal to the right common carotid RCC artery, such as within the M1 segment of the middle cerebral artery on the right side. The proximal end region of the elongate body 360 where it transitions to the proximal portion 366 can remain within a vessel that is proximal to severely tortuous anatomy such as the carotid siphon, the right common carotid RCC artery, the brachiocephalic trunk BT, the take-off into the brachiocephalic artery from the aortic arch, the aortic arch AA as it transitions from the descending aorta DA. This avoids inserting the stiffer proximal portion 366, or the material transition between the stiffer proximal portion 366 and the elongate body 360, from taking the turn of the aortic arch or the turn of the brachiocephalic take-off from the aortic arch, which both can be very severe. The lengths described herein for the distal luminal portion 222 also can apply to the elongate body 360 of the catheter advancement element.

The proximal portion 366 can have a length that varies as well. In some implementations, the proximal portion 366 is about 90 cm up to about 95 cm. The distal portion extending distal to the distal end of the luminal portion 222 can include distal tip 346 that protrudes a length beyond the distal end of the luminal portion 222 during use of the catheter advancement element 300. The distal tip 346 of the elongate body 360 that is configured to protrude distally from the distal end of the luminal portion 222 during advancement of the catheter 200 through the tortuous anatomy of the cerebral vessels, as will be described in more detail below. The proximal portion 366 coupled to and extending proximally from the elongate body 360 can align generally side-by-side with the proximal control element 230 of the catheter 200. The arrangement between the elongate body 360 and the luminal portion 222 can be maintained during advancement of the catheter 200 through the tortuous anatomy to reach the target location for treatment in the distal vessels and aids in preventing the distal end of the catheter 200 from catching on tortuous branching vessels, as will be described in more detail below.

In some implementations, the elongate body 360 can have a region of relatively uniform outer diameter extending along at least a portion of its length and the distal tip 346 tapers down from the uniform outer diameter. The outer diameter of the elongate body 360 can include a step-down at a location along its length, for example, a step-down in outer diameter at a proximal end region where the elongate body 360 couples to the proximal portion 366. Depending upon the inner diameter of the catheter 200, the clearance between the catheter 200 and the outer diameter of the elongate body 360 along at least a portion of its length can be no more than about 0.010", such as within a range of about 0.003"-0.010" or between 0.006"-0.008".

The elongate body 360 can have an overall shape profile from proximal end to distal end that transitions from a first outer diameter having a first length to a tapering outer diameter having a second length. The first length of this first outer diameter region (i.e. the snug-fitting region between the distal luminal portion 222 and the elongate body 360) can be at least about 5 cm, or 10 cm, up to about 50 cm. The length of the tapering outer diameter can be between 1 cm and 4 cm. When the catheter advancement element 300 is inserted through the catheter 200, this tapered distal tip 346 is configured to extend beyond and protrude out through the distal end of the luminal portion 222 whereas the more proximal region of the body 360 (i.e. the first length described above) remains within the luminal portion 222.

As mentioned, the distal end of the luminal portion 222 can be blunt and have no change in the dimension of the outer diameter whereas the distal tip 346 can be tapered providing an overall elongated tapered geometry of the catheter system. The outer diameter of the elongate body 360 also approaches the inner diameter of the luminal portion 222 such that the step-up from the elongate body 360 to the outer diameter of the luminal portion 222 is minimized. Minimizing this step-up prevents issues with the lip formed by the distal end of the luminal portion 222 catching on the tortuous neurovasculature, such as around the carotid siphon near the ophthalmic artery branch, when the distal tip 346 in combination with the distal end region of the catheter 200 bends and curves along within the vascular anatomy. In some implementations, the inner diameter of the luminal portion 222 can be at least about 0.052", about 0.054" and the maximum outer diameter of the elongate body 360 can be about 0.048" such that the difference between them is about 0.006". In some implementations, the inner diameter of the luminal portion 222 can be about 0.070" and the maximum outer diameter of the elongate body 360 can be about 0.062" such that the difference between them is about 0.008". In some implementations, the inner diameter of the luminal portion 222 can be about 0.088" and the maximum outer diameter of the elongate body 360 can be about 0.080" such that the difference between them is about 0.008". In some implementations, the inner diameter of the luminal portion 222 can be about 0.072" and the maximum outer diameter of the elongate body 360 is about 0.070" such that the difference between them is only 2 thousandths of an inch. In other implementations, the maximum outer diameter of the elongate body 360 is about 0.062" such that the difference between them is about 0.010". Despite the outer diameter of the elongate body 360 extending through the lumen of the luminal portion 222, the luminal portion 222 and the elongate body 360 extending through it in co-axial fashion are flexible enough to navigate the tortuous anatomy leading to the level of M1 or M2 arteries without kinking and without damaging the vessel.

The dimensions provided herein are approximate and each dimensions may have an engineering tolerance or a permissible limit of variation. Use of the term "about" or "approximately" are intended to provide such permissible tolerance to the dimension being referred to. Where "about" or "approximately" is not used with a particular dimension herein that that dimension need not be exact.

The length of the distal tip 346 (e.g. the region of the catheter advancement element 300 configured to extend distal to the distal end of the catheter 200 during use to obtain the optimum advancement configuration) can vary. In some implementations, the length of the distal tip 346 can be in a range of between about 0.50 cm to about 4.0 cm from the distal-most terminus of the elongate body 360 or between about 1.0 cm to about 3.0 cm. In other implementations, the length of the distal tip 346 is between 2.0 cm to about 2.5 cm. In some implementations, the length of the distal tip 346 varies depending on the inner diameter of the catheter 200 with which the catheter advancement element 300 is to be used. For example, the length of the distal tip 346 can be as shorter (e.g. 1.2 cm) for a catheter advancement element 300 sized to be used with a catheter 200 having an inner diameter of about 0.054" and can be longer (e.g. 2.5 cm) for a catheter advancement element 300 sized to be used with a catheter 200 having an inner diameter of about 0.088". The distal tip 346 can be a constant taper from the outer diameter of the elongate body 360 (e.g. the distal end of the marker 344b) down to a second smaller outer diameter at the distal-most terminus (e.g. the proximal end of the marker 344a) as shown in FIG. 7C. In some implementations, the constant taper of the distal tip 346 can be from about 0.048" outer diameter down to about 0.031" outer diameter over a length of about 1 cm. In some implementations, the constant taper of the distal tip 346 can be from 0.062" outer diameter to about 0.031" outer diameter over a length of about 2 cm. In still further implementations, the constant taper of the distal tip 346 can be from 0.080" outer diameter to about 0.031" outer diameter over a length of about 2.5 cm. The length of the constant taper of the distal tip 346 can vary, for example, between 0.8 cm to about 2.5 cm, or between 1 cm and 3 cm, or between 2.0 cm and 2.5 cm. The angle of the taper can vary depending on the outer diameter of the elongate body 360. For example, the taper can be between 0.9 to 1.6 degree angle relative to horizontal. The taper can be between 2-3 degree angle from a center line of the elongate body 360.

The catheter advancement element 300 can include a distal tip 346 that tapers over a length. The elongate body 360 of the catheter advancement element 300 can have an inner diameter that does not change over its length even in the presence of the tapering of the distal tip 346. Thus, the inner diameter of the lumen extending through the tubular portion of the catheter advancement element 300 can remain uniform and the wall thickness of the distal tip 346 can decrease to provide the taper. The wall thickness can thin distally along the length of the taper. Thus, the material properties in combination with wall thickness, angle, length of the taper can all contribute to the overall maximum flexibility of the distal-most end of the distal tip 346. The catheter advancement element 300 undergoes a transition in flexibility from the distal-most end towards the snug point where it achieves an outer diameter that is no more than about 0.010" different from the inner diameter of the catheter 200.

The distal tip 346 need not taper and can achieve its soft, atraumatic and flexible characteristic due to a material property other than due to a change in outer dimension to facilitate endovascular navigation to an embolus in tortuous anatomy. Additionally or alternatively, the distal tip 346 of the elongate body 360 can have a transition in flexibility along its length. The most flexible region of the distal tip 346 can be its distal terminus. Moving along the length of the distal tip 346 from the distal terminus towards a region proximal to the distal terminus. For example, the distal tip 346 can be formed of a material having a material hardness of no more than 35 D or about 62 A and transitions proximally to be less flexible near where it is formed of a material having a material hardness of no more than 55 D and 72 D up to the proximal portion 366, which can be a stainless steel hypotube, or a combination of a material property and tapered shape. The materials used to form the regions of the elongate body 360 can include PEBAX (such as PEBAX 25D, 35D, 55D, 72D) with a lubricious additive compound, such as Mobilize (Compounding Solutions, Lewiston, Me.). In some implementations, the material used to form a region of the elongate body 360 can be Tecothane 62A. Incorporation of a lubricious additive directly into the polymer elongate body means incorporation of a separate lubricious liner, such as a Teflon liner, is unnecessary. This allows for a more flexible element that can navigate the distal cerebral anatomy and is less likely to kink. Similar materials can be used for forming the distal luminal portion 222 of the catheter 200 providing similar advantages. The flexibility of the distal tip 346 can be achieved by a combination of flexible lubricious materials and tapered shapes. For example, the length of the tip 346 can be kept shorter than 2 cm-3 cm, but maintain optimum deliverability due to a change in flexible material from distal-most tip towards a more proximal region a distance away from the distal-most tip. In an implementation, the elongate body 360 is formed of PEBAX (polyether block amide) embedded silicone designed to maintain the highest degree of flexibility. The wall thickness of the distal end of the luminal portion 222 can also be made thin enough such that the lip formed by the distal end of the luminal portion 222 relative to the elongate body 360 is minimized.

The elongate body 360 has a benefit over a microcatheter in that it can have a relatively large outer diameter that is just 0.003"-0.010" smaller than the inner diameter of the distal luminal portion 222 of the catheter 200 and still maintaining a high degree of flexibility for navigating tortuous anatomy. When the gap between the two components is too tight (e.g. less than about 0.003"), the force needed to slide the catheter advancement element 300 relative to the catheter 200 can result in damage to one or both of the components and increases risk to the patient during the procedure. The gap results in too tight of a fit to provide optimum relative sliding. When the gap between the two components is too loose (e.g. greater than about 0.010"), the distal end of the catheter 200 forms a lip that is prone to catch on branching vessels during advancement through tortuous neurovasculature, such as around the carotid siphon where the ophthalmic artery branches off.

The gap in ID/OD between the elongate body 360 and the distal luminal portion 222 can be in this size range (e.g. 0.003"-0.010") along a majority of their lengths. For example, the elongate body 360 can have a relatively uniform outer diameter that is between about 0.048" to about 0.080" from a proximal end region to a distal end region up to a point where the taper of the distal tip 346 begins. Similarly, the distal luminal portion 222 of the catheter 200 can have a relatively uniform inner diameter that is between about 0.054" to about 0.088" from a proximal end region to a distal end region. As such, the difference between their respective inner and outer diameters along a majority of their lengths can be within this gap size range of 0.003" to 0.010". The distal tip 346 of the elongate body 360 that is tapered will have a larger gap size relative to the inner diameter of the distal luminal portion 222. During use, however, this tapered distal tip 346 is configured to extend distal to the distal end of the catheter 200 such that the region of the elongate body 360 having an outer diameter sized to match the inner diameter of the distal luminal portion 222 is positioned within the lumen of the catheter 200 such that it can minimize the lip at the distal end of the catheter 200.

The elongate body 360 can be formed of various materials that provide a suitable flexibility and lubricity. Example materials include high density polyethylene, 72D PEBAX, 90D PEBAX, or equivalent stiffness and lubricity material. At least a portion of the elongate body 360 can be reinforced to improve navigation and torqueing (e.g. braided reinforcement layer). The flexibility of the elongate body 360 can increase towards the distal tip 346 such that the distal region of the elongate body 360 is softer, more flexible, and articulates and bends more easily than a more proximal region. For example, a more proximal region of the elongate body can have a bending stiffness that is flexible enough to navigate tortuous anatomy such as the carotid siphon without kinking. If the elongate body 360 has a braid reinforcement layer along at least a portion of its length, the braid reinforcement layer can terminate a distance proximal to the distal tip 346. For example, the distance from the end of the braid to the distal tip can be about 10 cm to about 15 cm or from about 4 cm to about 10 cm or from about 4 cm up to about 15 cm.

Figure 7A:
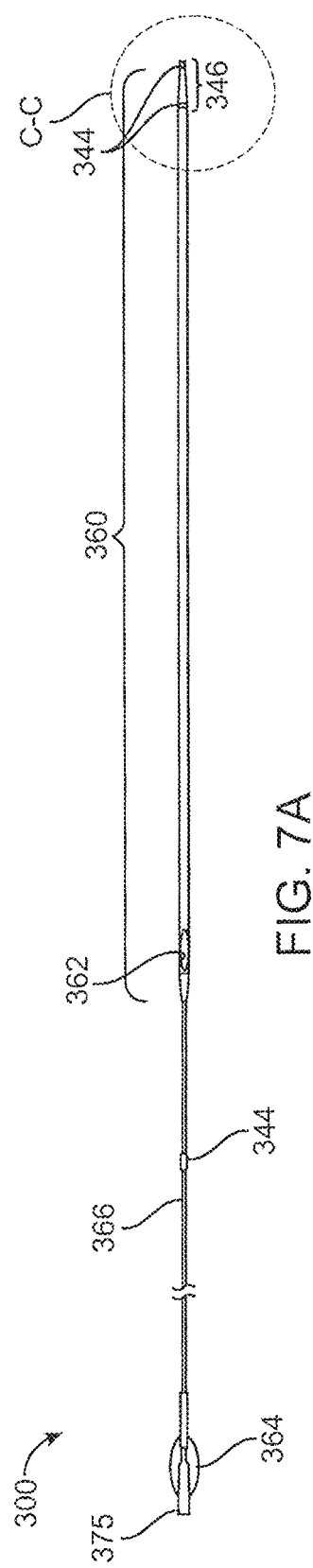
FIG. 7A is a side view of an implementation of a catheter advancement element.
Figure 7B:
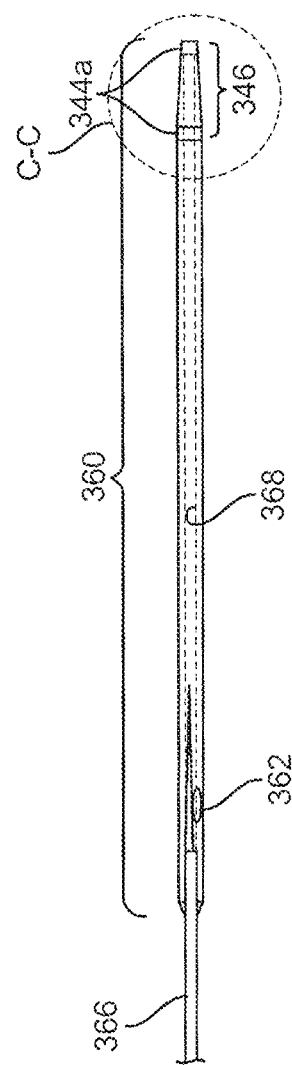
FIG. 7B is a cross-sectional view of the catheter advancement element of FIG. 7A.
Figure 7C:
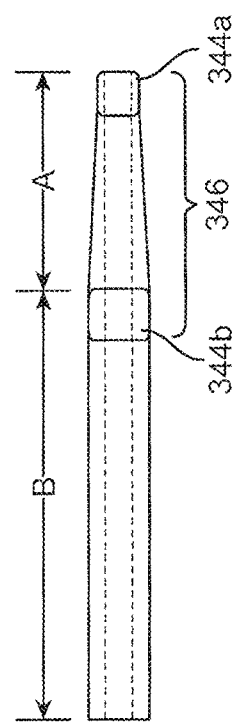
FIG. 7C is a detail view of FIG. 7B taken along circle C-C.
Figure 10A:
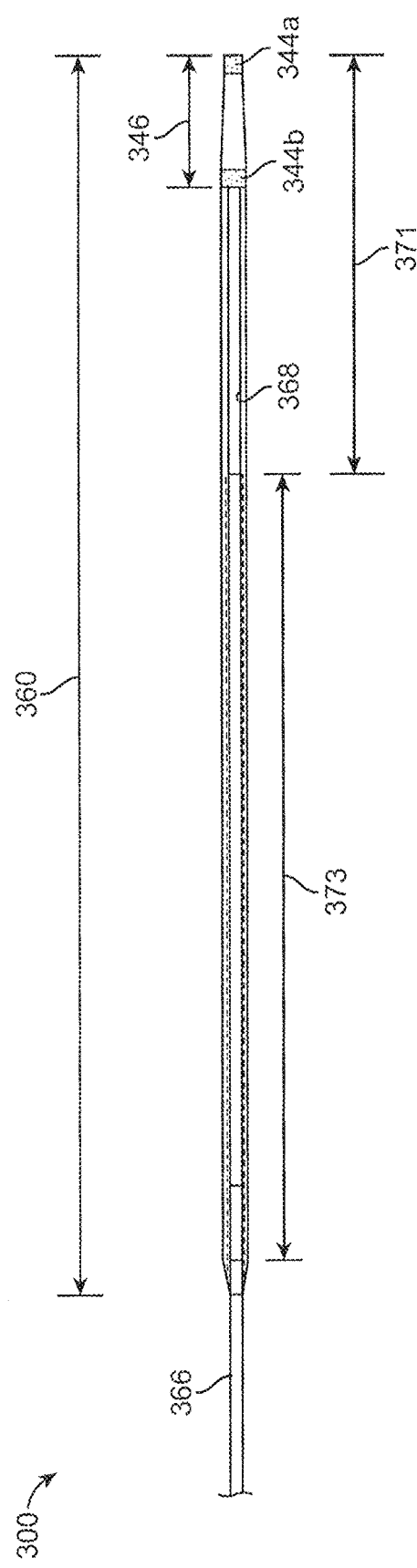
FIG. 10A is a schematic cross-sectional view of an implementation of a catheter advancement element.
Figure 10B:
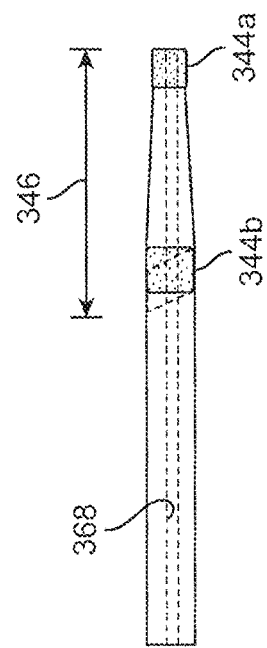
FIG. 10B is a schematic cross-sectional view of a distal end region of the catheter advancement element of FIG. 10A.
Figure 10C:
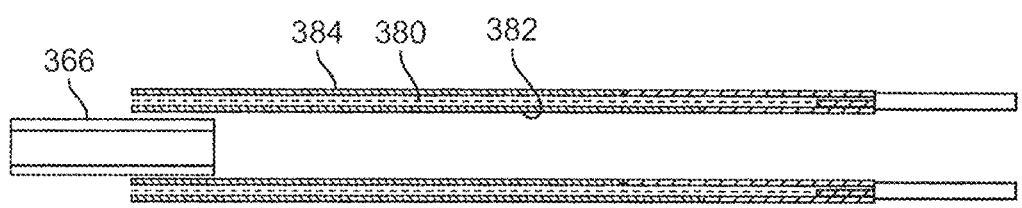
FIG. 10C is a schematic cross-sectional view of a middle region of the catheter advancement element of FIG. 10A.

In some implementations, the elongate body 360 can be generally tubular along at least a portion of its length such that it has a single lumen 368 extending parallel to a longitudinal axis of the catheter advancement element 300 (see FIG. 7A-7C and also FIG. 10A-10C). In an implementation, the single lumen 368 of the elongate body 360 is sized to accommodate a guidewire, however use of the catheter advancement element 300 generally eliminates the need for a guidewire lead. Methods of using the catheter advancement element 300 without a guidewire to deliver a catheter to distal regions of the brain are described in more detail below.

A guidewire can extend through the single lumen 368 generally concentrically from a proximal opening to a distal opening through which the guidewire can extend. In some implementations, the proximal opening is at the proximal end of the catheter advancement element 300 such that the catheter advancement element 300 is configured for over-the-wire (OTW) methodologies. In other implementations, the proximal opening is a rapid exchange opening 362 through a wall of the catheter advancement element 300 such that the catheter advancement element 300 is configured for rapid exchange rather than or in addition to OTW. In this implementation, the proximal opening 362 extends through the sidewall of the elongate body and is located a distance away from a proximal tab 364 and distal to the proximal portion 366 (see FIGS. 7A-7B and 7D). The proximal opening 362 can be located a distance of about 10 cm from the distal tip 346 up to about 20 cm from the distal tip 346. In some implementations, the proximal opening 362 can be located near a region where the elongate body 360 is joined to the proximal portion 366, for example, just distal to an end of the hypotube (see FIG. 7B). In other implementations, the proximal opening 362 is located more distally such as about 10 cm to about 18 cm from the distal-most end of the elongate body 360 (see FIG. 7D). A proximal opening 362 that is located closer to the distal tip 346 allows for easier removal of the catheter advancement element 300 from the catheter 200 leaving the guidewire in place for a "rapid exchange" type of procedure. Rapid exchanges can rely on only a single person to perform the exchange. The catheter advancement element 300 can be readily substituted for another device using the same guidewire that remains in position. The single lumen 368 of the elongate body 360 can be configured to receive a guidewire in the range of 0.014" and 0.018" diameter, or in the range of between 0.014" and 0.022". In this implementation, the inner luminal diameter of the elongate body 360 can be between 0.020" and 0.024". The guidewire, the catheter advancement element 300, and the catheter 200 can all be assembled co-axially for insertion through the working lumen of the guide sheath 400. The inner diameter of the lumen 368 of the elongate body 360 can be 0.019" to about 0.021".

Figure 7D:
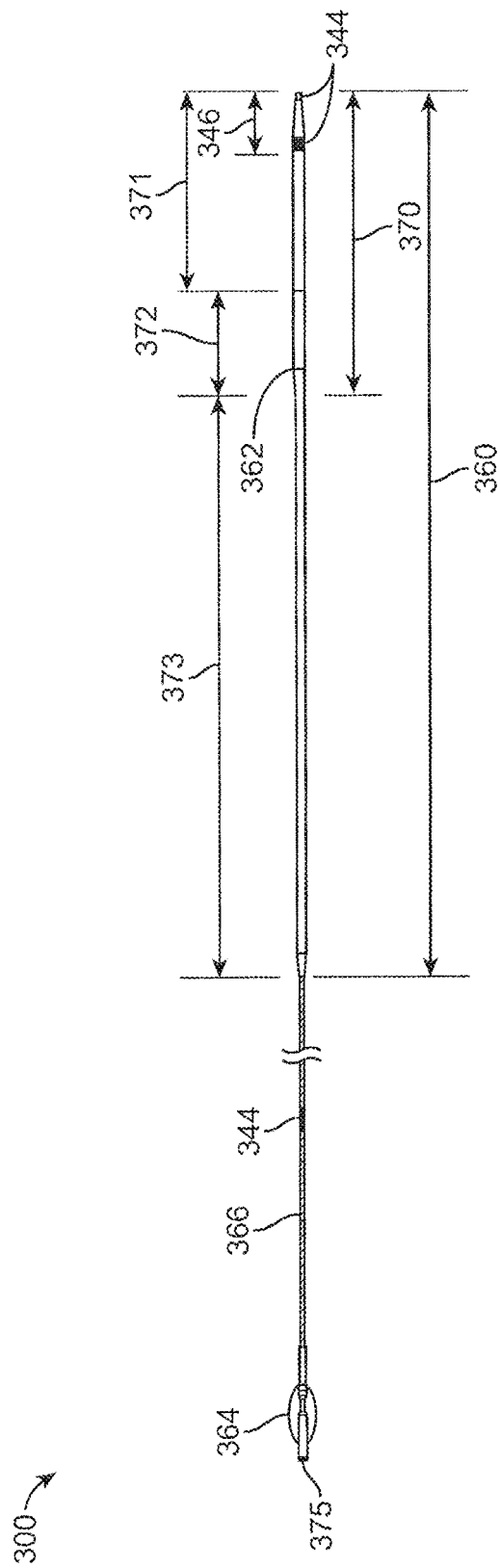
FIG. 7D is a side view of another implementation of a catheter advancement element.

FIG. 7D shows another implementation of the catheter advancement element 300 configured for rapid exchange. Rapid exchange configurations can dramatically shorten device length, decreases staffing requirements, and reduces fluoroscopy. As with other implementations described herein, the catheter advancement element 300 can include a non-expandable, flexible elongate body 360 coupled to a proximal portion 366 coupled to a proximal tab 364 or hub 375. The region near the distal tip 346 can be tapered such that the outer diameter tapers over a length of about 1 cm to about 4 cm. In some implementations, the distal taper length is 2.5 cm. In some implementations, the distal tip 346 tapers from about 0.080" to about 0.031". Also, the distal tip 346 can be formed of a material having a material hardness (e.g. 62 A and 35 D) that transitions proximally towards increasingly harder materials having (e.g. 55 D and 72 D) up to the proximal portion 366. For example, FIG. 7D illustrates segment 371 of the elongate body 360 including the distal tip 346 formed of a material having a material hardness of 35 D and a length of about 10 cm to about 12.5 cm. Segment 371 of the elongate body 360 including the distal tip 346 formed of a material having a material hardness of 62 A and a length of about 10 cm to about 12.5 cm. Segment 372 of the elongate body 360 formed of a material having a material hardness of 55 D and have a length of about 5 cm to about 8 cm. Segment 373 of the elongate body 360 formed of a material having a material hardness of 72 D can be about 25 cm to about 35 cm in length. The three segments 371, 372, 373 combined can form an insert length of the elongate body 360 from where the proximal portion 366 couples to the elongate body 360 to the terminus of the distal tip 346 that can be about 49 cm in length.

FIGS. 10A-10C illustrate an implementation of a catheter advancement element 300 incorporating a reinforcement layer 380. The reinforcement layer 380 can be a braid or other type of reinforcement to improve the torqueability of the catheter advancement element 300 and help to bridge the components of the catheter advancement element 300 having such differences in flexibility. The reinforcement layer 380 can bridge the transition from the rigid, proximal portion 366 to the flexible elongate body 360. In some implementations, the reinforcement layer 380 can be a braid positioned between inner and outer layers of Pebax 382, 384 (see FIG. 10C). The reinforcement layer 380 can terminate a distance proximal to the distal tip portion 346. For example, FIG. 10A illustrates the elongate body 360 having segment 371 and segment 373 located proximal to segment 371. Segment 371 can include the distal tip 346 formed of a material having a material hardness of at most about 35 D. Segment 371 is unreinforced polymer having a length of about 4 cm up to about 12.5 cm. Segment 373 of the elongate body 360 located proximal to segment 371 can include the reinforcement layer 380 and can extend a total of about 37 cm up to the unreinforced distal segment 371. A proximal end region of the reinforcement layer 380 can overlap with a distal end region of the proximal portion 366 such that a small overlap of hypotube and reinforcement exists near the transition between the proximal portion 366 and the elongate body 360.

Again with respect to FIG. 7D, an entry port 362 for a procedural guidewire can be positioned a distance away from the distal-most end of the elongate body 360. In some implementations, the entry/exit port 362 can be about 18 cm from the distal-most end creating a rapid exchange wire entry/exit segment 370. The outer diameter of the elongate body 360 within segment 370 (segments 371 and 372) can be about 0.080"-0.082" whereas segment 373 proximal to this rapid exchange wire entry/exit segment 370 can have a step-down in outer diameter such as about 0.062"-0.064".

The tubular portion of the catheter advancement element can have an outer diameter that has at least one snug point. A difference between the outer diameter at the snug point and the inner diameter of the lumen at the distal end of the distal, catheter portion can be no more than about 0.010". The at least one snug point of this tubular portion can be a point along the length of the tubular portion. The at least one snug point of this tubular portion can have a length that is at least about 5 cm up to about 50 cm, including for example, at least about 6 cm, at least about 7 cm, at least about 8 cm, at least about 9 cm, at least about 10 cm, at least about 11 cm, or at least about 12 cm up to about 50 cm. This length need not be uniform such that the length need not be snug alone its entire length. For example, the snug point region can include ridges, grooves, slits, or other surface features.

Figure 7E:
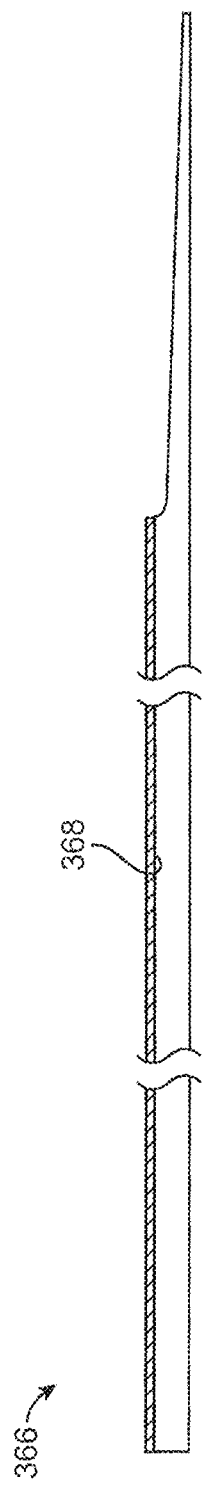
FIG. 7E is cross-sectional view of an implementation of a proximal portion the catheter advancement element of FIG. 7D.

In other implementations, the entire catheter advancement element 300 can be a tubular element configured to receive a guidewire through both the proximal portion 366 as well as the elongate body 360. For example, the proximal portion 366 can be a hypotube or tubular element having a lumen that communicates with the lumen 368 extending through the elongate body 360 (shown in FIG. 3). In some implementations, the proximal portion 366 can be a skived hypotube of stainless steel coated with PTFE having an outer diameter of 0.026". In other implementations, the outer diameter can be between 0.024" and 0.030". In some implementations, such as an over-the-wire version, the proximal portion 366 can be a skived hypotube coupled to a proximal hub 375. The proximal portion 366 can extend eccentric or concentric to the distal luminal portion 222. As best shown in FIG. 7E, the proximal portion 366 can be a stainless steel hypotube. The proximal portion 366 can be a solid metal wire that is round or oval cross-sectional shape. The proximal portion 366 can be a flattened ribbon of wire having a rectangular cross-sectional shape. The ribbon of wire can be curved into a circular, oval, c-shape, or quarter circle, or other cross-sectional shape along an arc. The proximal portion 366 can have any of variety of cross-sectional shapes whether or not a lumen extends therethrough, including a circular, oval, C-shaped, D-shape, or other shape. In some implementations, the proximal portion 366 is a hypotube having a D-shape such that an inner-facing side is flat and an outer-facing side is rounded. The rounded side of the proximal portion 366 can be shaped to engage with a correspondingly rounded inner surface of the sheath 400. The hypotube can have a lubricious coating such as PTFE. The hypotube can have an inner diameter of about 0.021", an outer diameter of about 0.0275", and an overall length of about 94 cm providing a working length for the catheter advancement element 300 that is about 143 cm. Including the proximal hub 375, the catheter advancement element 300 can have an overall length of about 149 cm. In some implementations, the hypotube can be a tapered part with a length of about 100 mm, starting proximal with a thickness of 0.3 mm and ending with a thickness of 0.10 mm to 0.15 mm. In still further implementations, the elongate body 360 can be a solid element coupled to the proximal portion 366 having no guidewire lumen.

The proximal portion 366 is shown in FIGS. 2A, 7A-7D, and 10A as having a smaller outer diameter compared to the outer diameter of the elongate body 360. The proximal portion 366 need not step down in outer diameter and can also have the same outer diameter as the outer diameter as the elongate body 360. For example, the proximal portion 366 can incorporate a hypotube or other stiffening element that is coated by one or more layers of polymer resulting in a proximal portion 366 having substantially the same outer diameter as the elongate body 360.

As best shown in FIGS. 7F-7J, the proximal end of the proximal portion 366 can be coupled to a proximal hub 375. The proximal hub 375 can be an over-molded component having a luer thread 377 and a luer taper 378 formed on an inside of the proximal hub 375. The proximal hub 375 can incorporate a tab 364 providing for easier gripping by a user. The proximal hub 375 prevents advancement of the catheter advancement element 300 and the catheter 200 beyond the distal tip of the base sheath 400 or guide catheter by limiting insertion into the proximal RHV 434 providing critical functional and safety features for proper operation of the system 10.

At least a portion of the solid elongate body 360, such as the elongate distal tip 346, can be formed of or embedded with or attached to a malleable material that skives down to a smaller dimension at a distal end. The distal tip 346 can be shaped to a desired angle or shape similar to how a guidewire may be used. The malleable length of the elongate body 360 can be at least about 1 cm, 3 cm, 5 cm, and up to about 10 cm, 15 cm, or longer. In some implementations, the malleable length can be about 1%, 2%, 5%, 10%, 20%, 25%, 50% or more of the total length of the elongate body 360. In some implementations, the catheter advancement element 300 can have a working length of about 140 cm to about 143 cm and the elongate body 360 can have an insert length of about 49 cm. The insert length can be the PEBAX portion of the elongate body 360 that is about 49.5 cm. As such, the malleable length of the elongate body 360 can be between about 0.5 cm to about 25 cm or more. The shape change can be a function of a user manually shaping the malleable length prior to insertion or the tip can be pre-shaped at the time of manufacturing into a particular angle or curve. Alternatively, the shape change can be a reversible and actuatable shape change such that the tip forms the shape upon activation by a user such that the tip can be used in a straight format until a shape change is desired by the user. The catheter advancement element 300 can also include a forming mandrel extending through the lumen of the elongate body 360 such that a physician at the time of use can mold the distal tip 346 into a desired shape. As such, the moldable distal tip 346 can be incorporated onto an elongate body 360 that has a guidewire lumen.

The elongate body 360 can extend along the entire length of the catheter 200, including the distal luminal portion 222 and the proximal control element 230 or the elongate body 360 can incorporate the proximal portion 366 that aligns generally side-by-side with the proximal control element 230 of the catheter 200. The proximal portion 366 of the elongate body 360 can be positioned co-axial with or eccentric to the elongate body 360. The proximal portion 366 of the elongate body 360 can have a lumen extending through it. Alternatively, the portion 366 can be a solid rod or ribbon having no lumen.

Again with respect to FIGS. 7A-7D, like the distal luminal portion 222 of the catheter 200, the elongate body 360 can have one or more radiopaque markers 344 along its length. The one or more markers 344 can vary in size, shape, and location. One or more markers 344 can be incorporated along one or more parts of the catheter advancement element 300, such as a tip-to-tip marker, a tip-to-taper marker, an RHV proximity marker, a Fluoro-saver marker, or other markers providing various information regarding the relative position of the catheter advancement element 300 and its components. In some implementations and as best shown in FIG. 7C, a distal end region can have a first radiopaque marker 344a and a second radiopaque marker 344b can be located to indicate the border between the tapering of the distal tip 346 and the more proximal region of the elongate body 360 having a uniform or maximum outer diameter. This provides a user with information regarding an optimal extension of the distal tip 346 relative to the distal end of the luminal portion 222 to minimize the lip at this distal end of the luminal portion 222 for advancement through tortuous anatomy. In other implementations, for example where the distal tip 346 is not necessarily tapered, but instead has a change in overall flexibility along its length, the second radiopaque marker 344b can be located to indicate the region where the relative flexibilities of the elongate body 360 (or the distal tip 346 of the elongate body 360) and the distal end of the luminal portion 222 are substantially the same. The marker material may be a platinum/iridium band, a tungsten, platinum, or tantalum-impregnated polymer, or other radiopaque marker that does not impact the flexibility of the distal tip 346 and elongate body 360. In some implementations, the radiopaque markers are extruded PEBAX loaded with tungsten for radiopacity. In some implementations, the proximal marker band can be about 2.0 mm wide and the distal marker band can be about 2.5 mm wide to provide discernable information about the distal tip 346.

The proximal control element 230 of the catheter 200 can include a proximal tab 234 on the proximal end of the proximal control element 230. Similarly, the proximal portion 366 coupled to the elongate body 360 can include a tab 364. The tabs 234, 364 can be configured to removably and adjustable connect to one another and/or connect to their corresponding proximal portions. The coupling allows the catheter advancement element 300 to reversibly couple with the catheter 200 to lock (and unlock) the relative extension of the distal luminal portion 222 and the elongate body 360. This allows the catheter 200 and the catheter advancement element 300 to be advanced as a single unit. In the locked configuration, the tab 364 or proximal portion 366 can be engaged with the catheter tab 234. In the unlocked configuration, the tab 364 may be disengaged from the catheter tab 234. The tab 364 or proximal portion 366 may attach, e.g., click or lock into, the catheter tab 234 in a fashion as to maintain the relationships of corresponding section of the elongate body 360 and the catheter 200 in the locked configuration. The tab 364 can be a feature on the proximal hub 375 such as the hub 375 shown in FIGS. 7F-7J.

Such locking may be achieved by, e.g., using a detent on the tab 364 that snaps into place within a recess formed in the catheter tab 234, or vice versa. For example, the tab 234 of the catheter 200 can form a ring having a central opening extending therethrough. The tab 364 of the body 360 can have an annular detent with a central post sized to insert through the central opening of the tab 234 such that such that the ring of the tab 234 is received within the annular detent of tab 364 forming a singular grasping element for a user to advance and/or withdraw the catheter system through the access sheath. The tabs 234, 364 may be affixed or may be slideable to accommodate different relative positions between the elongate body 360 and the luminal portion 222 of the catheter 200. In some implementations, a proximal end of the proximal control element 230 of the catheter 200 can include a coupling feature 334, such as clip, clamp, c-shaped element or other connector configured to receive the proximal portion 366 of the catheter advancement element 300 (see FIG. 2A). The coupling feature 334 can be configured to snap together with the proximal portion 366 through an interference fit such that a first level of force is needed in order to insert the proximal portion 366 into the clip of the tab 234 and a second, greater level of force is needed to remove the proximal portion 366 from the clip of the tab 234. However, upon inserting the proximal portion 366 into the coupling feature 334 the catheter advancement element 300 and the catheter 200 can still be slideably adjusted relative to one another along a longitudinal axis of the system. The amount of force needed to slideably adjust the relative position of the two components can be such that inadvertent adjustment is avoided and the relative position can be maintained during use, but can be adjusted upon conscious modification. The configuration of the coupling between the proximal portion 366 of the catheter advancement element 300 and the proximal control element 230 of the catheter 200 can vary. Generally, however, the coupling is configured to be reversible and adjustable while still providing adequate holding power between the two elements in a manner that is relatively user-friendly (e.g. allows for one-handed use) and organizes the proximal ends of the components (e.g. prevents the proximal control element 230 and proximal portion 366 from becoming twisted and entangled with one another). The coupling feature 334 configured to prevent entanglement and aid in the organization of the proximal portions can be integrated with the tabs or can be a separate feature located along their proximal end region.

The catheter advancement element 300 can be placed in a locked configuration with the catheter 200 configured for improved tracking through a tortuous and often diseased vasculature in acute ischemic stroke. Other configurations are considered herein. For example, the elongate body 360 can include one or more detents on an outer surface. The detents can be located near a proximal end region and/or a distal end region of the elongate body 360. The detents are configured to lock with correspondingly-shaped surface features on the inner surface of the luminal portion 222 through which the elongate body 360 extends. The catheter advancement element 300 and the catheter 200 can have incorporate more than a single point of locking connection between them. For example, a coupling feature 334, such as clip, clamp, c-shaped element or other connector configured to hold together the catheter advancement element 300 and proximal control element 230 or tab 234 of the catheter 200.

In some implementations, the proximal control element 230 of the catheter 200 can run alongside or within a specialized channel of the proximal portion 366. The channel can be located along a length of the proximal portion 366 and have a cross-sectional shape that matches a cross-sectional shape of the catheter proximal control element 230 such that the proximal control element 230 of the catheter 200 can be received within the channel and slide smoothly along the channel bi-directionally. Once the catheter 200 and elongate body 360 are fixed, the combined system, i.e., the catheter 200-catheter advancement element 300 may be delivered to a target site, for example through the working lumen of the guide sheath 400 described elsewhere herein.

The catheter advancement element 300 (whether incorporating the reinforcement layer or not) loaded within the lumen of the catheter 200 may be used to advance the catheter 200 to distal regions of the brain (e.g. level of the MCA). The traditional approach to the Circle of Willis is to use a triaxial system including a guidewire placed within a conventional microcatheter placed within an intermediate catheter. The entire coaxial system can extend through a base catheter or sheath. The sheath is typically positioned such that the distal tip of the sheath is placed in a high cervical carotid artery. The coaxial systems are often advanced in unison up to about the terminal carotid artery where the conventional coaxial systems must then be advanced in a step-wise fashion in separate throws. This is due to the two sequential 180 degree or greater turns (see FIGS. 1A-1C). The first 180 degree turn is at the level of the petrous to the cavernous internal carotid artery. The second 180 degree turn is at the terminal cavernous carotid artery as it passes through the bony elements and reaches the bifurcation into the anterior cerebral artery ACA and middle cerebral artery MCA. This S-shape region is referred to herein as the "siphon" or "carotid siphon". The ophthalmic artery arises from the cerebral ICA, which represents a common point of catheter hang-up in accessing the anterior circulation.

Conventional microcatheter systems can be advanced through to the anterior circulation over a guidewire. The inner diameter of the conventional microcatheter is significantly larger than the outer diameter of the guidewire over which it is advanced thereby forming a lip on a distal end region of the system that can catch on these side branches during passage through the siphon. Conventional microcatheter systems (i.e. guidewire, microcatheter, and intermediate catheter) are advanced through the bends of the carotid siphon sequentially to distal target sites rather than in a single, smooth pass. The bends of the carotid siphon are taken one at a time in a step-wise advancement technique. For example, to pass through the carotid siphon, the conventional microcatheter is held fixed while the guidewire is advanced alone a first distance (i.e. through the first turn of the siphon). Then, the guidewire is held fixed while the conventional microcatheter is advanced alone through the first turn over the guidewire. Then, the conventional microcatheter and guidewire are held fixed while the intermediate catheter is advanced alone through the first turn over the microcatheter and guidewire. The process repeats in order to pass through the second turn of the siphon, which generally is considered the more challenging turn into the cerebral vessel. The microcatheter and intermediate catheter are held fixed while the guidewire is advanced alone a second distance (i.e. through the second turn of the siphon). Then, the guidewire and interventional catheter are held fixed while the microcatheter is advanced alone through that second turn over the guidewire. Then, the guidewire and the microcatheter are held fixed while the interventional catheter is advanced alone through the second turn. This multi-stage, step-wise procedure is a time-consuming process that requires multiple people performing multiple hand changes on the components. For example, two hands to fix and push the components over each other forcing the user to stage the steps. The step-wise procedure is required because the stepped transitions between these components (e.g. the guidewire, microcatheter, and intermediate catheter) makes advancement too challenging.

In contrast, the catheter 200 and catheter advancement element 300 eliminate this multi-stage, step-wise component advancement procedure to access distal sites across the siphon. The catheter 200 and catheter advancement element 300 can be advanced as a single unit through the both turns of the carotid siphon CS. Both turns can be traversed in a single smooth pass or throw to a target in a cerebral vessel without the step-wise adjustment of their relative extensions and without relying on the conventional step-wise advancement technique with conventional microcatheters. The catheter 200 having the catheter advancement element 300 extending through it allows a user to advance them in unison in the same relative position from the first bend of the siphon through the second bend beyond the terminal cavernous carotid artery into the ACA and MCA. Importantly, the advancement of the two components can be performed in a single smooth movement through both bends without any change of hand position.

The catheter advancement element 300 can be in a juxtapositioned relative to the catheter 200 that provides an optimum relative extension between the two components for single smooth advancement. The catheter advancement element 300 can be positioned through the lumen of the catheter 200 such that its distal tip 346 extends beyond a distal end of the catheter 200. The distal tip 346 of the catheter advancement element 300 eliminates the stepped transition between the inner member and the outer catheter 200 thereby avoiding issues with catching on branching vessels within the region of the vasculature such that the catheter 200 may easily traverse the multiple angulated turns of the carotid siphon CS. The optimum relative extension, for example, can be the distal tip 346 of the elongate body 360 extending distal to a distal end of the catheter 200. A length of the distal tip 346 extending distal to the distal end of the catheter 200 during advancement can be between 0.5 cm and about 4 cm. This juxtaposition can be a locked engagement with a mechanical element or simply by a user holding the two components together.

The components can be advanced together with a guidewire, over a guidewire pre-positioned, or without any guidewire at all. In some implementations, the guidewire can be pre-assembled with the catheter advancement element 300 and catheter 200 such that the guidewire extends through a lumen of the catheter advancement element 300, which is loaded through a lumen of the catheter 200, all prior to insertion into the patient. The pre-assembled components can be simultaneously inserted into the sheath 400 and advanced together up through and past the turns of the carotid siphon.

Figure 11:
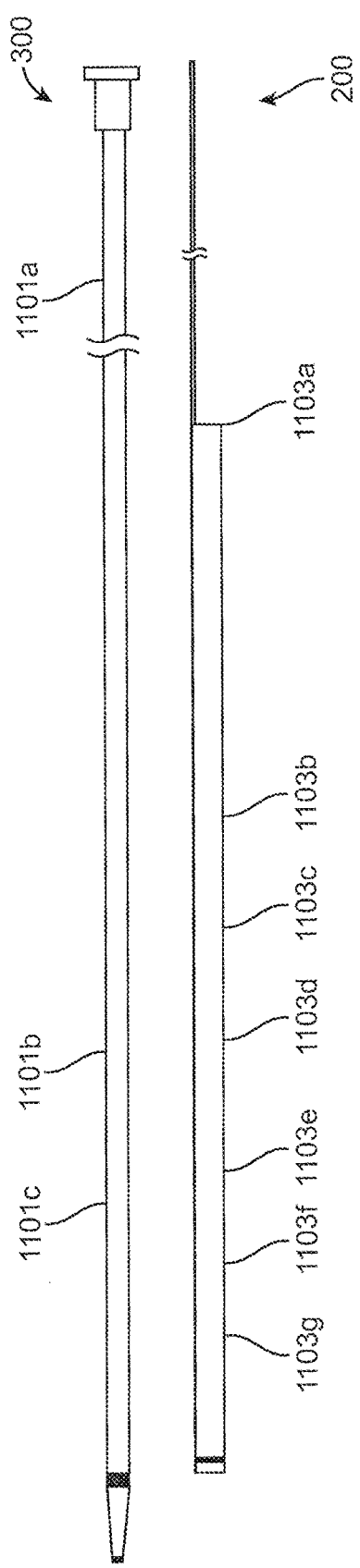
FIG. 11 is a schematic of an implementation of a catheter aligned with an implementation of a catheter advancement element illustrating staggered material transitions.

The optimum relative extension of the catheter 200 and catheter advancement element 300 can be based additionally on the staggering of material transitions. FIG. 11 is a schematic illustrating approximate locations of the material transitions in the catheter advancement element 300 and the approximate locations of the material transitions in the catheter 200. For example, the catheter advancement element 300 can include a proximal portion 366, which can be a hypotube, having a material hardness of approximately 72 D. The proximal portion 366 transitions at a location 1101a to a region having a material hardness of about 55 D that transitions at a location 1101b to a region having a material hardness of about 35 D that transitions at a location 1101c to a region have a material hardness of 35 D. Similarly, the catheter 200 can include a proximal control element 230 that is a stainless steel ribbon. The proximal control element 230 transitions at a location 1103a to a region having a material hardness of 72 D that transitions at a location 1103b to a region having a hardness of 55 D that transitions at a location 1103c to a region having a material hardness of about 40 D that transitions at a location 1103d to a region having a material hardness of about 35 D that transitions at a location 1103e to a region have a material hardness of 25 D that transitions at a location 1103f to a region having a material hardness of about 85 A that transitions at a location 1103g to a region having a material hardness of about 80 A. A distal-most region of the catheter advancement element 300 can be formed of Tecothane having a material hardness of about 62 A. The locations 1101 of the catheter advancement element 300 and the locations 1103 of the catheter 200 can be staggered such that the locations are off-set from one another. More or fewer material transitions may exist within the catheter advancement element and catheter.

The catheter 200 and catheter advancement element 300 can be pre-assembled at the time of manufacturing such that an optimum length of the catheter advancement element 300 extends distal to the distal end of catheter 200 and/or the material transitions are staggered. An optimum length of extension can be such that the entire length of the tapered distal tip of the catheter advancement element 300 extends outside the distal end of the catheter 200 such that the outer diameter of the catheter advancement element 300 where the at least one snug point is located aligns substantially with the distal end of the catheter 200. This can result in the snug outer diameter region of the elongate body 360 aligned substantially with the distal end of the catheter 200 such that it remains inside the lumen of the catheter 200 and only the tapered region of the distal tip 346 extends distal to the lumen of the catheter 200. This relative arrangement provide the best arrangement for advancement through tortuous vessels where a lip at the distal end of the system would pose the greatest difficulty. This optimal pre-assembled arrangement can be maintained by a coupler configured to engage with both the proximal control element 230 of the catheter 200 and the proximal portion 366 of the catheter advancement element 300. The coupler can be used during a procedure. Alternatively, the coupler can be removed prior to a procedure.

Figure 12:
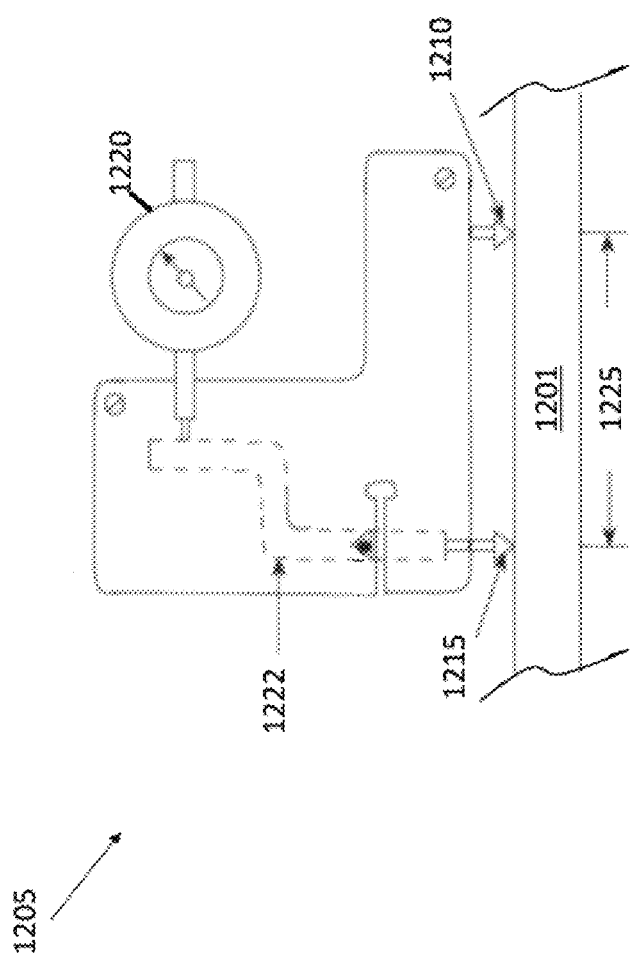
FIG. 12 is a schematic of an implementation of a bending force testing system.

Different regions of the distal luminal portion 222 and the elongate body 360 of the catheter advancement element 300 can have different bending stiffness. Bending stiffness in N-mm$^2$ can be measured by assessing the force in Newtons (N) generated upon deflecting the device a certain distance using a particular gauge length. FIG. 12 is a schematic of a testing system 1205 for assessing bending stiffness or bending force of the various components described herein. The testing system 1205 can vary as is known in the art. The testing system shown in FIG. 12 includes a pin 1210 forming a fixed point, an anvil 1215 connected by a lever 1222 to a strain gauge 1220 forming a gauge point. The pin 1210 can hold the specimen 1201 to be tested such that a gauge length 1225 of the specimen 1201 is exposed. The anvil 1215 is attached to the strain gauge 1220 via the lever 1222 and can be urged against a portion of the specimen 1201 that is positioned away from the pin 1210 by the gauge length 1225. The anvil 1215 can displace this portion such that the portion triggers a force measurable by the strain gauge 1220. The gauge length 1225 can be about 5 mm. The anvil 1215 can have a width, for example, about 2 mm, resulting in a minimum gauge length of about 3 mm. The length can vary depending on the testing system.

The bending stiffness (Elastic modulus×area moment of inertia) can be calculated according to the equation $EI=FL^3/3\delta$, where F is deflection force, L is gauge length, and $\delta$ is deflection. For example, using a 3 mm gauge length (L=3 mm) and deflecting a tip of the catheter 2 mm ($\delta$=2 mm), 0.05-0.5 N of force can be generated. In some implementations, the distal-most end of the distal luminal portion can range in bending stiffness between 0.225-2.25 N-mm$^2$. As a comparison, the flexibility of the catheter advancement element 300 based on similar deflection measurements and calculations can be as follows. Upon 2 mm deflection and force gauge length of 3 mm, the distal tip of the catheter advancement element 300 can range in bending force between 0.005-0.05 N or can range in bending stiffness between 0.0225-0.225 N-mm². Other procedural catheters described herein can have a similar flexibility ranges providing a variable relative stiffness that transitions from the proximal end towards the distal end of the catheter as will be described elsewhere herein.

Figure 13A:
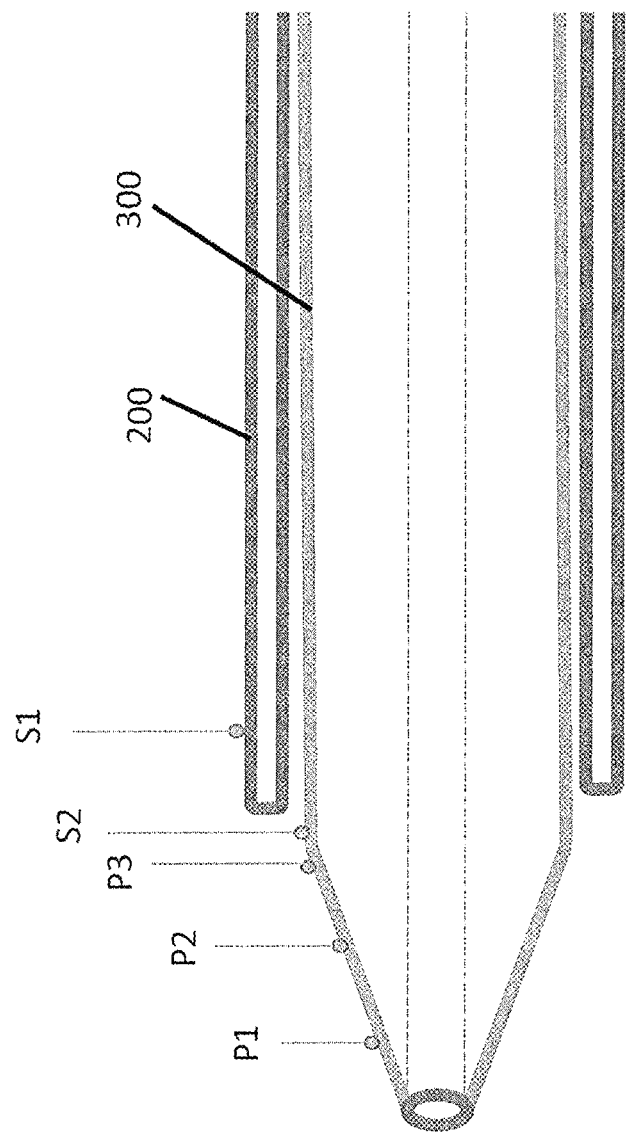
FIG. 13A is a schematic of a distal end region of a catheter advancement element extending through a catheter and points tested for bending force.
Figure 13B:
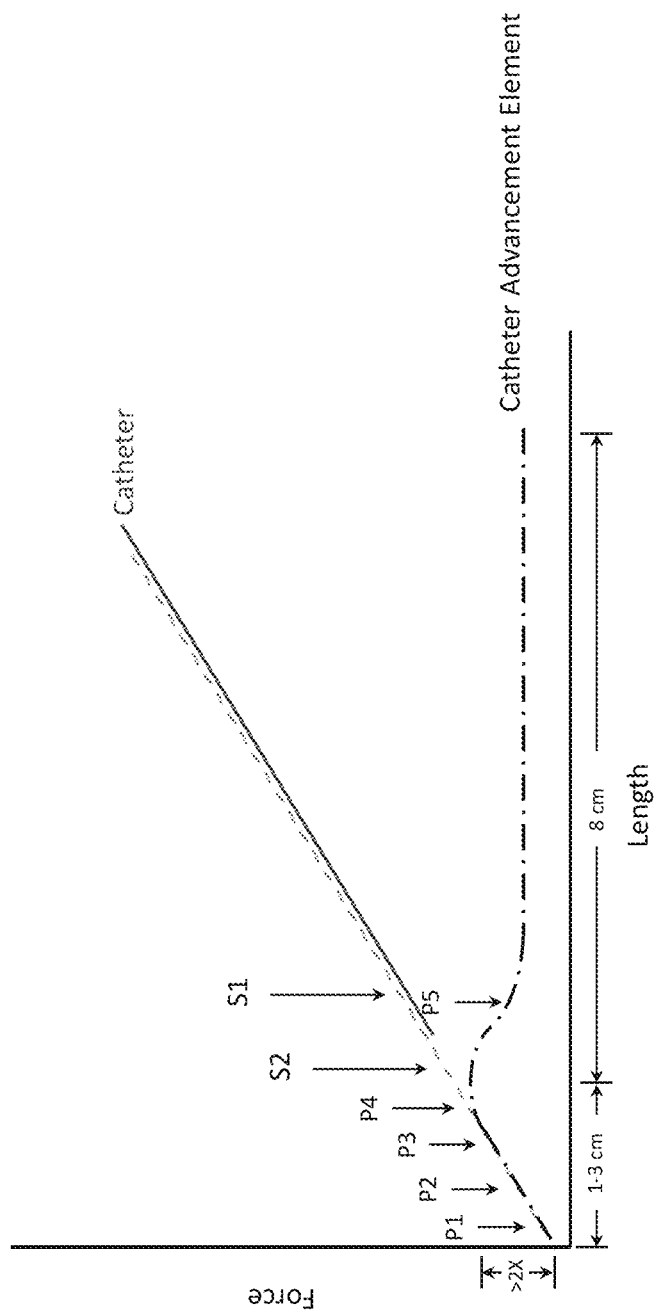
FIG. 13B illustrates bending force in Newtons (N) along a length of a catheter system including a catheter and a catheter advancement element in the advancement configuration (hashed line), the catheter advancement element alone (hash-dot-hash line), and the catheter alone (solid line)

FIGS. 13A-13B illustrate, in schematic, points along the catheter system that can be tested using the testing system shown in FIG. 12. The points may vary depending on the overall size of the catheter system. The various points of catheter system 150 can be tested when the catheter system 150 is placed in an advancement configuration. The catheter 200 can have a lumen and a distal end having an opening from the lumen 223. The lumen can have an inner diameter at the distal end that is at least about 0.052". The tubular portion 360 of the catheter advancement element 300 can have an outer diameter having at least one snug point, where a difference between the inner diameter and the outer diameter at the snug point can be no more than about 0.010". The at least one snug point can be the point on the catheter advancement element 300 located just proximal to the tapered distal tip 346. When the catheter advancement element 300 is in the advancement configuration and is positioned coaxially within the lumen of the distal luminal portion 222 of the catheter 200, the at least one snug point of the tubular portion 360 can substantially align with the distal end of the catheter 200. When in this configuration, the distal tip portion 346 of the catheter advancement element 300 extends distal to the distal end of the catheter 200. In some implementations, the difference at the snug point is nor more than about 0.010" or between about 0.006" and 0.008".

The tubular portion 360 of the catheter advancement element 300 can have a radiopaque marker band embedded within or positioned over a wall of the tubular portion 360 near the distal end region. A first radiopaque marker band 344a can be found at the distal end of the tapered tip portion 346 and a second radiopaque marker band 344b can be found at the proximal end of the tapered tip portion 346. The proximal radiopaque marker band 344b can have a proximal edge, a distal edge, and a width between the proximal and distal edges. When in the advancement configuration, the proximal edge of the radiopaque marker band 344b can align substantially with the distal end of the distal, catheter portion 222 such that the radiopaque marker band 344b remains external to the lumen 223 of the distal, catheter portion 222. At least a portion of the radiopaque marker band 344b can be positioned at the snug point, or the point of the catheter advancement element 300 where the outer diameter is no more than about 0.010", preferably between about 0.006" and 0.008" smaller than the inner diameter of the catheter 200 it is positioned within. The at least one snug point of the tubular portion 360 can be located proximal to the tip portion 346 and can be where the taper of the tip portion 346 substantially ends. This allows for full extension of the tapered tip portion 346 outside the distal end of the catheter 200 and the snug point aligned substantially within the distal opening from the lumen 223 of the distal, catheter portion 222 thereby minimizing any distal-facing lip that might be created by the catheter 200. The snug point can be located along at least a portion of a length of the outer diameter of the tubular portion 360 that has a length of at least about 5 cm up to about 10 cm, the outer diameter being substantially uniform or non-uniform.

The tip portion 346 can include at least three points (see, e.g., P1, P2, P3 of FIGS. 13A-13B) spaced along the length of the tip portion. The distal point P1 of the at least three points can be located a distance proximal from the distal-most end of the catheter advancement element 300. The distance can be a minimum distance needed to create a gauge length for the testing system, for example at least about 3 mm to about 5 mm. An intermediate point P2 of the at least three points can be located a distance proximal to the distal point P1. A proximal point P3 of the at least points can be located a distance proximal to the intermediate point P2. Additional points can be measured on the tapered tip portion 346 and that these are provided as illustrative.

FIG. 13A also illustrates points that can be tested on the system 150 as a whole. The coaxial catheter system 150 in the advancement configuration can include at least two system points along a length of the coaxial system 150. A first system point S1 of the at least two system points can be located proximal to the distal end of the catheter 200. The first system point S1 generally takes into account the combined bending force of the catheter 200 and the bending force of the catheter advancement element 300 extending through the catheter 200 (see hashed line in FIG. 13B). The first system point S1 can be located proximal to the distal end of the catheter 200 by a gauge length of about 5 mm. A second system point S2 of the at least two system points can be located distal to the first system point S1, for example, by a distance that is at least about 1 mm distal to the distal end of the catheter portion. The second system point S2 can take into account the bending force of the catheter advancement element 300 extending outside the catheter 200. The second system point S2 is illustrated in FIG. 13A as being a different point from P3, but the second system point S2 can be the same as the proximal portion P3 or the same as another point such as P4. The points are provided for illustrative purposes and are not intended to be limiting. Other points are considered herein.

FIG. 13B illustrates theoretical bending forces (N) of a catheter system 150 at various points along a length of the system 150. The at least three points on the tip portion 346 include P1, P2, P3, and also P4 spaced along the length of the tip portion 346 of the catheter advancement element 300 (represented by a hash-dot-hash line). Each of these points can be located distal to the distal end of the catheter 200 (solid line) when in the advancement configuration and, as such, take into account the bending force of only the catheter advancement element 300. A fifth point P5 along the length of the catheter advancement element 300 is also shown in FIG. 13B and can be at a location positioned inside the catheter 200 when the system 150 is in the advancement configuration. P5, however, takes into account the bending force measurement of only the catheter advancement element 300.

The catheter 200 and catheter advancement element 300 can each have any of a variety of material transitions from distal end towards the proximal end such that when the catheter advancement element 300 is positioned coaxially within the catheter 200 in the advancement configuration, the flexibility of the system 150 transitions linearly from the flexibility of the distal tip of the catheter advancement element 300 towards more proximal regions of the system 150. In other words, the transition in flexibility from distal tip 346 of the catheter advancement element 300 (positioned external to the distal end of the catheter 200 when in the advancement configuration) to the flexibility of the system 150 as a whole (i.e. catheter advancement element 300 plus the catheter 200) can be defined by a slope that includes no significant step increase and is substantially constant. FIG. 13B illustrates this additive stiffness of the system 150 moving proximally along a length of the system 150. FIG. 13B shows the distal end of the catheter advancement element 300 at P1 has a bending force that is significantly lower than the bending force of the distal end of the catheter 200 through which it extends (e.g. greater than at least about 2×). In some implementations, the bending force of the distal end of the catheter advancement element 300 at P1 is no more than about 0.05 N. The bending force of the catheter advancement element 300 can increase over the length of the distal tip portion 346 to approach the higher bending force of the distal end of the catheter 200. For example, the distal tip portion 346 can increase in stiffness over its length by at least 2× to approach the higher bending force of the distal end of the catheter 200. The bending force of the catheter system 150 over its length can have a generally constant slope. This generally constant slope of increasing bending force for the distal tip portion of the catheter advancement element 300 (shown as a hash-dot-hash line in FIG. 13B) can transition to a generally constant slope of increasing bending force for the combined system 150 (shown as a hashed line in FIG. 13B) such that there is no significant step-up or change in slope between the two. The bending force of the distal tip portion 346 can have a constant slope up to where it transitions to the constant slope of the system 150 as a whole (i.e. additive bending force between catheter 200 and catheter advancement element 300 shown by hashed line). The bending force of the catheter advancement element 300 can continue to increase along a length of the tip portion 346 (e.g. from P1 to P2 to P3 to P4) and then decrease again, for example, proximal to the at least one snug point (e.g. see P5 of FIG. 13B). The bending force of the catheter advancement element 300 can decrease proximal to this snug point and remain significantly lower than the bending force of the catheter 200 over a length. In some implementations, a proximal marker band 344b identifying the proximal end of the tapered distal tip 346 of the catheter advancement element 300 can locally increase stiffness of the catheter advancement element 300 at this point (e.g. near P3, P4, S2 of FIG. 13B) thereby minimizing the step-up in stiffness from the distal tip portion 346 of the catheter advancement element 300 to the distal end of the catheter 200 of the assembled system 150. Tables 1, 3, 4, and 5 of Example 1 in the Experimental section below describes the bending forces of the various points along a length of different catheter systems.

The bending forces along the length of the catheter system 150 can be used to calculate slopes of various segments of the system 150. A difference between the bending force of P2 and the bending force of P1 divided by the distance between P2 and P1 and/or a difference between the bending force of P3 and the bending force of P2 divided by the distance between P3 and P2 can provide a first flexibility slope. A difference between the bending force of P3 and the bending force of P2 divided by the distance between P3 and P2 can provide a second flexibility slope. An average of the first flexibility slope and the second flexibility slope can define an average tip portion flexibility slope. In some implementations, a fourth distal tip point can be measured such that the average tip portion flexibility slope can take into account this additional segment in calculating the average slope (e.g. segment between P3 and P4). A difference between the bending force of S1 and the bending force of S2 (whether P3 or P4) divided by the distance between S1 and S2 (whether P3 or P4) can provide a first system flexibility slope.

In some implementations, the bending force of the distal end of the catheter advancement element 300 can be no more than about 0.05 N. The average tip portion flexibility slope can be at least about 0.005 N/mm. The system flexibility slope can be between about 0.01 N/mm to about 0.03 N/mm.

A ratio between the system flexibility slope to the average tip portion flexibility slope can be less than about 25, less than about 15, and preferably less than about 5, such as about 3 down to about 1. The slopes can be substantially constant or close to constant and substantially devoid of step-increases in bending force slope from one segment to the next along the length of the catheter system 150. In particular, the catheter systems described herein avoid large step-increases in slope from the flexibility of the portion extending distal to the distal end of the catheter and the flexibility of the system as a whole (see also FIGS. 14A-14D described below in Example 1).

The bending force of the distal tip of the catheter advancement element 300 at P1 can be a fraction of the bending forces of the distal end of the catheter 200, such as between about 5%-15%. In contrast, the bending force of the snug point on the catheter advancement element 300 near the proximal end of the distal tip 346 (e.g., P3 or P4 or S2) can be about 50%-90% the bending force (or flexibility) of the distal end of the catheter 200. Thus, the bending force at the snug point of the catheter advancement element 300 can be closer to the bending force of the distal end of the catheter 200. In some implementations, a portion of the catheter advancement element 300 that is proximal to the tapered distal tip 346 can have a length of about 5 cm to about 10 cm and this portion can have a bending force (or flexibility) that can be about 40%-90% the bending force of the distal end of the catheter 200.

The smooth transition in flexibility over the length of the catheter systems described herein provide optimum navigability without risk of kinking. The catheter systems described herein can have a distal end that is exceptionally flexible and transition towards a proximal end that is exceptionally stiff for optimum torqueing and manipulation. Thus, the bending force of P1 of the catheter advancement element 300 can be a fraction of a bending force of a portion of the proximal portion 366 of the catheter advancement element 300. The proximal portion 366 can include at least one stiffness point that is within about 20 cm proximal to the tubular portion 360. The stiffness point can have a bending force that is relatively high, for example, between about 5 N up to about 15 N. A ratio of the bending force of the at least one stiffness point to the first bending force of P1 can be at least about 100, at least about 200, or at least about 300. The proximal portion 366 of the catheter advancement element 300 can be more than 300 times stiffer than the distal tip P1 of the catheter advancement element at P1. The bending force of the catheter advancement element 300 at the distal tip P1 can be no more than about 0.30% of the bending force of the proximal portion 366, for example between 0.10% to about 0.50%.

Methods of Use

Figure 15:
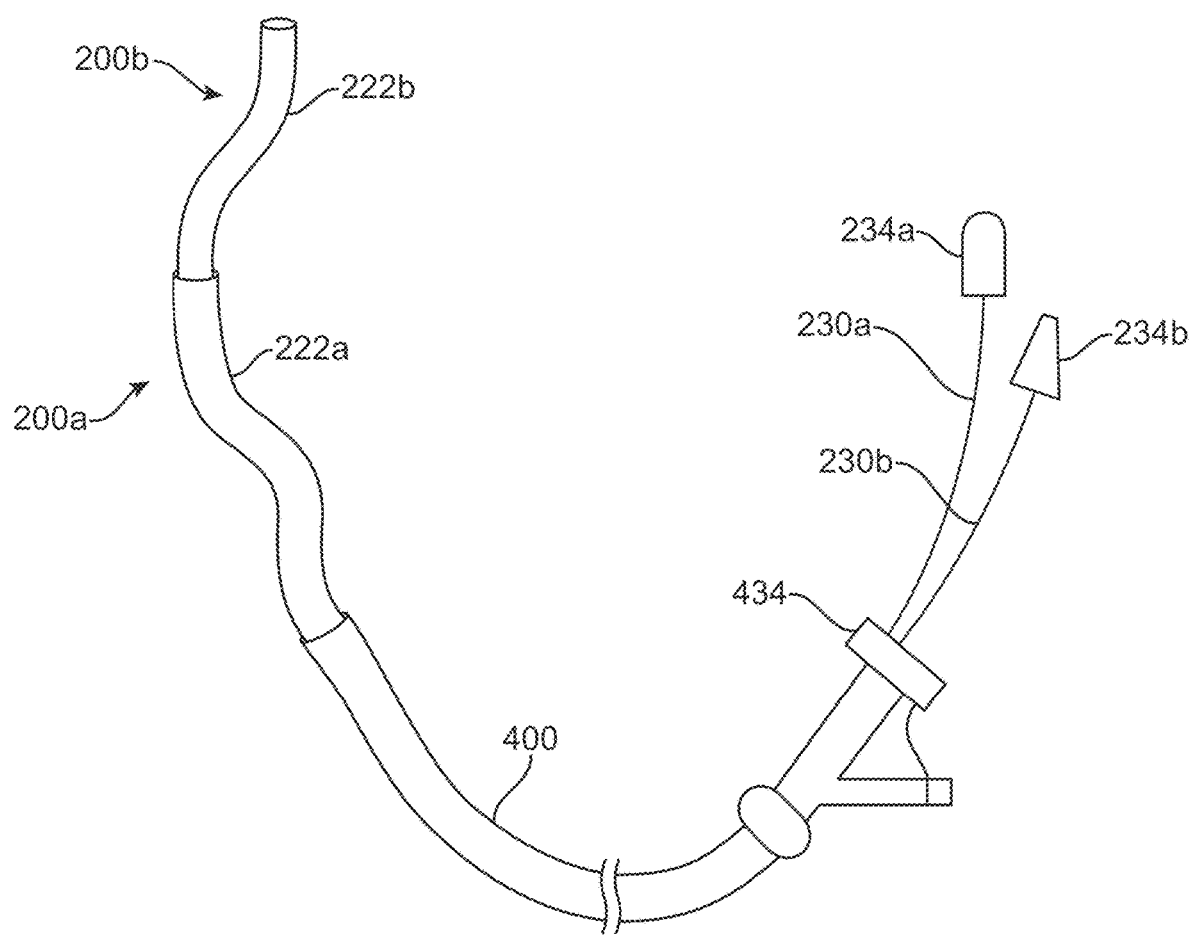
FIG. 15 illustrates an implementation of a nested catheter system.

In an implementation shown in FIG. 15, a guide sheath 400 can be deployed such that the distal end of the sheath 400 is advanced to a location in, for example, the internal carotid artery (ICA). The sheath 400 can be advanced to the carotid artery over a guidewire and using an advancement tool. The guidewire and advancement tool, if used, can be removed or exchanged for a smaller guidewire that can be advanced further distal into the cerebral vessels or no guidewire at all as described in more detail below. A first catheter 200a can be advanced through the working lumen of the guide sheath 400 and out the distal end. The first catheter 200a can have a distal luminal portion 222a coupled to a proximal control element 230a. The proximal control element 230a can have a smaller outer diameter compared to the outer diameter of the distal luminal portion 222a and can be coupled near a proximal opening from the lumen of the distal luminal portion 222a. The first catheter 200a can be advanced using a catheter advancement element and without the help of a guidewire. The catheter advancement element can aid the advancement of the first catheter 200a through the vessel without hanging up on a severe angulation and/or a branching vessel. The first catheter 200a can be advanced through the working lumen of the guide sheath 400 and then through the vessel to a first target location. The catheter advancement element 300 can be removed from the lumen of the first catheter 200a. A second catheter 200b having a second catheter advancement element 300 can be advanced through the lumen of the first catheter 200a. The second catheter 200b can also include a distal luminal portion 222b coupled to a proximal control element 230b near a proximal opening from the lumen of the distal luminal portion 222b. Similar to the first catheter 200a, the proximal control element 230b of the second catheter 200b can have a smaller outer diameter compared to the outer diameter of the distal luminal portion 222b. The distal end of the second catheter 200b can be extended using its proximal control element 230b to extend past the distal end of the first catheter 200a such that the smaller diameter second catheter 200b can reach a target site located to a distal vessel having a narrower dimension than the location of the first catheter 200a. In this implementation, the first spined catheter 200a can act as a support catheter for the second spined catheter 200b. The second catheter 200b can be advanced with or without a guidewire in place. Upon removal of the second catheter advancement element 300, the inner lumen of the second spined catheter 200b can fluidly communicate with the inner lumen of the first spined catheter 200a that fluidly communicates with the working lumen of the guide sheath 400 forming a contiguous lumen formed of three sections of increasingly larger dimensions towards the proximal end of the catheter system. For example, the first catheter 200a can have a distal luminal portion 222a having an inner diameter of about 0.088" and the second catheter 200b can have a distal luminal portion 222b having an inner diameter of about 0.070". More than two nested spined catheters is considered and that their respective inner and outer diameters are sized to receive one another for use together. The corresponding ID and OD of the catheters can be sized such that they slide relative to one another, but still provide sufficient sealing. For example, the contiguous lumens created by the nested arrangement can seal against one another such that aspiration can be drawn through them and an appropriate pressure can be applied through the nested catheters to accomplish, for example, aspiration force sufficient for aspiration embolectomy of distant clots.

The proximal end of the nested catheter system can incorporate various gripping, organizing, and attachment features. For example, the guide sheath 400 can include a proximal end coupled to a rotating hemostatic valve 434 that provides access to the working lumen through which the catheters can be inserted. Each of the components of the catheter system can extend proximally out from the valve 434. For example, the proximal control elements 230a, 230b of the catheters 200a, 200b can extend through the valve 434. Proximal extensions of their respective catheter advancement elements (not shown in FIG. 15) can also extend proximally through the valve 434. Each of these components in the nesting or telescoping catheter set can incorporate identifying features at their proximal end regions that distinguish them from one another. For example, each proximal control element 230a, 230b can include a tab 234a, 234b having a distinguishing shape, color, or other visual characteristic that is unique to that particular catheter. Each proximal control element 230a, 230b can include a coupling feature, such as a clip or other connector, that organizes the various control elements and prevents entanglement. Nesting catheters and their respective catheter advancement elements can be incorporated within a kit.

The systems described herein contemplate using a base sheath and a catheter that can pass through the sheath and having sufficient length to reach the intracerebral target, such as the M1 segment of the middle cerebral artery. The use of a delivery catheter or catheter advancement element with a tapered tip allow for large bore catheter delivery of full-length "over-the-wire" catheters or catheters such as those described herein having a proximal extension. The catheter advancement element can include a pair of radiopaque markers configured to aid the operator in delivery of the system. The distal marker near the distal-most end of the catheter advancement element can be differentiated from the distal marker on the catheter by its characteristic appearance under fluoroscopy as well as by simply jogging back and forth the atraumatic catheter advancement element to understand the relationship and positioning of the catheter advancement element relative to the catheter. The second marker on the catheter advancement element that is proximal to the distal-most tip marker can delineate the taper of the distal tip, i.e. where the outer diameter of the catheter advancement element has a sufficient size to reduce the "lip" of the transition between the catheter advancement element and the catheter through which it is inserted and configured to deliver. The markers aid in positioning the catheter advancement element relative to the distal end of the large-bore catheter such that the tip of the catheter is aligned with the taper of the catheter advancement element and the best alignment is facilitated.

The relationship between the distal tip marker of the large-bore catheter is at or ideally just proximal to the taper marker of the catheter advancement element (i.e. the proximal marker identifying the start of the taper) is identifiable with the tandem marker system. The paired elements are in a "tip-to-taper" position. The relative extension between the catheter advancement element and the catheter can be adjusted at the insertion of the system into the RHV. However, the relative extension can become altered with advancement through the sheath or guide catheter. As the system exits the guide catheter, the large bore catheter and the catheter advancement element can be adjusted to that the tip-to-taper position is assumed as the system traverses the often tortuous proximal vessel (e.g. the cervical internal carotid artery) towards more distal targets. The system of the large bore catheter and the catheter advancement element can be locked into their relative extension so that the juxtaposition of the catheter advancement element and the large-bore catheter is maintained. As the large-bore catheter is visualized within the sheath distal end or even slightly beyond the distal end of the sheath, the catheter advancement element can be adjusted to assume the proper position relative to the catheter before advancement resumes. The optimum relative extension between the distal marker of the catheter to the taper marker on the catheter advancement element can be maintained through as much of the anatomy as possible to maximize the delivery capability of the catheter advancement element to navigate both tortuosity and to avoid side branches such as the ophthalmic artery. Once the target is reached, the catheter advancement element is then held fixed and the large-bore catheter then advanced over the catheter advancement element towards the target without crossing the target.

The catheter advancement element is designed specifically such that the catheter can be delivered without a need for a guidewire. This ability to deliver without crossing the embolus and without a guidewire is based upon the smooth transitions between the outer diameter of the catheter advancement element and the large-bore catheter as well as the smooth transition in flexibility between the two. When the catheter advancement element is bent into an arc of greater than 180 degrees, the softness and flexibility creates a smooth arc without severe bends or kinks in the geometry of the catheter. Thus, the catheter advancement element seeks the larger lumens and goes where the majority of blood flow goes as opposed to into the smaller branch arteries. The distal tip of the catheter advancement element can facilitates a strong preference to seek out the larger vessels during advancement into the distal vessels. This propensity to stay within the main channel allows for the advancement of large bore catheters without the aid of a guidewire. The propensity to follow the main channels of blood flow aligns with acute ischemic stroke pathophysiology where major emboli tend to follow these same routes to a point where the embolus lodges and interrupts antegrade blood flow. As well, these major channels are often ideal for placement of access catheters as these conduit arteries allow for smaller catheters to pass into specific target arteries for therapeutic intervention.

Standard neurovascular intervention, and nearly all endovascular intervention, is predicated on the concept that a guidewire leads a catheter to a target location. The guidewires are typically pre-shaped and often find side-branches of off-target locations where the guidewire will bunch or prolapse causing time-consuming nuisances during interventions that often require repeated redirection of the guidewire by the operator to overcome. In addition, this propensity of a guidewire to enter side-branches can be dangerous. Guidewires are typically 0.014" to 0.018" in the neuroanatomy and will find and often traumatize small branches that accommodate this size, which can lead to small bleeds or dissections and occlusion. In a sensitive area like the brain these events can be catastrophic. The tendency of a guidewire to bunch and prolapse can also cause a leading edge to the guidewire that can be advanced on its own or as part of a triaxial system to create dissection planes and traumatize small vessels.

In contrast, the catheter advancement element described herein preferentially stays in the larger lumen of a conduit vessel. In the setting of stroke treatment an embolus is driven to certain anatomies because of the blood flow that the arterial system draws in the cerebral anatomy. The catheter advancement element tends to traverse a path identical to the path an embolus will take, particularly an embolus driven from a location such as cardiac or carotid etiology. The catheter advancement element delivers to the largest lumen within the anatomy even in light of the highly tortuous anatomy and curves being navigated. The catheter advancement element can preferentially take the larger lumen at a bifurcation while also following the current of the greatest blood flow thereby maintaining the general direction and angulations of the parent vessel.

In viewing the standard anatomy found in the cerebral vasculature, the Circle of Willis is fed by two vertebral and two carotid conduit arteries. As these four arteries are the access points to the cerebral anatomy—the course of the catheter advancement element can be identified and has been validated in standard cerebral anatomy models. In the anterior circulation where the conduit artery point of entry for cerebral endovascular procedures is the internal carotid artery (ICA), the catheter advancement element can guide the large-bore catheter to the M1 segment of the middle cerebral artery (MCA). The very flexible nature of the catheter advancement element combined with the distal flexible nature of most cerebral catheters combine to allow delivery through severe tortuosity. Independent of the tortuous nature of the course of the arteries, the catheter advancement element tends to navigate the turns and deliver to the largest offspring from a parent artery, for example, ICA to M1 segment of the MCA. The M2 level branching of the M1 can be variable, but is often seen to have two major M2 branches (superior and inferior) and, depending on the anatomy, which can vary significantly between patients, may be seen to bifurcate "equally" or "unequally." If the caliber of the M2 branching is of similar size and angulation, the catheter advancement element may take one of the two branches. If the target for catheter placement is not in a favorable angulation or size of artery, the catheter advancement element may need to be curved (e.g. via shaping of a malleable distal tip) and directed or a guidewire may be used.

In some anatomies where the M2 bifurcation is "even" in size, a back-and-forth motion may aid in selecting one branch then the other while still avoid the need or use of a guidewire or a curved distal tip of the catheter advancement element. The back-and-forth motion can allow for the catheter advancement element to be directed into either branch of the M2. The catheter advancement element, even when initially straight, achieves some curvature that aids in directing it into a branch vessel. Thus, when an operator encounters an M2 bifurcation and there is a desire to cannulate either branch of an evenly divided bifurcation, selection of either branch is possible using the catheter advancement element without a guidewire.

Thus, main channels such as the ICA, the middle cerebral artery and its tributaries in the anterior circulation will naturally be the pathway of preference for the described catheter advancement element and subsequence large-bore catheter delivery (via access from the ICA). A similar phenomenon can occur in the posterior circulation, which is accessed via the vertebral arteries arising from the subclavian arteries on the right and the left. The catheter advancement element will take the main channels in this circulation as well by traversing the vertebral arteries to the basilar artery and to the major tributaries of the basilar: the posterior cerebral artery and superior cerebellar arteries in the posterior circulation.

Navigation using the catheter advancement element can provide maximal deliverability with minimal vascular trauma. Catheters can cause "razoring" effects in a curved vessel because the blunt end of a large bore catheter can tend to take the greater curve in rounding a vessel when pushed by the operator. This blunt end can gouge or "razor" the greater curve with its sharp edge increasing the risk for dissection along an anatomic plane within the multilayered mid- or large-sized artery or vein (see, e.g. *Catheter Cardiovasc. Interv.* 2014 February; 83(2):211-20). Placement of a partially-inflated balloon and guidewire through the catheter in this setting can mitigate this "razor" effect by taking the edge off the large-bore catheter. Similarly, the catheter advancement element can serve to minimize the edge of these catheters. Positioning the catheter advancement element within the lumen of the large-bore catheter such that the taper marker of the catheter advancement element is aligned optimally with the distal tip marker of the catheter minimizes the edge and thereby eliminates "razoring" as the large-bore catheter is advanced through turns of the vessel. This is particularly useful for the cerebral anatomy. Stroke treatments are typically needed in regions distal to the carotid siphon, particularly distal to the ophthalmic artery takeoff from the greater curve of the severe tortuosity of the final turn of the carotid siphon "5-turn", the "anterior genu" of the carotid siphon typically seen as part of the terminal internal carotid artery (ICA). The specifics of the catheter advancement element in proper alignment within the large bore catheter (the "tip-to-taper" position noted by the distal tip marker) relative to the taper marker of the catheter advancement element maximize the likelihood that razoring and hang-up on the ophthalmic artery are avoided. The taper marker of the catheter advancement element can be positioned at or past the take-off of the ophthalmic artery to minimize these deleterious effects and allows the large-bore catheter to pass the ophthalmic artery without incident. In a relatively straight segment, which is common after passing the siphon, the large-bore catheter can be advanced over the catheter advancement element, which serves still as a guiding element to the target. The transition between the catheter advancement element and the distal edge of the large-bore catheter is insignificant, especially compared to the step changes present with a typical microcatheter or guidewire, which do not prevent hand-ups on branches such as the ophthalmic artery. The catheter advancement element allows for maneuvering of the large-bore catheter clear to the face of the embolus without use of a microcatheter or guidewire and without crossing and/or fragmenting the embolus in any way.

Conventional techniques to treat AIS whether with a stent retriever, aspiration techniques, or a combination of the two, require crossing the target occlusion with a guidewire and a microcatheter. Crossing of the embolus with a guidewire and then microcatheter can create fragmentation of the occlusion, which can be friable and thrombotic in nature. Thus, an aspiration technique where the embolus is removed en toto without any crossing of the occlusion with any device is advantageous.

A stent retriever cannot cross or engage the target occlusion without the "unsleeving" of the stent retriever across the embolus. ADAPT is a frontline aspiration-only technique that avoids crossing the target occlusion with a stent retriever thereby lessening the risk of fragmentation. However, the ADAPT approach still requires crossing the target occlusion with both a guidewire and microcatheter (see Turk et al. *J. Neurointerv. Surg.* 2014 Apr. 1; 6(3):231-7). A guide catheter such as Neuron Max (Penumbra) is positioned as distally as possible. A microcatheter and a micro guidewire are advanced through the guide catheter and distal to the occlusion. Using the microcatheter and micro guidewire as support, a reperfusion catheter such as Penumbra 5 Max is advanced to the occlusion. Aspiration is applied until the occlusion corks or wedges within the tip of the reperfusion catheter. The reperfusion catheter is withdrawn and removed while maintaining aspiration and the occlusion within the catheter tip.

The systems described herein need not incorporate a guidewire or microcatheter. And, if a guidewire and microcatheter are used, they need not be advanced to cross the target occlusion. Thus, the systems described herein can incorporate relatively large bore catheters that are delivered without disturbing the target occlusion, reducing the risk for stroke and downstream effects from fragmentation of the occlusion, and having improved efficiency. Additionally, the systems described herein are single-operator systems allowing the operator to work at a single RHV and, in the case of spined components, can manipulate all the elements being used to navigate the anatomy with single-handed "pinches." This is sometimes referred to as "monopoint."

As described above, the catheter advancement element can be arranged coaxially within the single lumen of the distal catheter portion forming a coaxial catheter system. The catheter can have a distal, catheter portion and a proximal extension. The distal, catheter portion can have an inner diameter defining the single lumen and a distal end defining a distal opening from the lumen. The proximal extension can be coupled to and extend proximally from the distal, catheter portion. The catheter advancement element can have a tubular, polymeric portion having an inner diameter defining a lumen, a first outer diameter that is substantially uniform along a length, and a radiopaque marker band embedded within or positioned over a wall of the tubular, polymeric portion. The radiopaque marker band can create a second outer diameter that is located distal to and that is larger than the first outer diameter. A tapered, polymeric tip can be located distal to the second outer diameter that terminate at a distal opening from the lumen of the tubular portion. The tapered, polymeric tip can have a length that is between about 0.5 cm up to about 4 cm, for example, between about 1 cm and about 3 cm, or about 2.5 cm. The catheter advancement element can also include a proximal extension coupled to and extending proximally from the tubular, polymeric portion.

The coaxial catheter system can have an advancement configuration where the tapered, polymeric tip of the catheter advancement element extends distal to the distal end of the distal, catheter portion and the radiopaque marker band is substantially aligned with the distal end of the distal, catheter portion, and the first outer diameter is positioned within the lumen of the distal, catheter portion.

The operator can work from a single RHV of the guide sheath to manipulate both the catheter and the catheter advancement element. The coaxial catheter system can be advanced together, maintaining the advancement configuration. The relative relationship between the radiopaque marker band on the catheter advancement element and a second marker band near the distal end of the catheter can aid in maintaining the advancement configuration during delivery. The operator can hold the two in relative position to one another using a single pinch and advance this coaxial catheter system.

The coaxial catheter system can be advanced as far distal as possible until the catheter advancement element is positioned at the face of the embolus. The proximal extension of the catheter advancement element can be held "fixed" at the RHV and the catheter advanced over the catheter advancement element so that the distal end of the distal, catheter portion is advanced over the catheter advancement element to the face of the embolus. No guidewire or microcatheter is needed to advance the coaxial catheter system to the face of the embolus. Importantly, no devices need cross the embolus.

The catheter advancement element can then be withdrawn from the coaxial catheter system and removed from the single RHV while the catheter is held in position at the face of the embolus. The system is ready for initiation of aspiration as will be described in more detail below.

In some implementations, the first coaxial catheter system may not be able to reach the face of the embolus. Thus, the catheter advancement element of the coaxial catheter system can be removed leaving the lumen of the distal, catheter portion open for advancing a second coaxial catheter system through the first catheter. The second coaxial catheter system can include a second catheter and a second catheter advancement element and be advanced similarly as the first coaxial catheter system (i.e. via monopoint manipulations), but through the first catheter acting as a support catheter.

Once the catheter is in position at the face of the embolus, the RHV can be sealed and aspiration initiated through the same RHV such as via a side-arm. The embolus can be aspirated from the body through the catheter via the aspiration pressure alone. Alternatively, the catheter having the embolus corked at the distal opening of the catheter can be slowly withdrawn, for example towards a lumen of a larger bore catheter, as aspiration is applied to effect embolus removal.

Withdrawing an embolus corked at the distal opening of the catheter back to the distal opening of the guide sheath can increase the risk of fragmentation and embolization depending on the distance it must be withdrawn before being fully encapsulated within a lumen. Thus, it is desirable to use a nested system of successively larger catheter sizes to create a family of aspiration catheters all working from a single point of operation via the single RHV. This allows for the smallest bore catheter advanced most distal to withdraw only a short distance into a larger bore catheter, which in turn can suction the embolus en toto, or, if needed, be withdrawn another short distance into a larger bore catheter that can suction the embolus from the body. The likelihood of the captured clot from fragmenting is thereby reduced and the likelihood of the clot being aspirated en toto is increased.

The guide sheath can be a large 7 F sheath configured to receive a larger bore catheter having an inner diameter of approximately 0.088", which in turn can receive an intermediate bore catheter having an inner diameter of approximately 0.070", which in turn can receive a smaller bore catheter having an inner diameter of approximately 0.054". Any of a variety of sizes is considered herein and that these examples are not intended to be limiting.

Although the larger bore catheter can more efficiently capture the embolus by aspiration, there is a possibility that the substantially larger dimension of the larger bore catheter can prevent it being advanced to reach the embolus without additional manipulations. In some implementations, a smaller bore catheter extending through the lumen of the larger bore catheter can be advanced to the face of the embolus. The smaller bore catheter (and its catheter advancement element) can be held fixed such that the larger bore catheter is advanced over the smaller bore catheter as distal as possible. If the larger bore catheter crawling over the smaller bore catheter is able to reach the embolus in this way, the catheter advancement element can be removed from the smaller bore catheter, the RHV closed to a seal, and aspiration initiated. Both the distal end of the smaller bore catheter and the distal end of the larger bore catheter are positioned at the face of the embolus. The smaller bore catheter can be removed from the system under continuous aspiration. If free flow is established with aspiration (e.g. as seen by the flow into the aspiration source), the operator can leave the larger bore catheter in place and consider whether to perform angiography to confirm establishment reconstitution of antegrade flow and resolution of the obstruction after insuring that the large-bore catheter is completely free of debris with aggressive aspiration and flushing. If free flow is not established, the aspiration can be continued and removal of the smaller bore catheter can be followed by removal of the larger bore catheter thereby removing the embolus from the body using the higher flow and forces generated by the larger bore catheter under full aspiration without the smaller bore catheter positioned within its lumen obstructing flow. A single, shared aspiration source may be used during removal of both the smaller bore and the larger bore catheters.

If the larger bore catheter is not able to reach the target embolus by crawling over the smaller bore catheter, the larger bore catheter and the catheter advancement element for the smaller bore catheter can be held fixed at the RHV such that the smaller bore catheter can be advanced between them to the face of the embolus. The smaller bore catheter can then provide a rail for another attempt at advancing the larger bore catheter towards the face of the embolus. These steps can be repeated in sequence to "inch" the larger bore catheter toward the embolus until both the distal end of the smaller bore catheter and the distal end of the larger bore catheter are positioned near the face of the embolus such that aspiration embolectomy can be performed through them.

The smaller bore catheter can be attached to the embolus and withdraw the embolus towards the larger bore catheter. Thus, where the embolus may be too large to fully enter the lumen of the smaller bore catheter it may be engulfed or retrieved by the lumen of the larger bore catheter. The smaller bore catheter having embolus attached to the distal end by aspiration can be withdrawn followed immediately by capture and withdrawal of the embolus via the larger bore catheter under aspiration.

Tension can get stored in a catheter system advanced through tortuous cerebral anatomy. Downward and lateral forces may be created on the supporting catheter system as the distal tip of the catheter meets resistance. The entire system can propel forward as the distal tip of the catheter is released past these points of resistance. The resistance can occur at the tortuosity in the vessel or at obstructions or bifurcations or due to preexisting implants or other causes. Typically, the tension is stored without loss of position. The resultant effect is a back-and-forth type movement of the system to reach the target and the steady storage of tension in the guide sheath as it is relentlessly pushed downward (i.e. proximally back against the direction of insertion).

In the case of aspiration systems for stroke, the same stored tension can occur with advancement of a larger bore catheter (e.g. an 0.088" ID catheter). As the larger bore catheter develops stored tension and the operator tries to advance it to the target embolus (e.g. in the M1 branch of the MCA), the larger bore catheter traverses the anatomy in a "greater curve to greater curve" manner introducing an amount of slack in the system. The stored tension creates the resistance that causes a catheter to jam at a point and not reach a target. Should the larger bore catheter not reach the target, a smaller bore catheter can be advanced to reach the embolus due to smaller diameter and better deliverability. The smaller bore catheter can navigate the stored tension and also navigate the anatomy in a "greater curve to greater curve" manner as the larger bore catheter did. The smaller bore catheter can anchor onto the embolus via the aspiration pressure applied through the system. The smaller bore catheter can be fixed at the point of occlusion and aspiration turned on to maximum (e.g. via a pump). This affixes or anchors the smaller bore catheter to the embolus such that the operator can "straighten" the entire system and thereby apply a proximally-directed force on the smaller bore catheter to remove slack relative to the surrounding anatomy while the distal end of the smaller bore catheter remains anchored onto the occlusion. The catheters once the slack is reduced now traverse the anatomy in a "lesser curve to lesser curve" manner rather than a "greater curve to greater curve" manner thereby straightening their course relative to the surrounding anatomy. A straightened course allows the larger bore catheter to be advanced over the anchored smaller bore catheter such that its distal end can also reach the embolus target. Aspiration and anchoring through the smaller bore catheter is maintained and the operator creates a straighter, tension-free course to "rail" the larger bore catheter through it over the smaller bore catheter. Once the larger bore catheter is in place—even if the larger catheter does not reach the embolus—substantial embolic protection is afforded and off-target-embolization avoided, particularly if the larger bore catheter is placed distal to the nearest bifurcation proximal to the embolus site.

Once the larger bore catheter is in position, the smaller bore catheter extending through it can be withdrawn. Aspiration may still be applied by the single aspiration source and the seal between the corked embolus maintained as the smaller bore catheter is withdrawn towards the distal end of the larger bore catheter. Once the smaller bore catheter is pulled into the distal end of the larger bore catheter, the aspiration pressure may be automatically turned on within the larger bore catheter such that the embolus is captured within the lumen of the larger bore catheter. Due to the larger inner diameter, the embolus under continuous aspiration pressure via the single, shared aspiration source will likely evacuate the embolus. The smaller bore catheter and the larger bore catheter can both be withdrawn from the system.

Materials

One or more components of the catheters described herein may include or be made from a variety of materials including one or more of a metal, metal alloy, polymer, a metal-polymer composite, ceramics, hydrophilic polymers, polyacrylamide, polyethers, polyamides, polyethylenes, polyurethanes, copolymers thereof, polyvinyl chloride (PVC), PEO, PEO-impregnated polyurethanes such as Hydrothane, Tecophilic polyurethane, Tecothane, PEO soft segmented polyurethane blended with Tecoflex, thermoplastic starch, PVP, and combinations thereof, and the like, or other suitable materials.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material and as described elsewhere herein.

Inner liner materials of the catheters described herein can include low friction polymers such as PTFE (polytetrafluoroethylene) or FEP (fluorinated ethylene propylene), PTFE with polyurethane layer (Tecoflex). Reinforcement layer materials of the catheters described herein can be incorporated to provide mechanical integrity for applying torque and/or to prevent flattening or kinking such as metals including stainless steel, Nitinol, Nitinol braid, helical ribbon, helical wire, cut stainless steel, or the like, or stiff polymers such as PEEK. Reinforcement fiber materials of the catheters described herein can include various high tenacity polymers like Kevlar, polyester, meta-para-aramide, PEEK, single fiber, multi-fiber bundles, high tensile strength polymers, metals, or alloys, and the like. Outer jacket materials of the catheters described herein can provide mechanical integrity and can be contracted of a variety of materials such as polyethylene, polyurethane, PEBAX, nylon, Tecothane, and the like. Other coating materials of the catheters described herein include paralene, Teflon, silicone, polyimide-polytetrafluoroetheylene, and the like.

EXAMPLES

The catheter systems described herein were tested using a system such as that shown in FIG. 12 for measuring bending forces and the data is provided below. A first catheter system incorporated a catheter advancement element having an outer diameter sized to extend through a catheter having an inner diameter of about 0.054" (Version A). A second catheter system incorporated a catheter advancement element having an outer diameter sized to extend through a catheter having an inner diameter of about 0.070" (Versions B1 and B2). A third catheter system incorporated a catheter advancement element having an outer diameter sized to extend through a catheter having an inner diameter of about 0.088" (Version C).

At least three points along the tapered tip portion of the catheter advancement elements were tested (see P1, P2, P3, P4 of FIGS. 13A-13B). The distal point P1 of the at least three points was located a distance of about 5 mm proximal from the distal-most end of the catheter advancement element. The second point P2 of the distal tip portion was an intermediate point of the at least three points located a distance proximal from the distal point P1. For Version A, the second point P2 was about 12 mm proximal from the distal-most end of the catheter advancement element. For Versions B1, B2, and C, the second point P2 was about 20 mm proximal from the distal-most end of the catheter advancement element. A proximal point P3 of the at least points can be located a distance proximal from the intermediate point P2 and was about 13 mm proximal from the distal-most end of the catheter advancement element for Version A and about 25 mm proximal for Versions B1, B2, and C. Some catheter system versions included a fourth point P4. P4 was measured for both Versions B1, B2, and C at about 27 mm, 27 mm, and 28 mm, respectively.

The catheter systems were placed in the advancement configuration and soaked in a bath at 37° C. for a period of time prior to testing. The advancement configuration for the experiment is when the catheter advancement element is positioned coaxially within the lumen of the distal catheter portion of the catheter such that the at least one snug point of the tubular portion is substantially aligned with the distal end of the catheter and the distal tip portion of the catheter advancement element extends distal to the distal end of the catheter. The region near P3 on the catheter advancement element formed a snug point with the catheter where the difference between the inner diameter and the outer diameter at the snug point was no more than about 0.010". The difference was about 0.006" for Version A and about 0.008" for Versions B1 and C. Each of points P1, P2, P3, and P4 (where appropriate) were located on the tip portion of the catheter advancement element and extended distal to the distal end of the catheter.

A fifth point P5 was measured for all versions providing a bending force for the catheter advancement element only proximal to the snug point (see FIG. 13B). The fifth point P5 was at a location positioned inside the catheter when the system is in the advancement configuration, however, P5 took into account the bending force measurement of only the catheter advancement element. For Version A, this fifth point P5 was measured about 16 mm proximal to the distal terminus of the catheter advancement element. For Versions B1 and C, the fifth point P5 was about 30 mm proximal to the distal terminus of the catheter advancement element. When the components of the catheter system are in the advancement configuration, this fifth point P5 on the catheter advancement element can be located inside the catheter. Thus, P5 was measured on the catheter advancement element without the catheter being present.

At least two points along the catheter system were also tested to measure bending force of the system while in the advancement configuration (see S1 and S2 of FIGS. 13A-13B). The first system point S1 took into account the combined bending force of the catheter and the bending force of the catheter advancement element extending through the catheter and is represented by a hashed line in FIG. 13B. The first system point S1 of the at least two system points was located proximal to the distal end of the catheter by a gauge length of about 5 mm or about 19 mm from the distal-most terminus of the catheter system for Version A and about 33 mm and 34 mm, respectively, from the distal-most terminus of the catheter system for Versions B1/B2 and C.

A second system point S2 of the at least two system points was located distal to the first system point S1 by a distance. The second system point S2 took into account the bending force of the catheter advancement element extending outside the catheter. In some tests, the second system point S2 was distal to the distal end of the catheter and was the same as the proximal point P3 or the proximal point P4 (where available).

Table 1 below provides bending forces measured in Newtons (N) of the various points along the length of the catheter systems in the advancement configuration. The points referred to in the table correlate generally to the point shown in FIGS. 13A-13B, although are not represented to scale. The points are illustrative only and different points can be measured.

TABLE 1

| Catheter System Tested | P1 | P2 | P3 | P4 | P5 | S2 | S1 |
| --- | --- | --- | --- | --- | --- | --- | --- |
| | Distal Tip Points (catheter advancement element only) | | | | | System Points | |
| Version A 0.054" | 0.023N | 0.079N | 0.087N | n/a | 0.061N | 0.087N | 0.208N |
| Distance along length of system from distal-most terminus | 5 mm | 12 mm | 13 mm | n/a | 16 mm | 13 mm | 19 mm |
| Version B1 0.070" | 0.025N | 0.180N | 0.211N | 0.233N | 0.155N | 0.211N | 0.442N |
| Distance along length of system from distal-most terminus | 5 mm | 20 mm | 25 mm | 27 mm | 30 mm | 25 mm | 33 mm |
| Version B2 0.070" | 0.025N | 0.180N | 0.211N | 0.233N | 0.155N | 0.211N | 0.345N |
| Distance along length of system from distal-most terminus | 5 mm | 20 mm | 25 mm | 27 mm | 30 mm | 25 mm | 33 mm |
| Version C 0.088" | 0.029N | 0.210N | 0.245N | 0.299N | 0.219N | 0.245N | 0.415N |
| Distance along length of system from distal-most terminus | 5 mm | 20 mm | 25 mm | 28 mm | 30 mm | 25 mm | 34 mm |

Table 1 shows the bending force of the distal end of the catheter advancement element at P1 was no more than about 0.05 N. A difference between the bending force of P2 and the bending force of P1 divided by the distance between P2 and P1 and/or a difference between the bending force of P3 and the bending force of P2 divided by the distance between P3 and P2 provided a first flexibility slope. The first flexibility slope was about 0.008 N/mm for Version A, 0.010 N/mm for Version B1, and 0.012 N/mm for Version C. A difference between the bending force of P3 and the bending force of P2 divided by the distance between P3 and P2 provided a second flexibility slope. The second flexibility slope was about 0.008 N/mm for Version A, 0.006 N/mm for Version B1, and 0.007 N/mm for Version C. An average of the first flexibility slope and the second flexibility slope defined an average tip portion flexibility slope. In some tests, a fourth distal tip point was measured such that the average tip portion flexibility slope took into account this additional segment in calculating the average slope (e.g. segment between P3 and P4). The average tip portion flexibility slope for each version of the catheter systems tested was at least 0.005 N/mm. For example, the average tip portion flexibility slope for Version A and Version B1 was about 0.008 N/mm, and for Version C was about 0.010 N/mm. A difference between the bending force of S1 and the bending force of S2 (whether P3 or P4) divided by the distance between S1 and S2 (whether P3 or P4) provided a first system flexibility slope. The first system flexibility slope using P3 as S2 was about 0.024 N/mm for Version A, 0.013 N/mm for Version B1, and about 0.009 N/mm for Version C. In this calculation, a ratio between the first system flexibility slope to the average tip portion flexibility slope for Version A was about 3.0, the ratio for Version B was about 1.6, and the ratio for Version C was about 0.9. The first system flexibility slope using P4 as S2 was about 0.035 N/mm for Version B1 and about 0.02 N/mm for Version C. In this calculation, a ratio between the first system flexibility slope to the average tip portion flexibility slope for Version B1 was about 4.4, and the ratio for Version C was about 2.0. Regardless which point is used for S2 (whether P3 or P4), the ratio between the first system flexibility slope to the average tip portion flexibility slope was less than about 5 for each version.

Figure 14A:
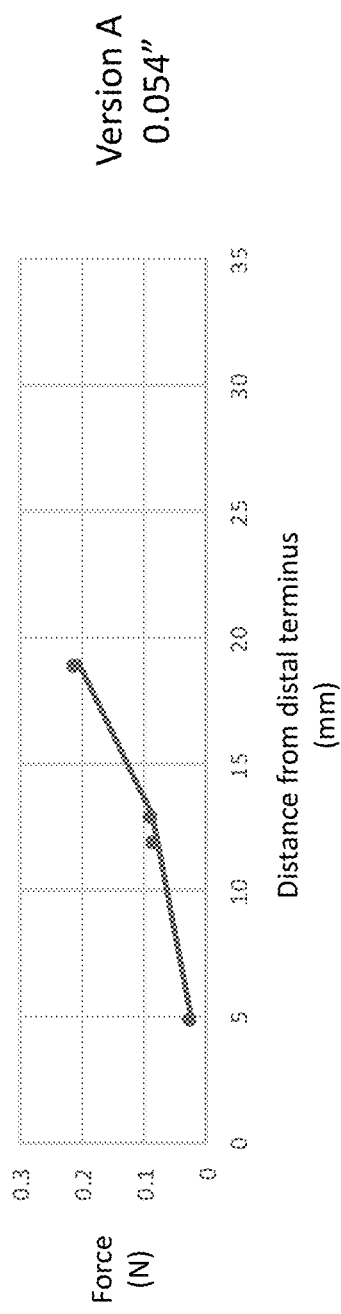
FIG. 14A is a graph of the bending forces along a length of a catheter system formed of a catheter advancement element configured to extend through a catheter having an inner diameter of 0.054"
Figure 14B:
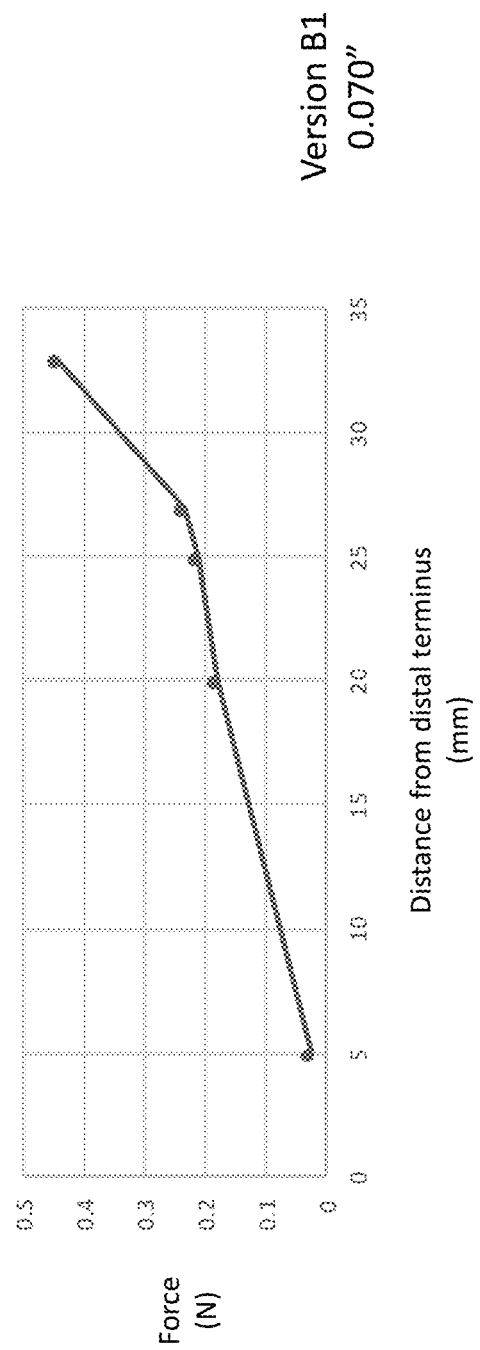
FIG. 14B is a graph of the bending forces along a length of a catheter system formed of a catheter advancement element configured to extend through a catheter having an inner diameter of 0.070"
Figure 14C:
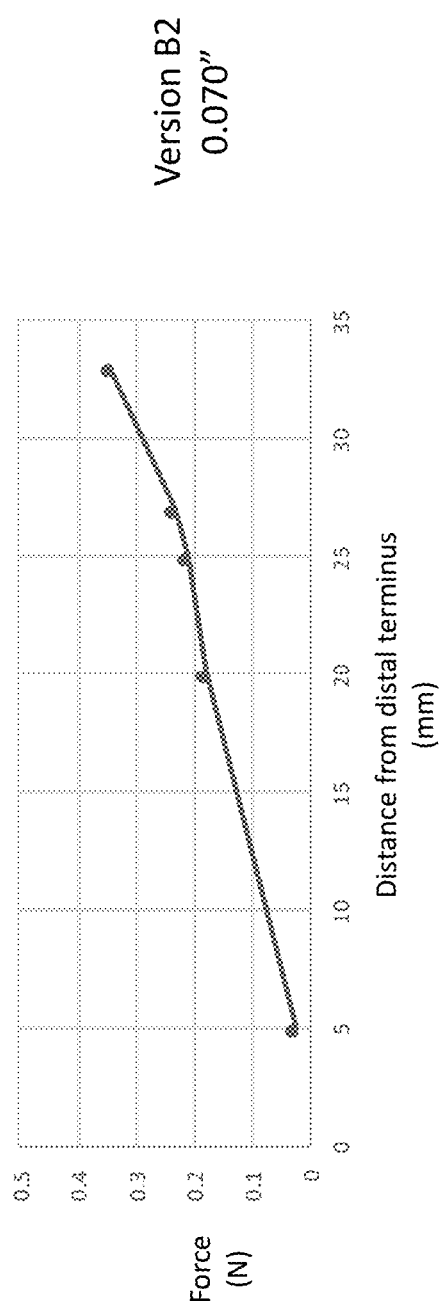
FIG. 14C is a graph of the bending forces along a length of a catheter system formed of a catheter advancement element configured to extend through a catheter having an inner diameter of 0.070"
Figure 14D:
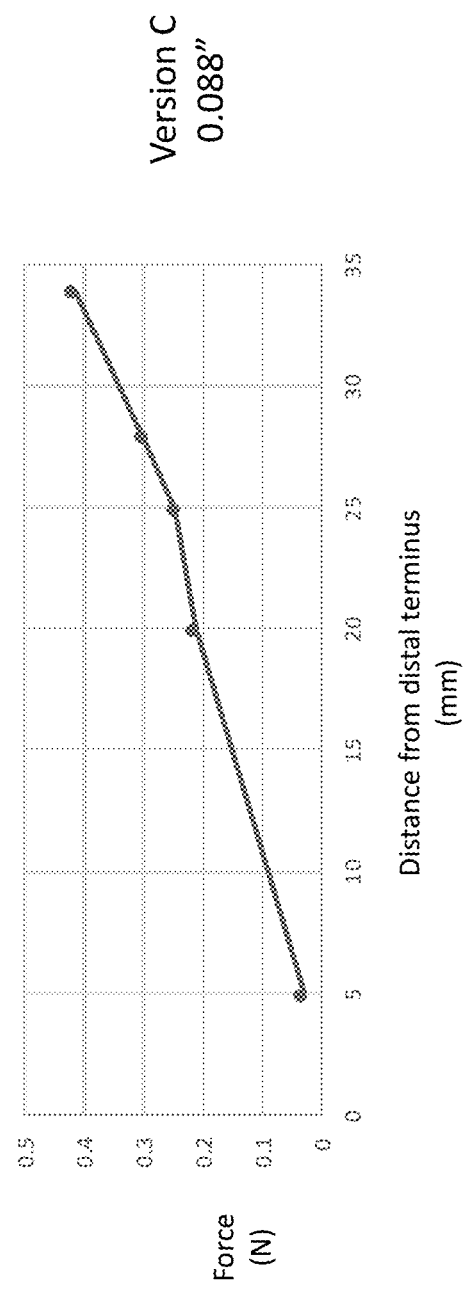
FIG. 14D is a graph of the bending forces along a length of a catheter system formed of a catheter advancement element configured to extend through a catheter having an inner diameter of 0.088"

FIGS. 14A-14D illustrate the bending forces of the various points described above versus distance in mm along a length of the system. FIG. 14A illustrates data for Version A system incorporating a catheter advancement element 300 having an outer diameter sized to extend through a catheter having an inner diameter of about 0.054". FIG. 14B illustrates data for Version B1 system incorporating a catheter advancement element 300 having an outer diameter sized to extend through a catheter having an inner diameter of about 0.070". FIG. 14C illustrates data for another version (Version B2) of a catheter system incorporating a catheter advancement element 300 having an outer diameter sized to extend through a catheter having an inner diameter of about 0.070". FIG. 14D illustrates data for Version C system incorporating a catheter advancement element 300 having an outer diameter sized to extend through a catheter having an inner diameter of about 0.088".

FIGS. 14A-14D illustrate how the slopes of the lines are substantially constant or close to constant and substantially devoid of step-increases in bending force slope from one segment to the next along the length of the catheter system. In particular, each of the versions tested had no step-increases in bending force between the distal tip points (i.e. the points of the catheter advancement element extending distal to the distal end of the catheter) and the system point (i.e. the combination of the catheter and the catheter advancement element). As such, the overall slope of the system when in the advancement configuration is substantially constant over a length of the system, for example, a length being from a distal-most terminus (0 mm) to about 35 mm proximal to the distal-most terminus of the system.

In each version tested, the bending force of the distal end of the catheter advancement element at P1 was significantly lower than the bending force of the distal end of the catheter through which it extends (e.g. greater than at least about 2×) (see also Table 4 below). The bending force of the distal end of the catheter advancement element at P1 was no more than about 0.05 N. The bending force of the catheter advancement element increased over the length of the distal tip portion to approach the higher bending force of the distal end of the catheter. For example, the distal tip portion increased in stiffness over its length by at least 2× to approach the bending force of the distal end of the catheter. The bending force of the catheter system over its length had a generally constant slope. This generally constant slope of increasing bending force for the distal tip portion of the catheter advancement element (shown as a hash-dot-hash line in FIG. 13B) transitioned to a generally constant slope of increasing bending force for the combined system (shown as a hashed line in FIG. 13B) such that there is no significant step-increase in slope between the two. The bending force of the distal tip portion had a slope that transitioned to the slope of the system as a whole (i.e. additive bending force between catheter and catheter advancement shown by hashed line) without a significant step-increase in slope from one segment to the next.

Corresponding points on a different catheter system (GUIDELINER Navigational catheter system; Vascular Solutions, Minneapolis, Minn.) were tested as a comparison. The data is provided in Table 2 below and also in FIG. 14E, which illustrates the bending force of the various points versus distance in mm along a length of the GUIDELINER system.

TABLE 2

| Catheter System | P1 | P2 | P3 | S2 | S1 |
| --- | --- | --- | --- | --- | --- |
| | Distal Tip Points (Navigational catheter only) | | | System Points | |
| 8F GUIDELINER Navigational catheter | 0.114N | 0.137N | 0.141N | 0.141N | 0.636N |
| Distance along length of system from distal-most terminus | 5 mm | 10 mm | 15 mm | 15 mm | 20 mm |

The first bending force of P1 was greater than 0.05 N, specifically about 0.114 N. Various calculations using the bending force data shown in Table 2 were performed. The first flexibility slope for the GUIDELINER system was about 0.005 N/mm. The second flexibility slope for the GUIDELINER system was about 0.001 N/mm. The average tip portion flexibility slope for the GUIDELINER system was about 0.003 N/mm. The first system flexibility slope for the GUIDELINER system was about 0.10 N/mm. The ratio between the first system flexibility slope to the average tip portion flexibility slope for the GUIDELINER system was greater than 30. This ratio illustrates numerically what can be seen graphically in FIG. 14E. FIG. 14E shows the GUIDELINER catheter system undergoes a large step-increase in slope from the flexibility of the portion of the navigation catheter extending distal to the distal end of the catheter through which it extends and the flexibility of the system as a whole. These large step-increases in slope means that there are sharp transitions in stiffness along the length of the catheter system that prevent the GUIDELINER catheter system from being advanced around curves of the tortuous vessels traversing the bony anatomy of the skull. The catheter tip is prevented from passing through such curves. In contrast, the catheter systems described herein have smaller slope ratios, which illustrate they possess the smoothest possible transition in stiffness from distal to proximal end and thus, are suitable for delivery through tortuous anatomy.

Table 3 below shows slopes of the catheter systems described herein compared to the slopes of the GUIDELINER Navigation Catheter system. "Average tip portion flexibility slope" was calculated. More specifically, the average tip portion flexibility slope is the average of the slopes of segments P1 to P2, P2 to P3, and P3 to P4, where available. Additional segments of the tip portion can be included. "Slope of segment S2-S1" is the slope of the segment between system points S2 and S1. The system point S2 can be the same point or a different point as one of the other points (e.g. P4 or P3). "Slope of segment P1-S1" is the slope of a line drawn from distal-most point P1 directly to the system point S1.

TABLE 3

| Catheter System | P1 (N) | P2 (N) | P3 (N) | P4 (N) | S2 (N) | S1 (N) | Average tip portion flexibility slope (N/mm) | Slope of segment S2-S1 (N/mm) | Slope of segment P1-S1 (N/mm) |
|---|---|---|---|---|---|---|---|---|---|
| Version A 0.054" | 0.023 | 0.079 | 0.087 | n/a | 0.087 | 0.208 | 0.0080 | 0.0202 | 0.0132 |
| Ratio to average tip portion flexibility slope | | | | | | | 1 | 2.52 | 1.65 |
| Version B1 0.070" | 0.025 | 0.180 | 0.211 | 0.233 | 0.233 | 0.442 | 0.0093 | 0.0349 | 0.0149 |
| Ratio to average tip portion flexibility slope | | | | | | | 1 | 3.76 | 1.61 |
| Version B2 0.070" | 0.025 | 0.180 | 0.211 | 0.233 | 0.233 | 0.345 | 0.0093 | 0.0187 | 0.0114 |
| Ratio to average tip portion flexibility slope | | | | | | | 1 | 2.01 | 1.23 |
| Version C 0.088" | 0.029 | 0.210 | 0.245 | 0.299 | 0.299 | 0.415 | 0.0124 | 0.0193 | 0.0133 |
| Ratio to average tip portion flexibility slope | | | | | | | 1 | 1.56 | 1.07 |
| GUIDELINER Navigation Catheter | 0.114 | 0.137 | 0.141 | n/a | 0.141 | 0.636 | 0.0026 | 0.0990 | 0.0348 |
| Ratio to average tip portion flexibility slope | | | | | | | 1 | 37.40 | 13.13 |

The tapered distal tip portion underwent a change in bending force over its length that was at least a 2-fold increase. The tapered distal tip portion of the catheter advancement element of Versions A, B1, B2, and C had a minimum slope of at least 0.005 N/mm. In contrast, the GUIDELINER increase in bending force over its length was only about 1.2 times. Further, the GUIDELINER had an average tip portion flexibility slope that was less than about 0.003 N/mm. The slope of each of the catheter systems (Versions A, B1, B2, and C) increased from distal point P1 to system point S1 no more than about 5 times whereas the GUIDELINER increased by more than 30 times from 0.114.

Table 4 below shows the bending forces of the distal tip of the catheter advancement element relative to the bending forces of the distal end of the catheter. The point measured and referred to in the table 4 below as "Catheter Point C1" was a point along a length of the catheter nearest the distal end that is measurable using the systems described herein, for example, a gauge length of the catheter from the distal-most end of the catheter of at least about 5 mm. The bending force (or flexibility) of the distal tip at P1 was about 16% the bending force (or flexibility) of C1 for Version A, about 10% for Version B1 and about 8% for Version C. Thus, the bending force at P1 was between about 5% and 15% the bending force at C1. The bending force (or flexibility) of the snug point near the proximal end of the distal tip (e.g., P3 or P4) was about 59% for Version A, about 91% for Version B1, and about 82% for Version C. Thus, the bending force at the snug point was between about 50% and 90% the bending force (or flexibility) of C1. In contrast, the distal tip point P1 on the GUIDELINER was stiffer compared to the same point on versions A, B1, or C. The proximal point P3 on the GUIDELINER had a greater bending force compared to its distal tip point P1, but this bending force was much lower compared to the bending force of the catheter point C1 (i.e. only 23% the stiffness of the catheter point C1). Thus, there was a larger difference between the bending force of the navigation catheter at P3 compared to the bending force of the catheter at C1 compared to the versions of the catheter systems described herein. This difference contributes to the larger step-increase in slopes of the GUIDELINER catheter system as best visualized in FIG. 14E,

TABLE 4

| Catheter System | Distal Tip P1 (N) (Catheter Advancement Element only) | Proximal Point P3/P4 (N) (Catheter Advancement Element only) | Catheter Point C1 (N) Catheter only |
|---|---|---|---|
| Version A 0.054" | 0.023 | 0.087 | 0.147 |
| | 16% | 59% | 100% |
| Version B1 0.070" | 0.025 | 0.233 | 0.256 |
| | 10% | 91% | 100% |
| Version C 0.088" | 0.029 | 0.299 | 0.366 |
| | 8% | 82% | 100% |

TABLE 4-continued

| Catheter System | Distal Tip P1 (N) | Proximal Point P3/P4 (N) (Catheter Advancement Element only) | Catheter Point C1 (N) Catheter only |
|---|---|---|---|
| 8F GUIDELINER Navigational catheter | 0.114 | 0.141 | 0.624 |
|  | 18% | 23% | 100% |

Table 5 below shows the bending force of P1 of the catheter advancement element relative to a bending force of a portion of the proximal extension of the catheter advancement element. Point E1 on the proximal extension that was selected for testing was within about 20 cm proximal to the tubular portion of the catheter advancement element. The point E1 had a bending force that was about 9.21 N. The bending force of the catheter advancement element at the distal tip P1 was no more than about 0.30% of the bending force of the proximal extension at E1. The ratio of the bending force of point E1 to the first bending force at distal tip point P1 was at least about 300. The proximal extension of the catheter advancement element of Version C was about 318 times stiffer than the distal tip of the catheter advancement element at P1, Version B1 was about 368 times stiffer, and Version A was about 400 times stiffer.

TABLE 5

| Catheter System | P1 (N) | E1 (N) | % stiffness | Ratio |
|---|---|---|---|---|
| Version A 0.054" | 0.023 | 9.21 | 0.25% | 400 |
| Version B1 0.070" | 0.025 | 9.21 | 0.27% | 368 |
| Version C 0.088" | 0.029 | 9.21 | 0.30% | 318 |
| GUIDELINER Navigation Catheter | 0.114 | 17.52 | 0.65% | 154 |
| Orion-21 | 0.137 | 8.36 | 1.64% | 61 |

Two other catheter systems were analyzed as a comparison. The bending force of the GUIDELINER navigation catheter at E1 was greater than any of the versions tested at about 17.52N. The bending force of the distal tip at P1 was also higher compared to the catheter system versions described herein. The bending force of the navigation catheter at the distal tip P1 was about 0.65% the bending force of the proximal extension at E1. Further, the bending force at point E1 of the GUIDELINER navigation catheter was only 154 times more than the distal tip P1. The ORION-21 catheter (Medtronic, Minneapolis, Minn.) had a bending force at the distal tip P1 that was about 1.64% the bending force at E1. The bending force at point E1 of the ORION-21 was only about 60 times stiffer than its distal tip at P1.

The data described herein provides a numerical picture of the smooth transition in flexibility over the length of the various catheter systems described herein that provides optimum navigability without risk of kinking. The catheter systems described herein have distal ends that are exceptionally flexible that transition towards proximal ends that are exceptionally stiff for optimum torqueing and manipulation. The transitions in flexibility along the length of the system are managed such that the two components work seamlessly together as if they were a single component and without any large step-increases in stiffness from one segment to another.

Implementations describe catheters and delivery systems and methods to deliver catheters to target anatomies. However, while some implementations are described with specific regard to delivering catheters to a target vessel of a neurovascular anatomy such as a cerebral vessel, the implementations are not so limited and certain implementations may also be applicable to other uses. For example, the catheters can be adapted for delivery to different neuroanatomies, such as subclavian, vertebral, carotid vessels as well as to the coronary anatomy or peripheral vascular anatomy, to name only a few possible applications. Although the systems described herein are described as being useful for treating a particular condition or pathology, that the condition or pathology being treated may vary and are not intended to be limiting. Use of the terms "embolus," "embolic," "emboli," "thrombus," "occlusion," "clot", etc. that relate to a target for treatment using the devices described herein are not intended to be limiting. The terms may be used interchangeably and can include, but are not limited to a blood clot, air bubble, small fatty deposit, or other object carried within the bloodstream to a distant site or formed at a location in a vessel. The terms may be used interchangeably herein to refer to something that can cause a partial or full occlusion of blood flow through or within the vessel.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation," "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. The reference point used herein may be the operator such that the terms "proximal" and "distal" are in reference to an operator using the device. A region of the device that is closer to an operator may be described herein as "proximal" and a region of the device that is further away from an operator may be described herein as "distal". Similarly, the terms "proximal" and "distal" may also be used herein to refer to anatomical locations of a patient from the perspective of an operator or from the perspective of an entry point or along a path of insertion from the entry point of the system. As such, a location that is proximal may mean a location in the patient that is closer to an entry point of the device along a path of insertion towards a target and a location that is distal may mean a location in a patient that is further away from an entry point of the device along a path of insertion towards the target location. However, such terms are provided to establish relative frames of reference, and are not intended to limit the use or orientation of the catheters and/or delivery systems to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A method of performing a medical procedure in a cerebral vessel of a patient, the method comprising:
    advancing a first catheter system towards an embolus within a cerebral blood vessel, the first catheter system comprising:
        a first catheter comprising a first catheter portion having a lumen, a proximal opening into the lumen, a distal opening from the lumen, and a distal end; and a first proximal extension coupled to the first catheter portion near the proximal opening, the first proximal extension being less flexible than the first catheter portion;
    advancing a second catheter system towards the embolus through the first catheter, the second catheter system comprising:
        a second catheter comprising a second catheter portion having a lumen, a proximal opening into the lumen, a distal opening from the lumen, and a distal end, and a second proximal extension coupled to the second catheter portion near the proximal opening, the second proximal extension being less flexible than the second catheter portion;
    wherein an outer diameter of the second catheter portion and an inner diameter of the first catheter portion are configured to provide a first seal;
    applying aspiration pressure through the lumen of the second catheter portion;
    anchoring the distal end of the second catheter portion onto the embolus via the aspiration pressure;
    applying a proximally-directed force on the second catheter; and
    advancing the first catheter over the second catheter towards the embolus while the distal end of the second catheter remains anchored onto the embolus; and
    automatically applying aspiration pressure within the first catheter portion upon the second catheter portion entering into the first catheter portion.

2. The method of claim 1, wherein the applying the proximally-directed force on the second catheter reduces slack in the second catheter relative to surrounding anatomy while the distal end of the second catheter portion remains anchored onto the embolus.

3. The method of claim 1, further comprising a guide sheath having a working lumen and a single continuous shared aspiration source applying the aspiration pressure through the lumen of the second catheter portion.

4. The method of claim 3, wherein the first seal between the outer diameter of the second catheter portion and the inner diameter of the first catheter portion forms a contiguous lumen between the distal opening of the second catheter portion and the proximal end of the guide sheath.

5. The method of claim 4, further comprising a second seal between an outer diameter of the first catheter portion and an inner diameter of the guide sheath, wherein the lumen of the second catheter portion fluidly communicates with the lumen of the first catheter portion that fluidly communicates with the working lumen of the guide sheath forming a contiguous sealed lumen formed of three sections of increasingly larger dimensions towards the proximal end of the catheter system.

6. The method of claim 3, wherein the system comprises a single or two-headed rotating hemostatic valve on the guide sheath, wherein both the first and second catheters are advanced through the hemostatic valve.

7. The method of claim 3, further comprising advancing a distal opening of the guide sheath working lumen to a location in a distal internal carotid artery (ICA).

8. The method of claim 1, wherein the second catheter portion has an inner diameter that is between 0.054" and 0.070", the first catheter portion has an inner diameter between 0.072" and 0.088", and the guide sheath is between 6 Fr to 8 Fr.

9. The method of claim 1, wherein the embolus is not penetrated by a guidewire or microcatheter during the method.

10. The method of claim 1, wherein the first catheter portion has an outer diameter that is larger than an outer diameter of the first proximal extension.

11. The method of claim 10, wherein the second catheter portion has an outer diameter that is larger than an outer diameter of the second proximal extension.

12. The method of claim 10, wherein the first proximal extension is a ribbon, spine or hypotube.

13. The method of claim 10, wherein the first proximal extension is solid.

14. The method of claim 1, further comprising a third catheter comprising a third catheter portion having a lumen, a proximal opening into the lumen, a distal opening from the lumen, and a distal end, the third catheter also comprising a third proximal extension coupled to the third catheter portion near the proximal opening of the third catheter, and wherein the third catheter portion has an outer diameter sized to extend through the lumen of the second catheter portion.

15. The method of claim 1, wherein the automatic application of aspiration pressure within the first catheter portion captures the embolus within the lumen of the first catheter portion.

16. The method of claim 1, wherein the first catheter system comprises a first delivery element comprising a flexible elongate body and a soft, tapered distal tip portion, at least a portion of the elongate body positioned within the lumen of the first catheter portion and the tapered distal tip portion extending distal to the distal end of the first catheter portion, wherein the first delivery element is withdrawn from the lumen of the first catheter portion prior to advancing the second catheter system.

17. The method of claim 1, wherein the second catheter system further comprises a second delivery element comprising a flexible elongate body and a soft, tapered distal tip portion, at least a portion of the elongate body positioned within the lumen of the second catheter portion and the tapered distal tip portion extending distal to the distal end of the second catheter portion.

18. The method of claim 1, wherein the second catheter portion enters the first catheter portion upon withdrawing the second catheter with respect to the first catheter.

19. The method of claim 1, wherein the second catheter portion enters the first catheter portion upon advancing the first catheter with respect to the second catheter.

* * * * *

UNITED STATES PATENT AND TRADEMARK OFFICE
CERTIFICATE OF CORRECTION

| | | |
|---|---|---|
| PATENT NO. | : 11,607,523 B2 | Page 1 of 1 |
| APPLICATION NO. | : 16/414532 | |
| DATED | : March 21, 2023 | |
| INVENTOR(S) | : Chou | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 784 days.

Signed and Sealed this
Thirty-first Day of December, 2024

Derrick Brent
*Acting Director of the United States Patent and Trademark Office*